United States Patent
Lowe, Jr. et al.

(10) Patent No.: US 11,964,275 B2
(45) Date of Patent: Apr. 23, 2024

(54) MICROFLUIDIC APPARATUS HAVING AN OPTIMIZED ELECTROWETTING SURFACE AND RELATED SYSTEMS AND METHODS

(71) Applicant: Berkeley Lights, Inc., Emeryville, CA (US)

(72) Inventors: Randall D. Lowe, Jr., Emeryville, CA (US); Shao Ning Pei, Albany, CA (US); Jian Gong, Danville, CA (US); Alexander J. Mastroianni, Alameda, CA (US); Jason M. McEwen, El Cerrito, CA (US); Justin K. Valley, Berkeley, CA (US)

(73) Assignee: Berkeley Lights, Inc., Emeryville, CA (US)

( * ) Notice: Subject to any disclaimer, the term of this patent is extended or adjusted under 35 U.S.C. 154(b) by 625 days.

(21) Appl. No.: 17/005,116

(22) Filed: Aug. 27, 2020

(65) Prior Publication Data

US 2021/0114020 A1 Apr. 22, 2021

Related U.S. Application Data

(63) Continuation of application No. 15/336,768, filed on Oct. 27, 2016, now Pat. No. 10,799,865, which is a
(Continued)

(51) Int. Cl.
*B01L 3/00* (2006.01)
*C12M 1/00* (2006.01)
*C12M 3/06* (2006.01)

(52) U.S. Cl.
CPC ......... *B01L 3/50273* (2013.01); *C12M 23/16* (2013.01); *C12M 29/10* (2013.01);
(Continued)

(58) Field of Classification Search
CPC ......... B01L 3/50273; B01L 2200/0647; B01L 2200/12; B01L 2300/0816;
(Continued)

(56) References Cited

U.S. PATENT DOCUMENTS

| 5,814,200 A | 9/1998 | Pethig et al. |
| 6,294,063 B1 | 9/2001 | Becker et al. |

(Continued)

FOREIGN PATENT DOCUMENTS

| CN | 1337580 A | 2/2002 |
| CN | 1649887 A | 8/2005 |

(Continued)

OTHER PUBLICATIONS

Shah, Gaurav J., et al. "EWOD-driven droplet microfluidic device integrated with optoelectronic tweezers as an automated platform for cellular isolation and analysis." Lab on a Chip 9.12 (2009): 1732-1739. (Year: 2009).*

(Continued)

*Primary Examiner* — Robert J Eom
(74) *Attorney, Agent, or Firm* — Shay Glenn LLP

(57) ABSTRACT

Microfluidic devices having an electrowetting configuration and an optimized droplet actuation surface are provided. The devices include a conductive substrate having a dielectric layer, a hydrophobic layer covalently bonded to the dielectric layer, and a first electrode electrically coupled to the dielectric layer and configured to be connected to a voltage source. The microfluidic devices also include a second electrode configured to be connected to the voltage source. The hydrophobic layer features self-associating molecules covalently bonded to a surface of the dielectric layer in a
(Continued)

manner that produces a densely-packed monolayer that resists intercalation and or penetration by polar molecules or species. Also provided are microfluidic devices having an electrowetting configuration that further include a section having a dielectrophoresis configuration; systems that include microfluidic devices in combination with an aqueous droplet and a fluidic medium immiscible with the aqueous droplet; related kits; and methods of manipulating droplets within the microfluidic devices.

27 Claims, 22 Drawing Sheets

Related U.S. Application Data continuation-in-part of application No. 15/135,707, filed on Apr. 22, 2016, now Pat. No. 10,723,988.

(60) Provisional application No. 62/410,238, filed on Oct. 19, 2016, provisional application No. 62/342,131, filed on May 26, 2016, provisional application No. 62/247,725, filed on Oct. 28, 2015, provisional application No. 62/246,605, filed on Oct. 27, 2015.

(52) U.S. Cl.
CPC ... *B01L 2200/0647* (2013.01); *B01L 2200/12* (2013.01); *B01L 2300/0816* (2013.01); *B01L 2300/0887* (2013.01); *B01L 2300/12* (2013.01); *B01L 2300/161* (2013.01); *B01L 2400/0427* (2013.01)

(58) Field of Classification Search
CPC ......... B01L 2300/0887; B01L 2300/12; B01L 2300/161; B01L 2400/0427; C12M 23/16; C12M 29/10
See application file for complete search history.

(56) References Cited

U.S. PATENT DOCUMENTS

| | | |
|---|---|---|
| 6,379,929 B1 | 4/2002 | Burns et al. |
| 6,408,878 B2 | 6/2002 | Unger et al. |
| 6,565,727 B1 | 5/2003 | Shenderov |
| 6,773,566 B2 | 8/2004 | Shenderov |
| 6,911,132 B2 | 6/2005 | Pamula et al. |
| 6,942,776 B2 | 9/2005 | Medoro |
| 6,958,132 B2 | 10/2005 | Chiou et al. |
| 6,977,033 B2 | 12/2005 | Becker et al. |
| 7,090,759 B1 | 8/2006 | Seul |
| 7,163,612 B2 | 1/2007 | Sterling et al. |
| 7,252,928 B1 | 8/2007 | Hafeman et al. |
| 7,314,708 B1 | 1/2008 | Heller et al. |
| 7,328,979 B2 | 2/2008 | Decre et al. |
| 7,442,339 B2 | 10/2008 | Sundararajan et al. |
| 7,547,380 B2 | 6/2009 | Velev |
| 7,699,969 B2 | 4/2010 | Manaresi et al. |
| 7,790,631 B2 | 9/2010 | Sharma et al. |
| 7,956,339 B2 | 6/2011 | Ohta et al. |
| 8,037,903 B2 | 10/2011 | Wang et al. |
| 8,093,064 B2 | 1/2012 | Shah et al. |
| 8,228,657 B2 | 7/2012 | Jones et al. |
| 8,349,276 B2 | 1/2013 | Pamula et al. |
| 8,350,243 B2 | 1/2013 | Lee et al. |
| 8,529,743 B2 | 9/2013 | Kim et al. |
| 8,531,082 B2 | 9/2013 | Lee et al. |
| 8,581,167 B2 | 11/2013 | Lean et al. |
| 8,679,843 B2 | 3/2014 | Faris et al. |
| 8,685,344 B2 | 4/2014 | Sudarsan et al. |
| 8,864,972 B2 | 10/2014 | Yamakawa et al. |
| 8,921,041 B2 | 12/2014 | Wang et al. |
| 9,068,281 B2 | 6/2015 | Wu et al. |
| 9,134,513 B2 | 9/2015 | Chen et al. |
| 9,144,806 B2 | 9/2015 | Chen et al. |
| 9,201,042 B2 | 12/2015 | Bhattacharya et al. |
| 9,239,328 B2 | 1/2016 | Chang et al. |
| 9,403,172 B2 | 8/2016 | Short et al. |
| 10,058,865 B2 | 8/2018 | Breinlinger et al. |
| 10,280,456 B2 | 5/2019 | Chang et al. |
| 10,407,658 B2 | 9/2019 | Newstrom et al. |
| 10,723,988 B2 | 7/2020 | Lowe et al. |
| 10,799,865 B2 | 10/2020 | Lowe et al. |
| 2003/0008364 A1 | 1/2003 | Wang et al. |
| 2003/0175947 A1 | 9/2003 | Liu et al. |
| 2003/0198968 A1 | 10/2003 | Matson |
| 2004/0072278 A1 | 4/2004 | Chou et al. |
| 2004/0191789 A1 | 9/2004 | Manaresi et al. |
| 2004/0197905 A1 | 10/2004 | Hafeman |
| 2004/0229349 A1 | 11/2004 | Daridon |
| 2004/0231987 A1 | 11/2004 | Sterling et al. |
| 2005/0089993 A1 | 4/2005 | Boccazzi et al. |
| 2005/0112548 A1 | 5/2005 | Segawa et al. |
| 2005/0129581 A1 | 6/2005 | McBride et al. |
| 2005/0164402 A1 | 7/2005 | Belisle et al. |
| 2005/0175981 A1 | 8/2005 | Voldman et al. |
| 2005/0264351 A1 | 12/2005 | Armit |
| 2005/0274456 A1 | 12/2005 | Roitman et al. |
| 2005/0274612 A1 | 12/2005 | Segawa et al. |
| 2006/0081643 A1* | 4/2006 | Haluzak ............... B01L 3/0255 222/52 |
| 2006/0091015 A1 | 5/2006 | Lau |
| 2006/0091755 A1 | 5/2006 | Carlisle |
| 2006/0097155 A1 | 5/2006 | Adachi et al. |
| 2006/0154361 A1 | 7/2006 | Wikswo et al. |
| 2006/0165565 A1 | 7/2006 | Ermakov |
| 2006/0175192 A1 | 8/2006 | Lin |
| 2006/0186048 A1 | 8/2006 | Tan |
| 2006/0226012 A1 | 10/2006 | Kanagasabapathi et al. |
| 2006/0240548 A1 | 10/2006 | Deutsch et al. |
| 2006/0263612 A1 | 11/2006 | Chen et al. |
| 2007/0023292 A1 | 2/2007 | Kim et al. |
| 2007/0095669 A1 | 5/2007 | Lau et al. |
| 2007/0138016 A1 | 6/2007 | Wang |
| 2007/0148763 A1 | 6/2007 | Huh et al. |
| 2007/0183934 A1 | 8/2007 | Diercks et al. |
| 2007/0242105 A1 | 10/2007 | Srinivasan et al. |
| 2007/0243634 A1 | 10/2007 | Pamula et al. |
| 2007/0264481 A1 | 11/2007 | DeSimone et al. |
| 2007/0292941 A1 | 12/2007 | Handique et al. |
| 2008/0003142 A1 | 1/2008 | Link et al. |
| 2008/0006535 A1 | 1/2008 | Paik et al. |
| 2008/0013092 A1 | 1/2008 | Maltezos et al. |
| 2008/0038810 A1 | 2/2008 | Pollack et al. |
| 2008/0124252 A1 | 5/2008 | Marchand et al. |
| 2008/0153134 A1 | 6/2008 | Wiyatno et al. |
| 2008/0223721 A1 | 9/2008 | Cohen et al. |
| 2008/0225378 A1 | 9/2008 | Weikert et al. |
| 2008/0247920 A1 | 10/2008 | Pollack et al. |
| 2008/0257735 A1 | 10/2008 | Jeon et al. |
| 2008/0274513 A1 | 11/2008 | Shenderov et al. |
| 2008/0299539 A1 | 12/2008 | Lee et al. |
| 2008/0302732 A1 | 12/2008 | Soh et al. |
| 2008/0318203 A1 | 12/2008 | Tran et al. |
| 2009/0023608 A1 | 1/2009 | Hung et al. |
| 2009/0098541 A1 | 4/2009 | Southern et al. |
| 2009/0136912 A1 | 5/2009 | Kurokawa et al. |
| 2009/0137426 A1 | 5/2009 | Jung et al. |
| 2009/0170186 A1 | 7/2009 | Wu et al. |
| 2009/0192044 A1 | 7/2009 | Fouillet |
| 2010/0000366 A1 | 1/2010 | Nomura et al. |
| 2010/0000620 A1 | 1/2010 | Fouillet et al. |
| 2010/0003666 A1 | 1/2010 | Lee et al. |
| 2010/0009335 A1 | 1/2010 | Joseph et al. |
| 2010/0181195 A1 | 7/2010 | Garcia Tello |
| 2010/0206731 A1 | 8/2010 | Lau et al. |
| 2010/0208328 A1 | 8/2010 | Heikenfeld et al. |
| 2010/0273681 A1 | 10/2010 | Cerrina et al. |
| 2010/0316531 A1 | 12/2010 | Delattire et al. |
| 2011/0053151 A1 | 3/2011 | Hansen et al. |
| 2011/0053783 A1 | 3/2011 | Du et al. |
| 2011/0076734 A1 | 3/2011 | Zhou et al. |

(56) References Cited

U.S. PATENT DOCUMENTS

| | | |
|---|---|---|
| 2011/0086377 A1 | 4/2011 | Thwar et al. |
| 2011/0095201 A1 | 4/2011 | Stolowitz |
| 2011/0108422 A1 | 5/2011 | Heller et al. |
| 2011/0117634 A1 | 5/2011 | Halamish et al. |
| 2011/0143964 A1 | 6/2011 | Zhou et al. |
| 2011/0186165 A1 | 8/2011 | Borenstein et al. |
| 2011/0220505 A1 | 9/2011 | Wang et al. |
| 2011/0262906 A1 | 10/2011 | Dimov et al. |
| 2011/0301058 A1 | 12/2011 | Cheng et al. |
| 2012/0009671 A1 | 1/2012 | Hansen et al. |
| 2012/0015347 A1 | 1/2012 | Singhal et al. |
| 2012/0024708 A1 | 2/2012 | Chiou et al. |
| 2012/0073740 A1 | 3/2012 | Hsieh |
| 2012/0118740 A1 | 5/2012 | Garcia et al. |
| 2012/0156675 A1 | 6/2012 | Luerssen et al. |
| 2012/0208266 A1 | 8/2012 | Bookbinder et al. |
| 2012/0305400 A1 | 12/2012 | Nelson et al. |
| 2012/0325665 A1 | 12/2012 | Chiou et al. |
| 2013/0026040 A1 | 1/2013 | Cheng et al. |
| 2013/0062205 A1 | 3/2013 | Hadwen et al. |
| 2013/0115606 A1 | 5/2013 | Hansen et al. |
| 2013/0118901 A1 | 5/2013 | Pollack et al. |
| 2013/0118905 A1 | 5/2013 | Morimoto et al. |
| 2013/0130232 A1 | 5/2013 | Weibel et al. |
| 2013/0146459 A1 | 6/2013 | Bazant et al. |
| 2013/0171546 A1 | 7/2013 | White et al. |
| 2013/0171628 A1 | 7/2013 | Di Carlo et al. |
| 2013/0190212 A1 | 7/2013 | Handique et al. |
| 2013/0204076 A1 | 8/2013 | Han et al. |
| 2013/0206597 A1 | 8/2013 | Wang et al. |
| 2013/0261021 A1 | 10/2013 | Bocchi et al. |
| 2013/0277218 A1 | 10/2013 | Mudrik et al. |
| 2013/0280485 A1 | 10/2013 | Coclite et al. |
| 2013/0288055 A1 | 10/2013 | Doshita et al. |
| 2013/0288065 A1 | 10/2013 | Chen et al. |
| 2013/0288254 A1 | 10/2013 | Pollack et al. |
| 2014/0016176 A1 | 1/2014 | Kodani et al. |
| 2014/0038279 A1 | 2/2014 | Ingber et al. |
| 2014/0057311 A1 | 2/2014 | Kamm et al. |
| 2014/0102900 A1 | 4/2014 | Akella et al. |
| 2014/0116881 A1 | 5/2014 | Chapman et al. |
| 2014/0144518 A1 | 5/2014 | Bohringer et al. |
| 2014/0153079 A1 | 6/2014 | Hsieh |
| 2014/0154703 A1 | 6/2014 | Skelley et al. |
| 2014/0154791 A1 | 6/2014 | North et al. |
| 2014/0255976 A1 | 9/2014 | Chang et al. |
| 2014/0262783 A1 | 9/2014 | Chang et al. |
| 2014/0274771 A1 | 9/2014 | Elizazu et al. |
| 2014/0299472 A1 | 10/2014 | Chang et al. |
| 2014/0308688 A1 | 10/2014 | Grego et al. |
| 2014/0378339 A1 | 12/2014 | Lammertyn et al. |
| 2015/0018226 A1 | 1/2015 | Hansen et al. |
| 2015/0107995 A1 | 4/2015 | Sista et al. |
| 2015/0151298 A1 | 6/2015 | White et al. |
| 2015/0151307 A1 | 6/2015 | Breinlinger et al. |
| 2015/0165436 A1 | 6/2015 | Chapman et al. |
| 2015/0167043 A1 | 6/2015 | Goluch et al. |
| 2015/0306598 A1 | 10/2015 | Khandros et al. |
| 2015/0306599 A1 | 10/2015 | Khandros et al. |
| 2015/0352547 A1 | 12/2015 | Breinlinger et al. |
| 2015/0377831 A1 | 12/2015 | Wheeler et al. |
| 2016/0067711 A1 | 3/2016 | Yoon et al. |
| 2016/0158748 A1 | 6/2016 | Wu et al. |
| 2016/0184821 A1 | 6/2016 | Hobbs et al. |
| 2016/0193604 A1 | 7/2016 | McFarland et al. |
| 2016/0199837 A1 | 7/2016 | Breinlinger et al. |
| 2016/0222224 A1 | 8/2016 | Haag et al. |
| 2016/0252495 A1 | 9/2016 | Ricicova et al. |
| 2016/0257918 A1 | 9/2016 | Chapman et al. |
| 2017/0021366 A1 | 1/2017 | Chapman et al. |
| 2017/0043343 A1 | 2/2017 | Khandros et al. |
| 2018/0099282 A1 | 4/2018 | Breinlinger et al. |
| 2018/0298318 A1 | 10/2018 | Kurz et al. |
| 2019/0240665 A1 | 8/2019 | Lionberger et al. |
| 2019/0275516 A1 | 9/2019 | Lowe et al. |
| 2019/0291103 A1 | 9/2019 | Gelzer et al. |
| 2021/0291171 A1 | 9/2021 | Lowe et al. |
| 2022/0356429 A1 | 11/2022 | Lowe et al. |

FOREIGN PATENT DOCUMENTS

| | | |
|---|---|---|
| CN | 100360683 C | 1/2008 |
| CN | 101275114 A | 10/2008 |
| CN | 101405384 A | 4/2009 |
| CN | 101529251 A | 9/2009 |
| CN | 101592627 A | 12/2009 |
| CN | 101726847 A | 6/2010 |
| CN | 102296029 A | 12/2011 |
| CN | 102500436 A | 6/2012 |
| CN | 102671723 A | 9/2012 |
| CN | 103470852 A | 12/2013 |
| CN | 103502426 A | 1/2014 |
| CN | 103865789 A | 6/2014 |
| CN | 101535466 B | 7/2014 |
| CN | 104048919 A | 9/2014 |
| CN | 104066512 A | 9/2014 |
| CN | 104321143 A | 1/2015 |
| CN | 204079986 U | 1/2015 |
| CN | 102866193 B | 4/2015 |
| CN | 104838273 A | 8/2015 |
| CN | 108495712 A | 9/2018 |
| CN | 107257711 B | 11/2019 |
| CN | 102671724 A | 9/2023 |
| EP | 1065378 A2 | 1/2001 |
| EP | 1065378 B1 | 4/2002 |
| EP | 2570188 A1 | 3/2013 |
| EP | 2647434 A1 | 10/2013 |
| JP | 2004117073 A | 4/2004 |
| JP | 2006220606 A | 8/2006 |
| JP | 2007537729 A | 12/2007 |
| JP | 2008500554 A | 1/2008 |
| JP | 2008505630 A | 2/2008 |
| JP | 2008089752 A | 4/2008 |
| JP | 2008539711 A | 11/2008 |
| JP | 2009538130 A | 11/2009 |
| JP | 46142221 B2 | 1/2011 |
| JP | 2013078758 A | 5/2013 |
| JP | 2015507507 A | 3/2015 |
| JP | 2015070832 A | 4/2015 |
| KR | 20100008222 A | 1/2010 |
| KR | 20120066100 A | 6/2012 |
| KR | 20140078515 A | 6/2014 |
| TW | 550066 B | 1/2003 |
| TW | 200307753 A | 12/2003 |
| TW | 1258456 B | 7/2006 |
| TW | 201144805 A | 12/2011 |
| TW | 201310016 A | 3/2013 |
| TW | 1438273 B | 5/2014 |
| WO | WO02/088702 A2 | 11/2002 |
| WO | WO2004/012848 A2 | 2/2004 |
| WO | WO2004/089810 A2 | 10/2004 |
| WO | WO2005/095963 A2 | 10/2005 |
| WO | WO2005/100541 A2 | 10/2005 |
| WO | WO2005/114132 A2 | 12/2005 |
| WO | WO2006/117541 A1 | 11/2006 |
| WO | WO2007/008609 A2 | 1/2007 |
| WO | WO2007/024701 A2 | 3/2007 |
| WO | WO2007/120241 A2 | 10/2007 |
| WO | WO2008/057366 A2 | 5/2008 |
| WO | WO2008/119066 A1 | 10/2008 |
| WO | WO2008/131048 A2 | 10/2008 |
| WO | WO2009/046125 A2 | 4/2009 |
| WO | WO2009/111723 A1 | 9/2009 |
| WO | WO2009/130694 A2 | 10/2009 |
| WO | WO2009/146143 A2 | 12/2009 |
| WO | WO2009/149467 A2 | 12/2009 |
| WO | WO2009/151505 A1 | 12/2009 |
| WO | WO2010/040851 A2 | 4/2010 |
| WO | WO2010/115167 A2 | 10/2010 |
| WO | WO2010/147078 A1 | 12/2010 |
| WO | WO2010/147942 A1 | 12/2010 |
| WO | WO2011/160430 A1 | 12/2011 |
| WO | WO2012/024658 A2 | 2/2012 |
| WO | WO2012/037030 A2 | 3/2012 |

(56) References Cited

FOREIGN PATENT DOCUMENTS

| | | |
|---|---|---|
| WO | WO2012/024658 A3 | 5/2012 |
| WO | WO2012/072823 A1 | 6/2012 |
| WO | WO2012/162779 A1 | 12/2012 |
| WO | WO2013/019491 A1 | 2/2013 |
| WO | WO2013/086502 A1 | 6/2013 |
| WO | WO2011/149032 A1 | 7/2013 |
| WO | WO2013/106588 A1 | 7/2013 |
| WO | WO2013/130714 A1 | 9/2013 |
| WO | WO2013/148745 A1 | 10/2013 |
| WO | WO2014/036915 A1 | 3/2014 |
| WO | WO2014/070873 A1 | 5/2014 |
| WO | WO2014/081840 A1 | 5/2014 |
| WO | WO2014/167858 A1 | 10/2014 |
| WO | WO2015/036364 A1 | 3/2015 |
| WO | WO2015/061497 A1 | 4/2015 |
| WO | WO2015/092064 A1 | 6/2015 |
| WO | WO2015/164846 A1 | 10/2015 |
| WO | WO2015/164847 A1 | 10/2015 |
| WO | WO2015/188171 A1 | 12/2015 |
| WO | WO2016/065339 A1 | 4/2016 |
| WO | WO2016/090295 A1 | 6/2016 |
| WO | WO2016/094715 A2 | 6/2016 |
| WO | WO2016/172454 A1 | 10/2016 |
| WO | WO2016/172621 A2 | 10/2016 |
| WO | WO2017/091601 A1 | 6/2017 |
| WO | WO2019/018801 A1 | 1/2019 |

OTHER PUBLICATIONS

Cahill, Brian P., et al. "Reversible electrowetting on silanized silicon nitride." Sensors and Actuators B: Chemical 144.2 (2010): 380-386. (Year: 2010).*

Schaler, Ethan, et al. "Toward fluidic microrobots using electrowetting." 2012 IEEE International Conference on Robotics and Automation. IEEE, 2012. (Year: 2012).*

CN102500436A_Chen (Machine translation) Jun. 20, 2012, 11 pages.

CN102671723A_Wang, Machine Translation, Sep. 19, 2012, 21 pages.

CN101275114A, Lou—Machine Translation, Oct. 1, 2008, 8 pages.

Core BLI Chip Reference—BL000062US as published 20140116881A1.

Core BLI Chip Reference—BL000092US as published 20140124370A1.

Core BLI Chip Reference—BL000142US as published 20150151307A1.

Core BLI Chip Reference—BL000153US as published 20150151298A1.

Core BLI Chip Reference—BL000162US as published 20150165436A1.

Core BLI Chip Reference—BL000192US as published 20160199837A1.

Core BLI Chip Reference—BL000372US as published 20160312165A1.

Core BLI Chip Reference—BL000912US as published 20160184821A1.

Core BLI Chip Reference—BL001394US as published 20180298318A1.

Core BLI Chip Reference—BL001553US as published 20190240665A1.

File History Lowe et al.; U.S. Appl. 17/005,116 [BL001223-USCON] entitled "Microfluidic apparatus having an optimized electrowetting surface and related systems and methods," filed Aug. 27, 2020 (Available as Jan. 6, 2022).

JP2004117073A_Univ Waseda_Aisaka—Machine Translation, Apr. 15, 2004, 15 pages.

JP2004117073A Aisaka_ENG Abstract.

KIPO computer-generated English language translation of KR 10-2012-0066100 Gwang-Seok Yang, patent published Jun. 22, 2012.

KIPO computer-generated English language translation of KR 201000008222A_Kyun; 10 pages.

TWI258456, Cheng—Machine Translation, Jul. 21, 2006, 11 pages.

WO2010147078, University of Tokyo, Machine Translation, Dec. 23, 2010; 12 pages.

Z Report_European Patent Office, Extended European Search Report for Application No. 17803724.8, dated Feb. 26, 2020, 15 pages.

Z Report_Written Opinion and Search Report in Singapore Patent Application No. 11201809539R, dated Mar. 31, 2020, 12 pages.

Z Report_International Searching Authority, International Search Report and Written Opinion for PCT/US16/28808, issued Sep. 1, 2016.

Z Report_International Search Report and Written Opinion from PCT/US2017/034832 dated Sep. 27, 2017, 20 pages.

Z Report_International Search Report and Written Opinion for PCT Application Serial No. PCT/US2015/027679 (dated Jul. 27, 2015), 11 pages.

Z Report_International Search Report and Written Opinion for PCT Application Serial No. PCT/US2015/027680 (dated Jun. 29, 2015), 9 pages.

Z Report_International Search Report and Written Opinion for PCT Application Serial No. PCT/US2016/059234 (dated Mar. 30, 2017), 20 pages.

Chen et al.; Regioselective Patterning ot Multiple SAMs and Applications in Surface-Guided Smart Microfluidics; ACS Applied Materials & Interfaces; 6(24); p. 21961-21969; Dec. 24, 2014.

Yu et al.; Flow-Through Functionalized PDMS Microfluidic Channels with Dextran Derivative for ELISAs; Lab on a Chip; 9(9); p. 1243-1247; Jan. 20, 2009.

Zhang et al.; "Click" Chemistry-Based Surface Modification of poly(dimethylsiloxane) for Protein Separation in a Microfluidic Chip; Electrophoresis; 31(18); p. 3129-3136; Sep. 20, 2010.

Banuls et al. Chemical surface modifications for the development of silicon-based label-free integrated optical (IO) biosensors: A review; ?Analytica Chimica Acta; 777; pp. 1-16 ; May 13, 2013.

Bellis; Advantages of RGD peptides for directing cell association with biomaterials; PMC manuscript of Biomaterials; 32; pp. 4205-4210; 12 pages (Author Manuscript); Jun. 2011.

Chiou et al.; Massively Parallel Manipulation of Single Cells and Microparticles Using Optical Images; Nature; (436) pp. 370-372; Jul. 2005.

Chung et al., Imaging single-cell signaling dynamics with a deterministic high-density single-cell trap array; Anal.Chem.; 83(18); pp. 7044-7052; 14 pages (Author Manuscript); Aug. 23, 2011.

Chow et al.; Peptide-based biopolymers in biomedicine and biotechnology; Materials Science and Engineering; 62(4); p. 125-155; Sep. 2008.

Dalvi et al.; Molecular Origins of Fluorocarbon Hydrophobicity; Proc Natl Acad Sci USA; 107(31); pp. 13603-13607; Aug. 2010.

Di Carlo et al.; Dynamic single-cell analysis for quantitative biology; Analytical Chemistry; pp. 7918-7925; Dec. 2006.

Drelich et al.,; The effect of drop (bubble) size on advancing and receding contact angles for heterogeneous and rough solid surfaces as observed with sessile-drop and captive-bubble techniques; J.Colloid &Interface Science; 179(1); pp. 37-50; Apr. 15, 1996.

Fan et al.; Cross-scale electric manipulation of cells and droplet by frequency-modulated dielectrophoresis and electrowetting; Lab on a Chip; 8(8); pp. 1325-1331; May 28, 2008.

Fuchs; Electronic sorting and recovery of single live cells from microlitre sized samples; Lab on a Chip: 6(1); pp. 121-126; (year of pub. sufficiently earlier than effective US filing date and any foreign priority date) 2006.

Furuta et al.; Wetting mode transition of nanoliter scale water droplets during evaporation on superhydrophobic surfaces with random roughness structure; Applied Surface Science; 258(7); pp. 2378-2383; Jan. 2012.

Furuta et al.; Wetting mode transition of water droplets by electrowetting on highly hydrophobic surfaces coated with two different silanes; Chemistry Letters; 41(1); pp. 23-25; Dec. 24, 2011.

Hsu et al.; Sorting of Differentiated Neurons Using Phototransistor-Based Optoelectronic Tweezers for Cell Replacement Therapy of Neurodegenerative Diseases; Transducers 2009 Conf.; pp. 1598-1601; Jun. 2009.

(56) References Cited

OTHER PUBLICATIONS

Huang et al.; Digital Microfluidic Dynamic Culture of Mammalian Embryos on an Electrowetting on Dielectric (EWOD) Chip; PLOS one; 10(5):e0124196, 15 pages; May 2015.
Huang et al.; Microfluidic integrated optoelectronic tweezers for single-cell preparation and analysis; Lab on a Chip; 13(18); pp. 3721-3727; (year of pub. sufficiently earlier than effective US filing date and any foreign priority date) 2013.
Hung et al.; Continuous Perfusion Microfluidic Cell Culture Array for High-Throughput Cell-Based Assays; Biotech and Bioengineering 89(1); pp. 1-8 ; Jan. 2005.
Iliescu et al.; Continuous field-flow separation of particle populations in a dielectrophoretic chip with three dimensional electrodes; Applied Physics Letters 90(23); pp. 234104, 4pages; Jun. 2007.
JONES; On the Relationship of Dielectrophoresis and Electrowetting; Langmuir; 18(11); pp. 4437-4443; May 28, 2002.
Lagally et al.; Parallel microfluidic arrays for SPRI detection; Proceedings of SPIE, vol. 7759, p. 77590J; Aug. 2010.
Lee et al.; Microfluidic Chemostat and Turbidostat with Flow Rate, Oxygen, and Temperature Control for Dynamic Continuous Culture; Lab Chip; 11(10); pp. 1730-1739, DOI: 10.1039/c1lc20019d, 10 pages; (Author Manuscript); (year of pub. sufficiently earlier than effective US filing date and any foreign priority date) 2011.
Lee et al.; Separation and sorting of cells in microsystems using physical principles; Journal of micromechanics and Microengineering; 26(1); doi: 10.10880960.1317/26/1/013003; 15 pages; Dec. 2015.
Lowe, Controlled Vapor Deposition of Azide-Terminated Siloxane Monolayers: A Platform for Tailoring Oxide Surfaces; (dissertation); Stanford University; 152 pgs.; published: Aug. 2011.
Mazurek et al.; Preparing mono-dispersed liquid core PDMS microcapsules from thiol-ene-epoxy-tailored flow-focusing microfluidic devices; RSC Advances; 5(20); pp. 15379-15386; Jan. 26, 2015.
Mehling et al.; Microfluidic Cell Culture, Current Opinion in Biotechnology; 25; pp. 95-102; Feb. 2014.
Nevill et al.; Integrated Microfluidic Cell Culture and Lysis on a Chip; Lab Chip; (12) pp. 1689-1695; Oct. 2007.
Papageorgiou et al.; Superior performance of multilayered fluoropolymer films in low voltage electrowetting: Journal of colloid and Interface Science; 368(1); pp. 592-598; 21 pages, (Author Manuscript); Feb. 2012.
Park et al.; Single-sided continuous optoelectrowetting (SCOEW) for droplet manipulation with light patterns; Lab on a Chip; 10 (13); pp. 1655-1661 (year of pub. sufficiently earlier than effective US filing date and any foreign priority date) 2010.
Pei et al.; Light-Actuated Digital Microfluidics for Largescale, Parallel Manipulation of Arbitrarily Sized Droplets; 2010 IEEE 23rd Int'l. Conf. on Micro. Electro. Mech. Sys.; 4 pages; Jan. 2010.
Ritchie et al.; Reconstitution of Membrane Proteins in Phospholipid Bilayer Nanodiscs; Methods Enzymol; 464; pp. 211-231; 23 pages; (Author Manuscript); Jan. 2009.
Somaweera et al.; "Generation of a Chemical Gradient Across an Array of 256 Cell Cultures in a Single Chip"; Analyst; 138(19); 14 pgs.; (Author Manuscript); Oct. 2013.
Srisuwan et al.; The Effects of Alkalized and Silanized Woven Sisal Fibers on Mechanical Properties of Natural Rubber Modified Epoxy Resin; Energy Pocedia; 56; pp. 19-25; Jan. 2014.
Swain et al.; Advances in embryo culture platforms: novel approaches to improve preimplantation embryo development through modifications of the microenvironment; Human Reproduction Update; 17(4); pp. 541-557; Mar. 31, 2011.
Valley et al.; A Unified Platform for Optoelectrowetting and Optoelectronic Tweezers; Lab Chip; 11(7); pp. 1292-1297; Jan. 2011.
Valley et al., An integrated platform for light-induced dielectrophoresis and electrowetting; 14 th International conference on Miniaturized Systems for Chemistry and Life Sciences; Groningen, The Netherlands; pp. 2098-2100, 3 pages; Oct. 3-7, 2010.
Valley et al.; Optoelectronic Tweezers as a Tool for Parallel Single-Cell Manipulation and Stimulation; IEEE Trans Biomed Circuits Syst.; 3(6); pp. 424-431; Dec. 2009.
Xu et al.; Recent Trends in Dielectrophoresis; Informacije MIDEM; 40(4) pp. 253-262; 2010.
Yi et al.; Microfluidics Technology for Manipulation and Analysis of Biological Cells; Anal Chim Acta; (560) pp. 1-23; Feb. 2006.
Young et al.; Fundamentals of Microfluidic Cell Culture in Controlled Microenvironments; cited as Chem Soc Rev.; Mar. 2010; 39(3); pp. 1036-1048; pub online Feb. 2010; dol: 10.1039/b909900); (24 pgs).
Zhang et al.;Azide Functional Monolayers Grafted to a Germanium Surface Model Substrates for ATR-IR Studies of interfacial Click Reactions; Langmuir ; 28(1); pp. 486-493; Dec. 8, 2011.
Zhang et al.; Controlled Aspiration and Positioning of Biological Cells in a Micropipette; IEEE Transactions on Biomedical Engineering: 59(4); pp. 1032-1040; Apr. 2012.
Lowe et al.; U.S. Appl. No. 16/920,365 entitled "Microfluidic Cell Culture," filed Jul. 2, 2020.
Chiou; Massively parallel optical manipulation of single cells, mirco- and nano-particles on optoelectronic devices; Iniversity of California at Berkeley; 147 pages (Dissertation); (year of pub. sufficiently earlier than effective US filing date and any foreign priority date) Fall 2005.
Jackson et al.; Microfluidic platform for detecting circulating leukemic cells: Analysis of minimum residual disease in acute myeloid leukemia as a case example. Chemical and Biological Microsystems Society;3 pages; retrieved from the internet (https://www.researchgate.net/profile/Matt-Jackson-9/publication/330262661_MICROFLUIDIC_PLATFORM_FOR_DETECTING_CIRCULATING_LEUKEMIC_CELLS_ANALYSIS_OF_MINIMUM_RESIDUAL_DISEASE_IN_ACUTE_MYELOID_LEUKEMIA_AS_A_CASE_EXAMPLE/links/5c365204458515a4c719a647/MICROFLUIDIC-PLATFORM-FOR-DETECTING-CIRCULATING-LEUKEMIC-CELLS-ANALYSIS-Of-MINIMUM-RESIDUAL-DISEASE-IN-ACUTE-MYELOID-LEUKEMIA-AS-A-CASE-EXAMPLE.pdf) on Dec. 21, 2023.
AITHAL; Development of self-assembled monolayer-based cell culture platform towards fabrication of a three dimensional bioreator; 183 pages; retrieved from the internet (https://digitalcommons.latech.edu/cgi/viewcontent.cgi?article=1565&context=dissertations); (Disseration); on Jan. 25, 2024.
Krishnamoorthy; Surface-initiated polymer brushes in the biomedical field: applications in membrane science, biosensing, cell culture, regenerative medicine and antibacterial coatings; Chemical Reviews; 114(21); p. 10976-11026; Nov. 2014.
Tehranirokh et al.; Microfluidic devices for cell cultivation and proliferation; Biomicrofluidics; 7(5); 051502; 33 pages; Sep. 2013.
Gouveia et al.; New self assembling multifunctional templates for the biofabrication and controlled self-release of cultured tissue; Tissue Engineering Part A: 21/11 and 12; pp. 1772-1784; Mar. 2015.

* cited by examiner

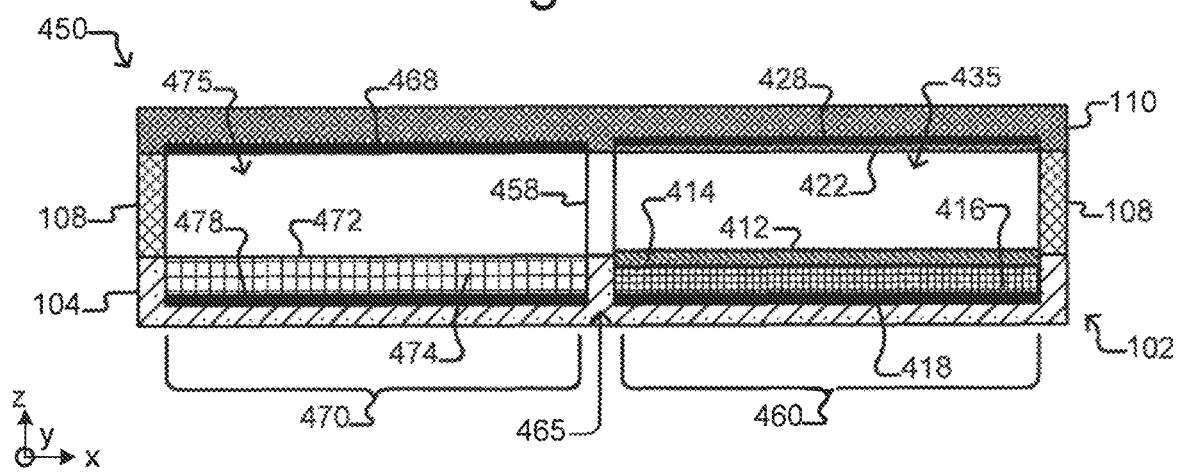
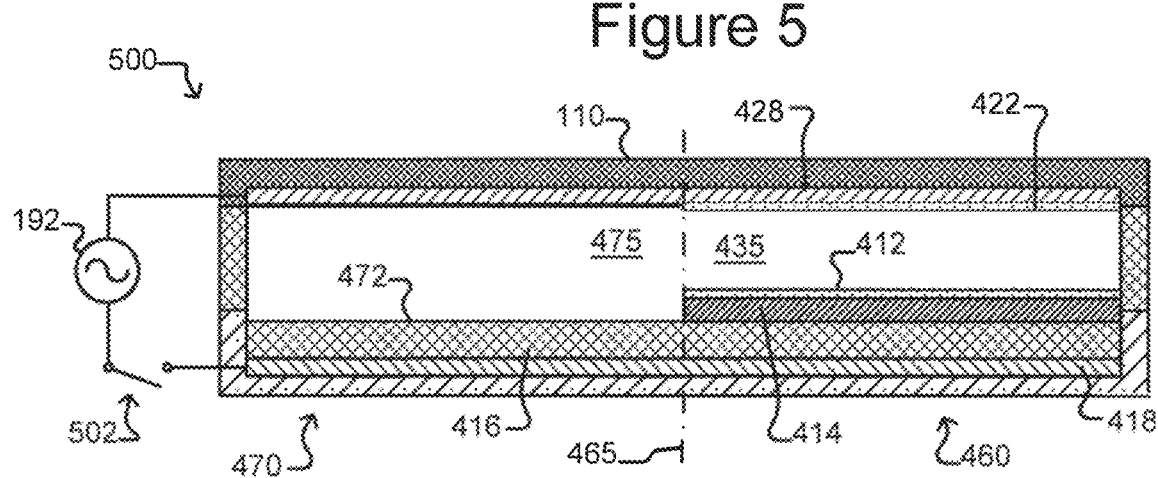

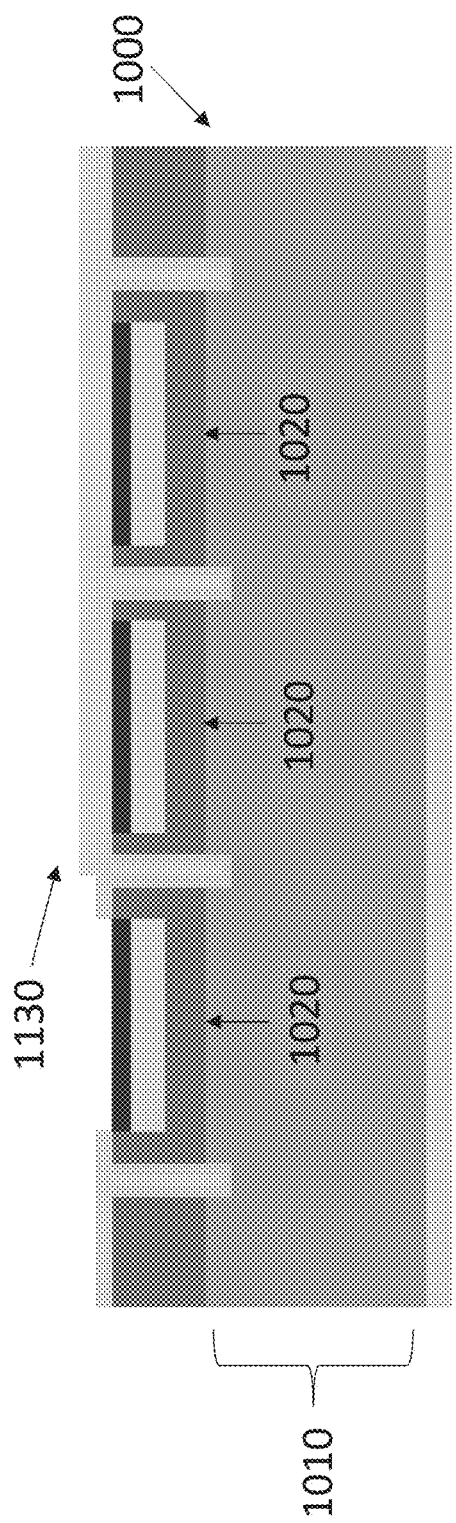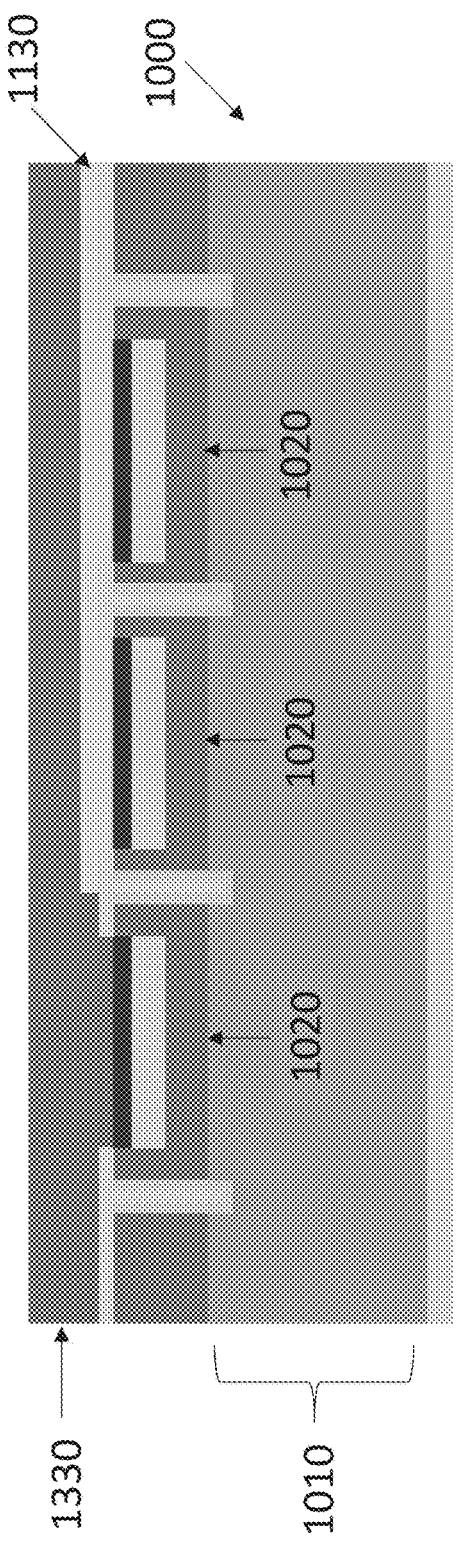

MICROFLUIDIC APPARATUS HAVING AN OPTIMIZED ELECTROWETTING SURFACE AND RELATED SYSTEMS AND METHODS

PRIORITY

This application is a continuation of U.S. patent application Ser. No. 15/336,768, filed Oct. 27, 2016, which claims priority from U.S. Provisional Application No. 62/246,605, filed Oct. 27, 2015, U.S. Provisional Application No. 62/247,725, filed Oct. 28, 2015, U.S. Provisional Application No. 62/342,131, filed May 26, 2016, and U.S. Provisional Application No. 62/410,238, filed Oct. 19, 2016, the contents of each of which are incorporated herein by reference in their entirety. This application is a continuation-in-part of U.S. patent application Ser. No. 15/135,707, filed Apr. 22, 2016, now U.S. Pat. No. 10,723,988, the contents of which are incorporated herein by reference in their entirety.

BACKGROUND

Micro-objects, such as biological cells, can be processed in microfluidic apparatuses. For example, droplets containing micro-objects or reagents can be moved around and merged within a microfluidic apparatus. Embodiments of the present invention are directed to improvements in microfluidic apparatuses that facilitate robust manipulation of droplets, allowing complex chemical and biological reactions to be precisely and reproducibly performed at small scale. Droplets can be moved and merged within a microfluidic apparatus by changing an effective wetting property of an electrowetting surface in the microfluidic apparatus. Such movements can facilitate workflows in which cells are processed to assess various cellular properties, optionally after culturing the cell within the microfluidic apparatus. Present solutions for electrowetting are extremely limited in nature and fail to scale or implement additional functionality. Consequently, a need exists for improved electrowetting surfaces, stable substrates for microfluidic applications, and integration of additional functionality (e.g., cellular growth and characterization prior to downstream processing made possible by electrowetting), all of which will facilitate additional medical research applications.

SUMMARY OF THE INVENTION

In one aspect, the invention provides a microfluidic device comprising an electrowetting configuration which includes a substrate having a droplet actuation surface, the droplet actuation surface comprising (or consisting of, or consisting essentially of) a hydrophobic layer (i.e., an outer hydrophobic layer) covalently bonded to the surface of an underlying dielectric layer (i.e., an inner dielectric layer). When the microfluidic device is operatively connected to a voltage source, an aqueous droplet resting upon or otherwise contacting the hydrophobic layer can be reliably and robustly wetted, and thereby moved, by an electrowetting force.

The microfluidic device can comprise a base that includes the substrate, and the substrate can further have at least one electrode (e.g., a first electrode) configured to be connected to the voltage source (e.g., an AC voltage source), the at least one electrode being electrically coupled to the inner dielectric layer. In some embodiments, the microfluidic device further comprises a cover and at least one spacing element. The substrate and the cover can be substantially parallel to one another and joined together by the spacing element to define an enclosure configured to hold a liquid medium. In such embodiments, the cover can include at least one electrode configured to be connected to the voltage source (e.g., the AC voltage source). In some embodiments, the microfluidic device can comprise a single-sided electrowetting configuration. In such embodiments, the microfluidic device need not include a cover. For example, the base can include the substrate and a first electrode configured to be connected to a voltage source (e.g., an AC voltage source), and the substrate can include a second electrode (e.g., a mesh electrode) configured to be connected to the voltage source.

In some embodiments, the outer hydrophobic layer comprises self-associating molecules covalently bonded to the inner dielectric layer so as to form a densely-packed hydrophobic monolayer. In some embodiments, the self-associating molecules of the hydrophobic monolayer each comprise a siloxane group. In other embodiments, the self-associating molecules of the hydrophobic monolayer each comprise a phosphonic acid group. The siloxane groups or the phosphonic acid groups can be covalently bonded to the surface of the inner dielectric layer. In some embodiments, the self-associating molecules of the hydrophobic monolayer each comprise a surface modifying ligand and a linking group that links, either directly or indirectly, the surface modifying ligand to the surface of the inner dielectric layer. The surface modifying ligand can be any surface modifying ligand disclosed herein. For example, the surface modifying ligand can comprise an aliphatic group, such as an alkane group. Thus, for example, the self-associating molecules of the hydrophobic monolayer can be alkyl-terminated siloxane or alkyl-terminated phosphonic acid molecules. The alkyl groups can include a chain (e.g., an unbranched chain) of at least 10 carbons (e.g., at least 14, 16, 18, 20, 22, or more carbons). In other embodiments, the surface modifying ligand can comprise a fluorine-substituted aliphatic group, such as a fluoroalkyl group. Thus, for example, the self-associating molecules can be fluoroalkyl-terminated siloxane or fluoroalkyl-terminated phosphonic acid molecules. The fluoroalkyl groups can include a chain (e.g., an unbranched chain) of at least 10 carbons (e.g., at least 14, 16, 18, 20, 22, or more carbons). In certain embodiments, the fluoroalkyl groups include one or more (e.g., at least 4, 6, 8, 10, 12, or more) perfluorinated carbons. For example, the fluoroalkyl groups can have the chemical formula $CF_3-(CF_2)m-(CH_2)n-$, wherein m is at least 2, n is at least 2, and m+n is at least 9. In some embodiments, the surface modifying ligand comprises an ether linkage between a first aliphatic group and a second aliphatic group. For example, the first aliphatic group can be an alkyl group and the second aliphatic group can be a fluoroalkyl group (e.g., a perfluoroalkyl group). In certain embodiments, the alkyl or fluoroalkyl group of the surface modifying ligand is unbranched. In some embodiments, the alkyl or fluoroalkyl group of the surface modifying ligand does not contain any cyclic structures.

In some embodiments, the outer hydrophobic layer of the substrate has a thickness of less than 5 nanometers (e.g., about 1.5 to 3.0 nanometers). In some embodiments, the outer hydrophobic layer of the substrate can be patterned such that select regions are relatively hydrophilic compared to the remainder of the outer hydrophobic layer.

In some embodiments, the inner dielectric layer of the substrate can comprise a first layer of dielectric material. For example, the inner dielectric layer can consist of a single layer of dielectric material. The first layer of dielectric material can comprise an oxide, such as a metal oxide layer (e.g., aluminum oxide, hafnium oxide, or the like). In certain embodiments, the first oxide layer is formed by atomic layer deposition (ALD). Alternatively, the inner dielectric layer can be a dielectric stack that comprises two or more layers of dielectric material. Thus, in certain embodiments, the inner dielectric layer can comprise a first layer of dielectric material and a second layer of dielectric material. The first layer of dielectric material can comprise an oxide, such as a metal oxide (e.g., aluminum oxide, hafnium oxide, or the like); and the second layer of dielectric material can comprise an oxide, such as silicon oxide, or a nitride, such as silicon nitride. In such embodiments, the first layer of dielectric material can have a first surface that contacts the second layer of dielectric material and an opposing surface to which the hydrophobic layer is covalently bound. In certain embodiment, the second layer of dielectric material can have a thickness of about 30 nm to about 100 nm, depending upon the type of dielectric material used. For example, the second layer of dielectric material can comprise silicon oxide and can have a thickness of about 30 nm to about 50 nm, or about 30 nm to about 40 nm. Alternatively, the second layer of dielectric material can comprise silicon nitride and can have a thickness of about 50 nm to about 100 nm, or about 80 nm to about 100 nm. In certain embodiments, the second layer of dielectric material is formed by ALD. In other embodiments, the second layer of dielectric material is formed a Plasma Enhanced Chemical Vapor Deposition (PECVD) technique. In certain embodiments, the first layer of dielectric material can have a thickness of about 10 nm to about 50 nm (e.g., about 10 nm to about 20 nm, about 15 nm to about 25 nm, about 20 nm to about 30 nm, about 25 nm to about 35 nm, about 30 nm to about 40 nm, about 35 nm to about 45 nm, about 40 nm to about 50 nm, or any range defined by two of the foregoing endpoints) and can be formed by ALD.

In yet other embodiments, the inner dielectric can comprise a third layer of dielectric material, with the third layer of dielectric material have a first surface that contact the first layer of dielectric material and an opposing surface that is covalently bonded to the hydrophobic layer. In such embodiments, the first layer of dielectric material can comprise an oxide, as described above (or elsewhere herein), and the second layer of dielectric material can comprise an oxide or a nitride, as described above (or elsewhere herein). In certain embodiments, the third layer of dielectric material can comprise an oxide, such as silicon dioxide or other dielectric materials that bond well to siloxane groups. In certain embodiments, the third layer of dielectric material is deposited by ALD. In certain embodiments, third layer of dielectric material has a thickness of about 2 nm to about 10 nm, or about 4 nm to about 6 nm.

Regardless of the number of layers that make up the inner dielectric layer, the inner dielectric layer can have a total thickness of about 40 nm to about 120 nm (e.g., about 40 nm to about 60 nm, about 50 nm to about 70 nm, about 60 nm to about 80 nm, about 70 nm to about 90 nm, about 80 nm to about 100 nm, about 90 nm to about 110 nm, about 100 nm to about 120 nm, or a range defined by any two of the foregoing endpoints). Likewise, the dielectric layer can have a impedance of about 50 kOhms to about 150 kOhms (e.g., about 50 kOhms to about 75 kOhms, about 75 kOhms to about 100 kOhms, about 100 kOhms to about 125 kOhms, about 125 kOhms to about 150 kOhms, or a range defined by any two of the foregoing endpoints).

In some embodiments, the substrate can further comprise a photoresponsive layer. The photoresponsive layer can have a first side that contacts the inner dielectric layer and a second side that contacts the at least one electrode. In certain embodiments, the photoresponsive layer can comprise hydrogenated amorphous silicon. In such embodiments, illuminating any of a plurality of regions of the photoresponsive layer with a beam of light can reduce the electrical impedance of the photoresponsive layer at the illuminated region(s). In other embodiments, the photoresponsive layer comprises a plurality of conductors, each conductor controllably connectable to the at least one electrode of the substrate via a phototransistor switch.

For embodiments in which the microfluidic device comprises a cover, a surface of the cover that faces inward toward the enclosure can include an inner layer and a hydrophobic layer (i.e., an outer hydrophobic layer) covalently bonded to the inner layer. Similar to the outer hydrophobic layer of the substrate, the outer hydrophobic layer of the cover can comprise self-associating molecules covalently bonded to the inner layer so as to form a densely-packed hydrophobic monolayer. Thus, the outer hydrophobic layer can comprise any of the self-associating molecules described above (or elsewhere herein) for the outer hydrophobic layer of the substrate. In some embodiments, the outer hydrophobic layer of the cover comprises the same self-associating molecules as the outer hydrophobic layer of the substrate. In other embodiments, the outer hydrophobic layer of the substrate has a different type (or types) of self-associating molecules as the outer hydrophobic layer of the substrate.

In some embodiments, the outer hydrophobic layer of the inward-facing surface of the cover has a thickness of less than 5 nanometers (e.g., about 1.5 to 3.0 nanometers). In some embodiments, the outer hydrophobic layer of the inward-facing surface of the cover can be patterned such that select regions are relatively hydrophilic compared to the remainder of the outer hydrophobic layer.

In some embodiments, the microfluidic device can include an enclosure having at least one microfluidic channel. In addition, the enclosure can include at least one microfluidic chamber (or sequestration pen) fluidically connected to the microfluidic channel. At least a portion of the substrate that defines the microchannel and/or the chamber can have an electrowetting configuration. The electrowetting configuration can be connected to a biasing potential and, while thus connected, change an effective wetting characteristic of any of a plurality of corresponding regions of the substrate surface (i.e., the droplet actuating surface). The wetting characteristic of the substrate surface can be changed sufficiently to move a liquid droplet across the substrate surface and between the microfluidic channel and the chamber.

In some embodiments, the chamber (or sequestration pen) can include a holding region (e.g., isolation region) configured to hold a liquid droplet, and one (or more) connection region that fluidically connects the holding region to the microfluidic channel. A first connection region can be configured to allow movement of the liquid droplet between the microfluidic channel and the chamber. When a second connection region is present, it can be configured to allow for fluid flow and pressure relief when a liquid droplet is moved between the microfluidic channel and the holding region. In some embodiments, the enclosure can further include a second microfluidic channel In such embodiments, the chamber can be connected to both the first microfluidic channel and the second microfluidic channel.

In some embodiments, the microfluidic channel(s) can have a height of about 30 to about 200 microns, or about 50 to about 150 microns, with the height measured in a direction normal to the direction of fluid flow through the channel In some embodiments, the microfluidic channel(s) has a width of about 50 to about 1000 microns, or about 100 to about 500 microns, with the width measured in a direction normal to the direction of fluid flow through the channel.

In some embodiments, the chamber (or sequestration pen) has a height that is substantially the same as the height of the microfluidic channel(s). For example, the chamber height can be about 30 to about 200 microns, or about 50 to about 150 microns. In some embodiments, the chamber (or holding pen) has a cross-sectional area of about 100,000 to about 2,500,000 square microns, or about 200,000 to about 2,000,000 square microns. In some embodiments, the connection region (first, second, etc.) has a height that is substantially the same as the height of the corresponding chamber and/or the microfluidic channel off of which the connection regions opens. In some embodiments, the connection region has a width of about 50 to about 500 microns, or about 100 to about 300 microns.

In some embodiments, the microfluidic device can further include a droplet generator. The droplet generator can be configured to selectively provide droplets of one or more liquid media (e.g., aqueous liquid media) into the enclosure or a microfluidic channel within the enclosure. The droplets can contain, for example, micro-objects, such as biological micro-objects (e.g., cells) or beads. Alternatively, or in addition, the droplets can contain reagents, such as lysis buffer, affinity reagents, detectable labels, enzymatic mixtures, etc.

In some embodiments, the microfluidic device includes a culture chamber (e.g., a sequestration pen) suitable for culturing biological micro-objects. The culture chamber can be located within the enclosure, and can be is connected to a microfluidic channel. When the culture chamber is located within the enclosure, the enclosure can include a perfusion microfluidic channel configured to flow fresh culture medium past the culture chamber such that nutrients in the fresh culture medium and waste products in the culture chamber can be exchanged (e.g., by diffusion of nutrients into the culture chamber and diffusion of waste products out into the culture medium). The perfusion channel can be separate from the microfluidic channel connected to the droplet generator.

In some embodiments, an electrowetting apparatus is integrated with an electro positioning apparatus. For example, in some embodiments, a microfluidic device can include a substrate having an electrowetting configuration and a portion of a substrate can further comprise a dielectrophoresis (DEP) configuration. Thus, the substrate can be monolithic. Alternatively, the microfluidic device or apparatus can include a first module or section having a first substrate that has a dielectrophoresis (DEP) configuration, and a second module or section having a second substrate that includes an electrowetting configuration. Such devices can be considered as having a duolithic substrate, and there can be a bridge between the first module or section and the second module or section that provides integration of the functionalities associated with each substrate and its particular configuration. The bridge can include tubing or the like that connects two otherwise discrete devices. Alternatively, the bridge can comprise a bonding agent that brings the substrates into close juxtaposition (e.g., within 2 mm, 1.5 mm, 1.0 mm, 0.5 mm, or less). In yet other alternatives, the bridge can be a non-functional region on a monolithic substrate, wherein the zone of non-functionality is where the substrate configuration switches from one configuration (e.g., an electrowetting configuration) to another configuration (e.g., a DEP configuration). Regardless of whether the microfluidic device has a monolithic or duolithic substrate (or even a multi-lithic substrate), each of the electrowetting configuration and the DEP configuration can be any such configuration known in the art or disclosed herein. For example, the electrowetting configuration can be an opto-electrowetting (OEW) configuration, an electrowetting on dielectric (EWOD) configuration, a single-sided electrowetting configuration, or the like. Similarly, the DEP configuration can be an optoelectronic tweezer (OET) configuration, such as provided by photoconductive substrate comprising a layer of amorphous silicon and/or an array of phototransistors, an array of electrodes controlled by phototransistors, an array of electrodes electrically actuated, or the like. In certain alternative embodiments, the substrate can comprise an electrowetting configuration but lack any additional configuration (e.g., lack a dielectrophoresis (DEP) configuration).

Consequently, in some embodiments, a single monolithic apparatus can combine the functionality of both apparatus.

In another aspect, the invention provides a method of manufacturing a microfluidic device of the invention. The method can include: bonding a spacing element (e.g., made from microfluidic circuit material) to an inner surface of a cover having at least one electrode configured to be connected to a voltage source; bonding the spacing element and cover to an inner dielectric surface of a substrate having at least one electrode configured to be connected to a voltage source; and forming, by vapor deposition, a hydrophobic layer on at least a portion of the inner surface of the cover and at least a portion of the inner dielectric surface of the substrate. In certain embodiments, the spacing element is sandwiched between the inner surface of the cover and the inner dielectric surface of the substrate such that the cover and the substrate are oriented substantially parallel to one another. The substrate, spacing element, and cover can collectively define an enclosure configured to hold a liquid medium. In certain embodiments, the hydrophobic layers are deposited on substantially all exposed regions of the inner surface of the cover and substantially all exposed regions of the inner dielectric surface of the substrate (i.e., on substantially all surfaces facing inward toward the enclosure). In certain embodiments, the hydrophobic layer is further deposited on surfaces of the spacing element that face inward toward the enclosure.

In certain embodiments, the hydrophobic layers comprise self-associating molecules covalently bound to the inner surface of the cover and the inner dielectric surface of the substrate, wherein the self-associating molecules form densely-packed monolayers. In some embodiments, the self-associating molecules deposited by vapor deposition each comprise a surface modifying ligand and a linking group that links, either directly or indirectly, the surface modifying ligand to the surface of the inner dielectric layer. Thus, the self-associating molecules can be any of the self-associating molecules described above or elsewhere herein.

In another aspect, the invention provides methods for processing materials, such as chemicals and/or biological materials, in a microfluidic apparatus. In certain embodiments, the methods comprise: filling an enclosure, or a portion thereof, of a microfluidic apparatus comprising a substrate having an electrowetting configuration, a cover, and a spacing element which together define the enclosure with a first liquid medium; applying an AC voltage potential between at least one electrode of the substrate and at least one electrode of the cover; introducing a first droplet of liquid medium into the enclosure, the liquid medium of the droplet being immiscible in the first liquid medium; and moving the first droplet to a desired location within the enclosure by applying an electrowetting force to the first droplet. The first liquid medium can comprise any of the first liquid mediums described herein, such as a silicone oil, a fluorinated oil, or a combination thereof, and the first droplet can comprise an aqueous medium.

In some embodiments, the methods can include dragging the first droplet from a first section of the enclosure, such as a microfluidic channel, into a second section of the enclosure, such as a chamber, or vice versa. The foregoing dragging can include changing an effective electrowetting characteristic of a region of the substrate surface that is in contact with and/or adjacent to the first droplet. Thus, filling the enclosure with the first liquid medium can comprise filling the microfluidic channel and chamber with the first liquid medium.

In some embodiments, the microfluidic apparatus includes a droplet generator. The methods can comprise generating the first droplet using the droplet generator. In addition, the droplet generator can introduce the first droplet into the enclosure. The generated droplets can have a volume of about 100 picoliters to 100 nanoliters, or about 1 to 50 nanoliters. In some embodiments, the first droplet can include a micro-object, such as a bead or a biological micro-object (e.g., a cell, vesicle, etc.), a cell secretion, or a reagent. The bead can have molecules having affinity for a material of interest, such as a cell secretion (e.g., an antibody) or other biomolecule (e.g., nucleic acid, such as DNA, genomic DNA, mitochondrial DNA, RNA, mRNA, miRNA, or any combination thereof). The droplet can include a single micro-object, such as a single biological cell, or multiple micro-objects. For example, the droplet can include two to twenty, or more, micro-objects, such as beads. In some embodiments, the droplet can include a reagent, such as a cell lysis buffer, a label (e.g., a fluorescently labeled reagent), a luminescent reagent, an enzymatic mixture, or the like.

In some embodiments, the methods further include introducing second, third, fourth, etc. droplets into the enclosure and moving the second, third, fourth, etc. droplet to a desired location within the enclosure by applying an electrowetting force to the droplet. The second droplet can be moved to a position proximal to the first droplet and then merged with the first droplet to form a first combined droplet; the third droplet can be moved to a position proximal to the first combined droplet and then merged with the first combined droplet to form a second combined droplet; the fourth droplet can be moved to a position proximal to the second combined droplet and then merged with the second combined droplet to form a third combined droplet; and so on. Each additional droplet can contain a fluidic medium that is immiscible in the first liquid medium but miscible with the liquid medium of the first droplet.

In some embodiments, the first droplet contains a biological cell and the second droplet contains a reagent. The reagent can be a cell lysis buffer that lyses the biological cell when the first and second droplets are merged. Alternatively, the reagent can be a fluorescent label (e.g., a fluorescently-labeled antibody or other affinity reagent) or a reagent used in a luminescence assay. The third droplet can contain a reagent, such as one or more (e.g., two to twenty) capture beads having affinity for a material of interest. For example, the material of interest can be an antibody or a nucleic acid, such as DNA, genomic DNA, mitochondrial DNA, RNA, mRNA, miRNA, or any combination thereof. Such capture beads can optionally be exported from the apparatus for subsequent analysis. The fourth droplet can, like the second and third droplets, contain a reagent, such as an enzymatic mixture suitable for performing a reaction, such as a reverse transcriptase reaction or a whole genome amplification reaction.

In some embodiments, the moving and merging of droplets involves using electrowetting force comprises changing an effective electrowetting characteristic of a region of the substrate surface proximal to the droplet(s) to thereby move or merge the droplets. In certain embodiments, changing an effective electrowetting characteristic of the substrate surface can include activating electrowetting electrodes at the region of the substrate surface proximal to the droplet(s). In certain embodiments, activating the electrowetting electrodes at the region of the substrate surface proximal to the droplet(s) involves directing a pattern of light onto the region of the substrate surface.

Additional aspects and embodiments of the invention will be evident from the drawings and the detailed description that follows.

BRIEF DESCRIPTION OF THE DRAWINGS

FIG. 4 illustrates an example of a microfluidic device having an EW configuration and a DEP configuration with a duolithic substrate.

FIG. 5 illustrates an example of a microfluidic device having an EW configuration and a DEP configuration with a monolithic substrate.

FIG. 6 presents a variation on the embodiment shown in FIG. 5, wherein each chamber that contains an aqueous medium is located directly across the channel with the hydrophobic medium from a corresponding chamber that contains hydrophobic medium.

FIGS. 10-18 provide vertical cross-sectional views of a substrate being processed in accordance with the method depicted in FIG. 9.

DETAILED DESCRIPTION OF THE INVENTION

Figure 1A:
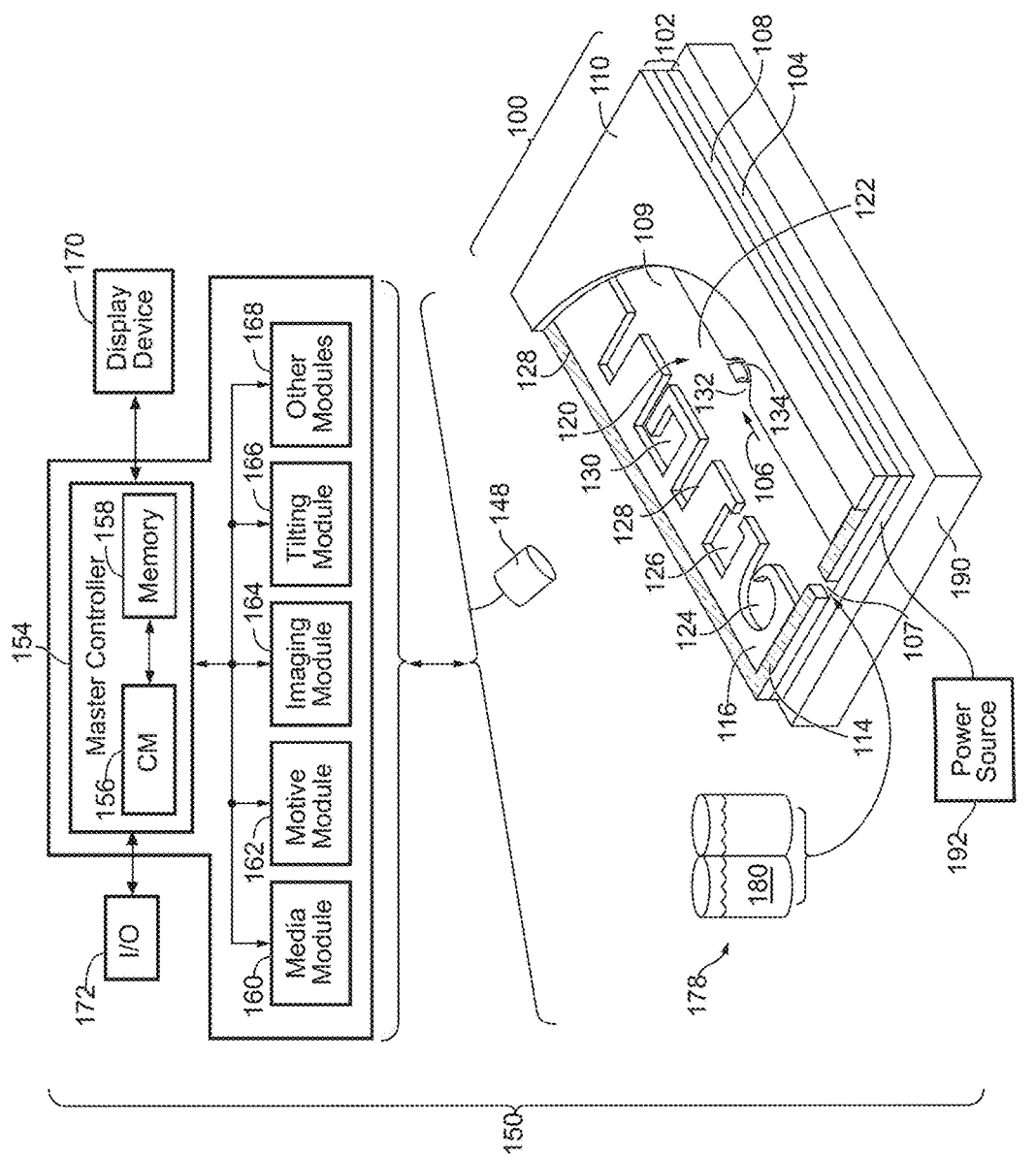
FIG. 1A illustrates a generalized microfluidic device and a system with associated control equipment for controlling and monitoring the microfluidic device, according to some embodiments of the invention.
Figure 1B:
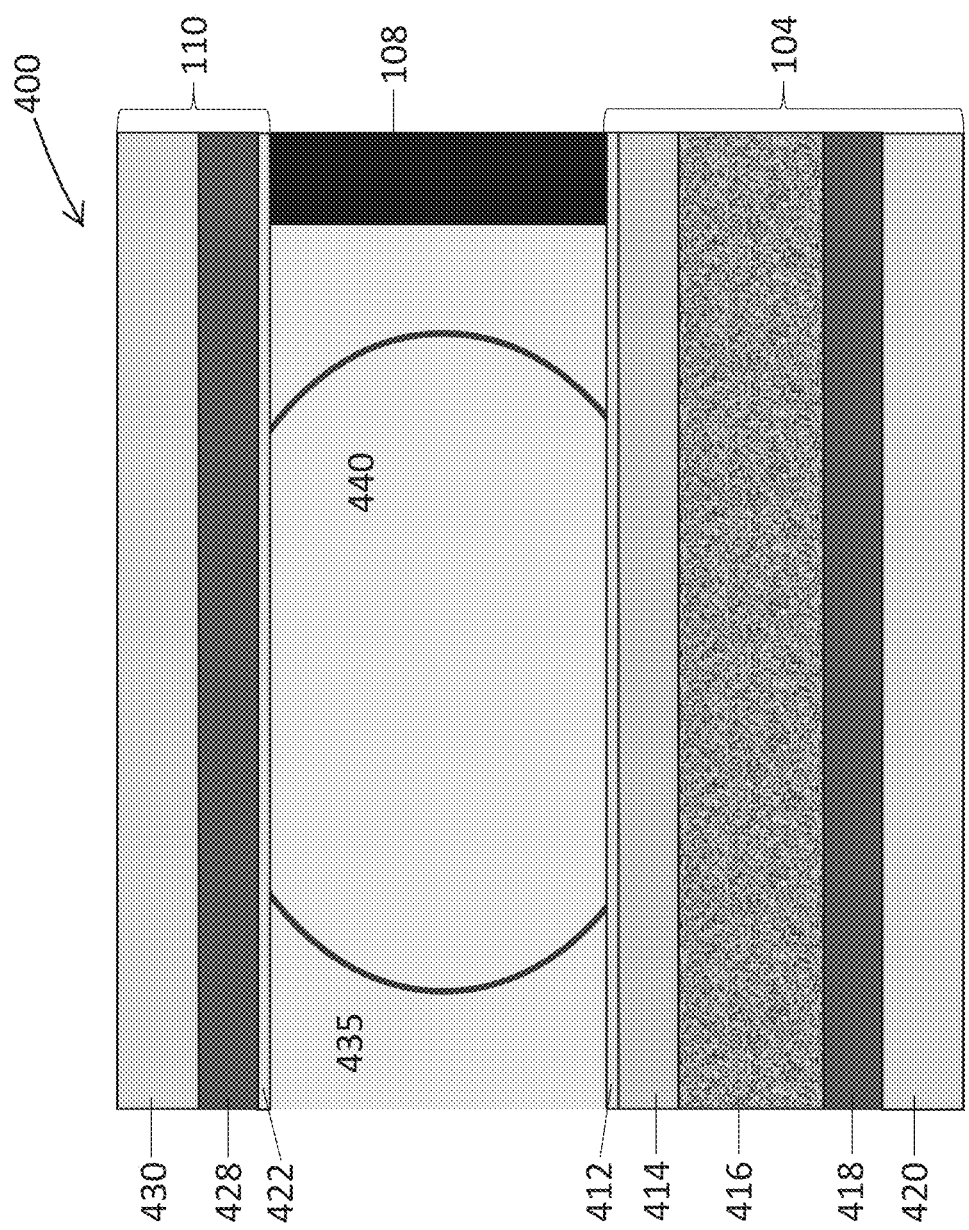
FIG. 1B is a vertical cross-sectional view of a microfluidic apparatus having a substrate, a cover, and a spacing element which together form an enclosure configured to hold a liquid medium and droplets of a liquid immiscible in the liquid medium. The substrate has an electrowetting configuration that allows the droplets to be manipulated within the enclosure.

This specification describes exemplary embodiments and applications of the invention. The invention, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. Also, unless the context dictates otherwise, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

The term "ones" means more than one.

As used herein, the term "plurality" can be 2, 3, 4, 5, 6, 7, 8, 9, 10, or more.

As used herein, the term "disposed" encompasses within its meaning "located."

As used herein, a "microfluidic device" or "microfluidic apparatus" is a device that includes one or more discrete microfluidic circuits configured to hold a fluid, each microfluidic circuit comprised of fluidically interconnected circuit elements, including but not limited to region(s), flow region(s), channel(s), chamber(s), and/or pen(s), and (for microfluidic device that include a cover) at least two ports configured to allow the fluid (and, optionally, micro-objects suspended in the fluid) to flow into and/or out of the microfluidic device. Typically, a microfluidic circuit of a microfluidic device will include at least one microfluidic channel and at least one chamber, and will hold a volume of fluid of less than about 1 mL, e.g., less than about 750, 500, 250, 200, 150, 100, 75, 50, 25, 20, 15, 10, 9, 8, 7, 6, 5, 4, 3, or 2 µL. In certain embodiments, the microfluidic circuit holds about 1-2, 1-3, 1-4, 1-5, 2-5, 2-8, 2-10, 2-12, 2-15, 2-20, 5-20, 5-30, 5-40, 5-50, 10-50, 10-75, 10-100, 20-100, 20-150, 20-200, 50-200, 50-250, or 50-300 µL.

As used herein, a "nanofluidic device" or "nanofluidic apparatus" is a type of microfluidic device having a microfluidic circuit that contains at least one circuit element configured to hold a volume of fluid of less than about 1 µL, e.g., less than about 750, 500, 250, 200, 150, 100, 75, 50, 25, 20, 15, 10, 9, 8, 7, 6, 5, 4, 3, 2, 1 nL or less. A nanofluidic device may comprise a plurality of circuit elements (e.g., at least 2, 3, 4, 5, 6, 7, 8, 9, 10, 15, 20, 25, 50, 75, 100, 150, 200, 250, 300, 400, 500, 600, 700, 800, 900, 1000, 1500, 2000, 2500, 3000, 3500, 4000, 4500, 5000, 6000, 7000, 8000, 9000, 10,000, or more). In certain embodiments, one or more (e.g., all) of the at least one circuit elements is configured to hold a volume of fluid of about 100 pL to 1 nL, 100 pL to 2 nL, 100 pL to 5 nL, 250 pL to 2 nL, 250 pL to 5 nL, 250 pL to 10 nL, 500 pL to 5 nL, 500 pL to 10 nL, 500 pL to 15 nL, 750 pL to 10 nL, 750 pL to 15 nL, 750 pL to 20 nL, 1 to 10 nL, 1 to 15 nL, 1 to 20 nL, 1 to 25 nL, or 1 to 50 nL. In other embodiments, one or more (e.g., all) of the at least one circuit elements is configured to hold a volume of fluid of about 20 nL to 200 nL, 100 to 200 nL, 100 to 300 nL, 100 to 400 nL, 100 to 500 nL, 200 to 300 nL, 200 to 400 nL, 200 to 500 nL, 200 to 600 nL, 200 to 700 nL, 250 to 400 nL, 250 to 500 nL, 250 to 600 nL, or 250 to 750 nL.

A "microfluidic channel" or "flow channel" as used herein refers to a flow region of a microfluidic device having a length that is significantly longer than both the horizontal and vertical dimensions. For example, the flow channel can be at least 5 times the length of either the horizontal or vertical dimension, e.g., at least 10 times the length, at least 25 times the length, at least 100 times the length, at least 200 times the length, at least 500 times the length, at least 1,000 times the length, at least 5,000 times the length, or longer. In some embodiments, the length of a flow channel is in the range of from about 50,000 microns to about 500,000 microns, including any range therebetween. In some embodiments, the horizontal dimension is in the range of from about 100 microns to about 1000 microns (e.g., about 150 to about 500 microns) and the vertical dimension is in the range of from about 25 microns to about 200 microns, e.g., from about 40 to about 150 microns. It is noted that a flow channel may have a variety of different spatial configurations in a microfluidic device, and thus is not restricted to a perfectly linear element. For example, a flow channel may include one or more sections having any of the following configurations: curve, bend, spiral, incline, decline, fork (e.g., multiple different flow paths), and any combination thereof. In addition, a flow channel may have different cross-sectional areas along its path, widening and constricting to provide a desired fluid flow therein.

As used herein, the term "obstruction" refers generally to a bump or similar type of structure that is sufficiently large so as to partially (but not completely) impede movement of target micro-objects between two different regions or circuit elements in a microfluidic device. The two different regions/circuit elements can be, for example, a microfluidic sequestration pen and a microfluidic channel, or a connection region and an isolation region of a microfluidic sequestration pen.

As used herein, the term "constriction" refers generally to a narrowing of a width of a circuit element (or an interface between two circuit elements) in a microfluidic device. The constriction can be located, for example, at the interface between a microfluidic sequestration pen and a microfluidic channel, or at the interface between an isolation region and a connection region of a microfluidic sequestration pen.

As used herein, the term "transparent" refers to a material which allows visible light to pass through without substantially altering the light as is passes through.

As used herein, the term "micro-object" refers generally to any microscopic object that may be isolated and collected in accordance with the present invention. Non-limiting examples of micro-objects include: inanimate micro-objects such as microparticles; microbeads (e.g., polystyrene beads, Luminex™ beads, or the like); magnetic beads; microrods; microwires; quantum dots, and the like; biological micro-objects such as cells (e.g., embryos, oocytes, ova, sperm cells, cells dissociated from a tissue, eukaryotic cells, protist cells, animal cells, mammalian cells, human cells, immunological cells, hybridomas, cultured cells, cells from a cell line, cancer cells, infected cells, transfected and/or transformed cells, reporter cells, prokaryotic cells, and the like); biological organelles; vesicles, or complexes; synthetic vesicles; liposomes (e.g., synthetic or derived from membrane preparations); lipid nanorafts (as described in Ritchie et al. (2009) "Reconstitution of Membrane Proteins in Phospholipid Bilayer Nanodiscs," Methods Enzymol., 464: 211-231), and the like; or a combination of inanimate micro-objects and biological micro-objects (e.g., microbeads attached to cells, liposome-coated micro-beads, liposome-coated magnetic beads, or the like). Beads may further have other moieties/molecules covalently or non-covalently attached, such as fluorescent labels, proteins, small molecule signaling moieties, antigens, or chemical/biological species capable of use in an assay.

As used herein, the term "maintaining (a) cell(s)" refers to providing an environment comprising both fluidic and gaseous components and, optionally a surface, that provides the conditions necessary to keep the cells viable and/or expanding.

A "component" of a fluidic medium is any chemical or biochemical molecule present in the medium, including solvent molecules, ions, small molecules, antibiotics, nucleotides and nucleosides, nucleic acids, amino acids, peptides, proteins, sugars, carbohydrates, lipids, fatty acids, cholesterol, metabolites, or the like.

As used herein in reference to a fluidic medium, "diffuse" and "diffusion" refer to thermodynamic movement of a component of the fluidic medium down a concentration gradient.

The phrase "flow of a medium" means bulk movement of a fluidic medium primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase "substantially no flow" refers to a rate of flow of a fluidic medium that, averaged over time, is less than the rate of diffusion of components of a material (e.g., an analyte of interest) into or within the fluidic medium. The rate of diffusion of components of such a material can depend on, for example, temperature, the size of the components, and the strength of interactions between the components and the fluidic medium.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the device.

A microfluidic (or nanofluidic) device can comprise "swept" regions and "unswept" regions. As used herein, a "swept" region is comprised of one or more fluidically interconnected circuit elements of a microfluidic circuit, each of which experiences a flow of medium when fluid is flowing through the microfluidic circuit. The circuit elements of a swept region can include, for example, regions, channels, and all or parts of chambers. As used herein, an "unswept" region is comprised of one or more fluidically interconnected circuit element of a microfluidic circuit, each of which experiences substantially no flux of fluid when fluid is flowing through the microfluidic circuit. An unswept region can be fluidically connected to a swept region, provided the fluidic connections are structured to enable diffusion but substantially no flow of media between the swept region and the unswept region. The microfluidic device can thus be structured to substantially isolate an unswept region from a flow of medium in a swept region, while enabling substantially only diffusive fluidic communication between the swept region and the unswept region. For example, a flow channel of a microfluidic device is an example of a swept region while an isolation region (described in further detail below) of a microfluidic device is an example of an unswept region.

As used herein, a "flow region" refers to one or more fluidically connected circuit elements (e.g. channel(s), region(s), chamber(s) and the like) that define, and are subject to, the trajectory of a flow of medium. A flow region is thus an example of a swept region of a microfluidic device. Other circuit elements (e.g., unswept regions) may be fluidically connected with the circuit elements that comprise the flow region without being subject to the flow of medium in the flow region.

As used herein, "alkyl" refers to a straight or branched hydrocarbon chain radical consisting solely of carbon and hydrogen atoms, containing no unsaturation, having from one to six carbon atoms (e.g., C1-C6 alkyl). Whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated. In some embodiments, it is a C1-C3 alkyl group. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), hexyl, and the like.

Unless stated otherwise specifically in the specification, an alkyl group may be optionally substituted by one or more substituents which independently are: aryl, arylalkyl, heteroaryl, heteroarylalkyl, hydroxy, halo, cyano, trifluoromethyl, trifluoromethoxy, nitro, trimethylsilanyl, —OR', —SR', —OC(O)—R', —N(R')2, —C(O)R', —C(O)OR', —OC(O)N(R')2, —C(O)N(R')2, —N(R')C(O)OR', —N(R')C(O)R', —N(R')C(O)N(R')2, N(R')C(NR')N(R')2, —N(R')S(O)tR' (where t is 1 or 2), —S(O)tOR' (where t is 1 or 2), —S(O)tN(R')2 (where t is 1 or 2), or PO3(R')2 where each R' is independently hydrogen, alkyl, fluoroalkyl, aryl, aralkyl, heterocycloalkyl, or heteroaryl.

As referred to herein, a fluorinated alkyl moiety is an alkyl moiety having one or more hydrogens of the alkyl moiety replaced by a fluoro substituent. A perfluorinated alkyl moiety has all hydrogens attached to the alkyl moiety replaced by fluoro substituents.

As referred to herein, a "halo" moiety is a bromo, chloro, or fluoro moiety.

As referred to herein, an "olefinic" compound is an organic molecule which contains an "alkene" moiety. An alkene moiety refers to a group consisting of at least two carbon atoms and at least one carbon-carbon double bond. The non-alkene portion of the molecule may be any class of organic molecule, and in some embodiments, may include alkyl or fluorinated (including but not limited to perfluorinated) alkyl moieties, any of which may be further substituted.

As used herein, a "densely packed hydrophobic monolayer" refers to a single layer of hydrophobic molecules that are packed sufficiently close together so as to resist intercalation and/or intrusion of polar molecules, such as water, ions, and other charged species.

As used herein: "μm" (or "um") means micrometer; "μm3" means cubic micrometer; "pL" means picoliter, "nL" means nanoliter; and "μL" (or "uL") means microliter.

Methods of loading. Loading of micro-objects, such as biological micro-objects and/or beads, into different regions of a microfluidic device can involve the use of fluid flow, gravity, a dielectrophoresis (DEP) force, an electrowetting force, a magnetic force, or any combination thereof as described herein. The DEP force can be generated optically, such as by an optoelectronic tweezers (OET) configuration and/or electrically, such as by activation of electrodes/electrode regions in a temporal/spatial pattern. Similarly, the electrowetting force may be provided optically, such as by an opto-electro wetting (OEW) configuration and/or electrically, such as by activation of electrodes/electrode regions in a temporal spatial pattern.

Microfluidic devices and systems for operating and observing such devices. FIG. 1A illustrates a generalized example of a microfluidic device 100 and a system 150 which can be used to control the microfluidic device 100 and the movement of micro-objects and/or droplet therein. A perspective view of the microfluidic device 100 is shown having a partial cut-away of its cover 110 to provide a partial view into the microfluidic device 100. The microfluidic device 100 generally comprises a microfluidic circuit 120 comprising a flow region 106 through which a fluidic medium 180 can flow, optionally carrying one or more micro-objects (not shown) into and/or through the microfluidic circuit 120. Although a single microfluidic circuit 120 is illustrated in FIG. 1A, suitable microfluidic devices can include a plurality (e.g., 2 or 3) of such microfluidic circuits. Regardless, the microfluidic device 100 can be configured to be a nanofluidic device. In the embodiment illustrated in FIG. 1A, the microfluidic circuit 120 comprises a plurality of microfluidic sequestration pens 124, 126, 128, and 130, each having a single opening in fluidic communication with flow region 106. As discussed further below, the microfluidic sequestration pens comprise various features and structures that have been optimized for retaining micro-objects in the microfluidic device, such as microfluidic device 100, even when a medium 180 is flowing through the flow region 106. Before turning to the foregoing, however, a brief description of microfluidic device 100 and system 150 is provided.

As generally illustrated in FIG. 1A, the microfluidic circuit 120 is defined by an enclosure 102. Although the enclosure 102 can be physically structured in different configurations, in the example shown in FIG. 1A the enclosure 102 is depicted as comprising a support structure 104 (e.g., a base), a microfluidic circuit structure 108, and a cover 110. In certain embodiments, however, the enclosure 102 may lack the cover 110 and the microfluidic circuit 120 may be defined by the support structure 104 and the microfluidic circuit structure 108. The support structure 104, the microfluidic circuit structure 108, and (optionally) the cover 110 can be attached to each other. For example, the microfluidic circuit structure 108 can be disposed on an inner surface 109 of the support structure 104, and the cover 110 can be disposed over the microfluidic circuit structure 108. Together with the support structure 104 and (optionally) the cover 110, the microfluidic circuit structure 108 can define the elements of the microfluidic circuit 120.

The support structure 104 can be at the bottom and the cover 110 at the top of the microfluidic circuit 120, as illustrated in FIG. 1A. Alternatively, the support structure 104 and the cover 110 can be configured in other orientations. For example, the support structure 104 can be at the top and the cover 110 at the bottom of the microfluidic circuit 120. Regardless, there can be one or more ports 107 each comprising a passage into or out of the enclosure 102. Examples of a passage include a valve, a gate, a pass-through hole, or the like. As illustrated, port 107 is a pass-through hole created by a gap in the microfluidic circuit structure 108. However, the port 107 can be situated in other components of the enclosure 102, such as the cover 110. Only one port 107 is illustrated in FIG. 1A, but the microfluidic circuit 120 can have two or more ports 107. For example, there can be a first port 107 that functions as an inlet for fluid entering the microfluidic circuit 120, and there can be a second port 107 that functions as an outlet for fluid exiting the microfluidic circuit 120. Whether a port 107 function as an inlet or an outlet can depend upon the direction that fluid flows through flow region 106.

The support structure 104 can comprise one or more electrodes (not shown) and a substrate or a plurality of interconnected substrates. The substrate can be any suitable substrate known in the art. For example, the support structure 104 can comprise one or more semiconductor substrates, each of which is electrically connected to at least one of the one or more electrodes (e.g., all or a subset of the semiconductor substrates can be electrically connected to a single electrode). Alternatively, the support structure 104 can comprise a printed circuit board assembly ("PCBA") which comprises the one or more electrodes. In still other embodiments, the support structure 104 can comprise a substrate (e.g., a semiconductor substrate) which is mounted on a PCBA.

The microfluidic circuit structure 108 can define circuit elements of the microfluidic circuit 120. Such circuit elements can comprise spaces or regions that can be fluidly interconnected when microfluidic circuit 120 is filled with fluid, such as flow regions (which may include or be one or more flow channels), chambers, pens, traps, and the like. In the microfluidic circuit 120 illustrated in FIG. 1A, the microfluidic circuit structure 108 comprises a frame 114 and a microfluidic circuit material 116. The frame 114 can partially or completely enclose the microfluidic circuit material 116. The frame 114 can be, for example, a relatively rigid structure substantially surrounding the microfluidic circuit material 116. For example, the frame 114 can comprise a metal material. Alternatively, the microfluidic circuit structure 108 can lack a frame. For example, the microfluidic circuit structure 108 can consist of or consist essentially of the microfluidic circuit material 116.

The microfluidic circuit material 116 can be patterned with cavities or the like to define circuit elements and interconnections of the microfluidic circuit 120. The microfluidic circuit material 116 can comprise a flexible material, such as a flexible polymer (e.g. rubber, plastic, elastomer, silicone, polydimethylsiloxane ("PDMS"), or the like), which can be gas permeable. Other examples of materials that can compose microfluidic circuit material 116 include molded glass, an etchable material such as silicone (e.g. photo-patternable silicone or "PPS"), photo-resist (e.g., SU8), or the like. In some embodiments, such materials—and thus the microfluidic circuit material 116—can be rigid and/or substantially impermeable to gas. Regardless, the microfluidic circuit material 116 can be disposed on the support structure 104 and (optionally) inside the frame 114.

The cover 110 can be an integral part of the microfluidic circuit material 116 and/or the frame 114. Alternatively, the cover 110 can be a structurally distinct element, as illustrated in FIG. 1A. The cover 110 can comprise the same or different materials as the frame 114 and/or the microfluidic circuit material 116. Similarly, the support structure 104 can be a separate structure from the microfluidic circuit material 116 or the frame 114, as illustrated, or an integral part of the microfluidic circuit material 116 or frame 114. Likewise, the microfluidic circuit material 116 and the frame 114, if present, can be separate structures as shown in FIG. 1A or integral portions of the same structure.

In some embodiments, the cover 110 can comprise a rigid material. The rigid material may be glass or a material with similar properties. In some embodiments, the cover 110 can comprise a deformable material. The deformable material can be a polymer, such as PDMS. In some embodiments, the cover 110 can comprise both rigid and deformable materials. For example, one or more portions of cover 110 (e.g., one or more portions positioned over sequestration pens 124, 126, 128, 130) can comprise a deformable material that interfaces with rigid materials of the cover 110. In some embodiments, the cover 110 can further include one or more electrodes. The one or more electrodes can comprise a conductive oxide, such as indium-tin-oxide (ITO), which may be coated on glass or a similarly insulating material. Alternatively, the one or more electrodes can be flexible electrodes, such as single-walled nanotubes, multi-walled nanotubes, nanowires, clusters of electrically conductive nanoparticles, or combinations thereof, embedded in a deformable material, such as a polymer (e.g., PDMS). Flexible electrodes that can be used in microfluidic devices have been described, for example, in U.S. 2012/0325665 (Chiou et al.), the contents of which are incorporated herein by reference. In some embodiments, the cover 110 can be modified (e.g., by coating or conditioning all or part of a surface that faces inward toward the microfluidic circuit 120) to support droplet movement and/or cell adhesion, cell viability and/or cell growth. The modification may include a coating of a synthetic or natural polymer or a conditioned surface having covalently bound molecules (e.g., self-associating molecules). In some embodiments, the cover 110 and/or the support structure 104 can be transparent to light. The cover 110 may also include at least one material that is gas permeable (e.g., PDMS or PPS).

FIG. 1A also shows a system 150 for operating and controlling microfluidic devices, such as microfluidic device 100. System 150 includes an electrical power source 192, an imaging device 194 (not shown, but may be part of imaging module 164), and a tilting device 190 (not shown, but may be part of tilting module 166).

The electrical power source 192 can provide electric power to the microfluidic device 100 and/or tilting device 190, providing biasing voltages or currents as needed. The electrical power source 192 can, for example, comprise one or more alternating current (AC) and/or direct current (DC) voltage or current sources. The imaging device 194 can comprise a device, such as a digital camera, for capturing images inside microfluidic circuit 120. In some instances, the imaging device 194 further comprises a detector having a fast frame rate and/or high sensitivity (e.g. for low light applications). The imaging device 194 can also include a mechanism for directing stimulating radiation and/or light beams into the microfluidic circuit 120 and collecting radiation and/or light beams reflected or emitted from the microfluidic circuit 120 (or micro-objects contained therein). The emitted light beams may be in the visible spectrum and may, e.g., include fluorescent emissions. The reflected light beams may include reflected emissions originating from an LED or a wide spectrum lamp, such as a mercury lamp (e.g. a high pressure mercury lamp) or a Xenon arc lamp. As discussed with respect to FIG. 3B, the imaging device 194 may further include a microscope (or an optical train), which may or may not include an eyepiece.

System 150 further comprises a tilting device 190 configured to rotate a microfluidic device 100 about one or more axes of rotation. In some embodiments, the tilting device 190 is configured to support and/or hold the enclosure 102 comprising the microfluidic circuit 120 about at least one axis such that the microfluidic device 100 (and thus the microfluidic circuit 120) can be held in a level orientation (i.e. at 0° relative to x- and y-axes), a vertical orientation (i.e. at 90° relative to the x-axis and/or the y-axis), or any orientation therebetween. The orientation of the microfluidic device 100 (and the microfluidic circuit 120) relative to an axis is referred to herein as the "tilt" of the microfluidic device 100 (and the microfluidic circuit 120). For example, the tilting device 190 can tilt the microfluidic device 100 at 0.1°, 0.2°, 0.3°, 0.4°, 0.5°, 0.6°, 0.7°, 0.8°, 0.9°, 1°, 2°, 3°, 4°, 5°, 10°, 15°, 20°, 25°, 30°, 35°, 40°, 45°, 50°, 55°, 60°, 65°, 70°, 75°, 80°, 90°, or any degree therebetween relative to the x-axis or the y-axis. The level orientation (and thus the x- and y-axes) is defined as normal to a vertical axis defined by the force of gravity. The tilting device can also tilt the microfluidic device 100 (and the microfluidic circuit 120) to any degree greater than 90° relative to the x-axis and/or y-axis, or tilt the microfluidic device 100 (and the microfluidic circuit 120) 180° relative to the x-axis or the y-axis in order to fully invert the microfluidic device 100 (and the microfluidic circuit 120). Similarly, in some embodiments, the tilting device 190 tilts the microfluidic device 100 (and the microfluidic circuit 120) about an axis of rotation defined by flow region 106/channel 122 or some other portion of microfluidic circuit 120.

In some instances, the microfluidic device 100 is tilted into a vertical orientation such that the flow region 106/channel 122 is positioned above or below one or more sequestration pens. The term "above" as used herein denotes that the flow region 106/channel 122 is positioned higher than the one or more sequestration pens on a vertical axis defined by the force of gravity (i.e. an object in a sequestration pen above a flow region 106/channel 122 would have a higher gravitational potential energy than an object in the flow region/channel). The term "below" as used herein denotes that the flow region 106/channel 122 is positioned lower than the one or more sequestration pens on a vertical axis defined by the force of gravity (i.e. an object in a sequestration pen below a flow region 106/channel 122 would have a lower gravitational potential energy than an object in the flow region/channel).

In some instances, the tilting device 190 tilts the microfluidic device 100 about an axis that is parallel to the flow region 106/channel 122. Moreover, the microfluidic device 100 can be tilted to an angle of less than 90° such that the flow region 106/channel 122 is located above or below one or more sequestration pens without being located directly above or below the sequestration pens. In other instances, the tilting device 190 tilts the microfluidic device 100 about an axis perpendicular to the flow region 106/channel 122. In still other instances, the tilting device 190 tilts the microfluidic device 100 about an axis that is neither parallel nor perpendicular to the flow region 106/channel 122.

System 150 can further include a media source 178. The media source 178 (e.g., a container, reservoir, or the like) can comprise multiple sections or containers, each for holding a different fluidic medium 180. Thus, the media source 178 can be a device that is outside of and separate from the microfluidic device 100, as illustrated in FIG. 1A. Alternatively, the media source 178 can be located in whole or in part inside the enclosure 102 of the microfluidic device 100. For example, the media source 178 can comprise reservoirs that are part of the microfluidic device 100.

FIG. 1A also illustrates simplified block diagram depictions of examples of control and monitoring equipment 152 that constitute part of system 150 and can be utilized in conjunction with a microfluidic device 100. As shown, examples of such control and monitoring equipment 152 include a master controller 154, a media module 160 for controlling the media source 178, a motive module 162 for controlling movement and/or selection of micro-objects and/or medium (e.g., droplets of medium) in the microfluidic circuit 120, an imaging module 164 for controlling an imaging device 194 (e.g., a camera, microscope, light source or any combination thereof) for capturing images (e.g., digital images), and a tilting module 166 for controlling a tilting device 190. The control equipment 152 can also include other modules 168 for controlling, monitoring, or performing other functions with respect to the microfluidic device 100. As shown, the equipment 152 can be operatively coupled with (or further include) a display device 170 and an input/output device 172.

The master controller 154 can comprise a control module 156 and a digital memory 158. The control module 156 can comprise, for example, a digital processor configured to operate in accordance with machine executable instructions (e.g., software, firmware, source code, or the like) stored as non-transitory data or signals in the memory 158. Alternatively, or in addition, the control module 156 can comprise hardwired digital circuitry and/or analog circuitry. The media module 160, motive module 162, imaging module 164, tilting module 166, and/or other modules 168 can be similarly configured. Thus, functions, processes acts, actions, or steps of a process discussed herein as being performed with respect to the microfluidic device 100 or any other microfluidic apparatus can be performed by any one or more of the master controller 154, media module 160, motive module 162, imaging module 164, tilting module 166, and/or other modules 168 configured as discussed above. Similarly, the master controller 154, media module 160, motive module 162, imaging module 164, tilting module 166, and/or other modules 168 may be communicatively coupled to transmit and receive data used in any function, process, act, action or step discussed herein.

The media module 160 controls the media source 178. For example, the media module 160 can control the media source 178 to input a selected fluidic medium 180 into the enclosure 102 (e.g., through an inlet port 107). The media module 160 can also control removal of media from the enclosure 102 (e.g., through an outlet port (not shown)). One or more media can thus be selectively input into and removed from the microfluidic circuit 120. The media module 160 can also control the flow of fluidic medium 180 in the flow region 106/channel 122 inside the microfluidic circuit 120. For example, in some embodiments the media module 160 stops the flow of media 180 in the flow region 106/channel 122 and through the enclosure 102 prior to the loading of a micro-object or a bead into a sequestration pen (e.g., using gravity, electrowetting (EW) force, dielectrophoresis (DEP) force, or a combination thereof).

The motive module 162 can be configured to control selection, trapping, and movement of micro-objects and/or droplets of medium in the microfluidic circuit 120. As discussed in detail herein, the enclosure 102 can comprise an electrowetting (EW) configuration, such as an opto-electrowetting (OEW) configuration, an electrowetting on dielectric (EWOD) configuration, a single-sided electrowetting configuration, or the like. In certain embodiments, the enclosure 102 can further comprise a dielectrophoresis (DEP) configuration, such as an optoelectronic tweezer (OET) configuration, an electrically actuated DEP configuration, and the like. The motive module 162 can control the activation of electrodes and/or transistors (e.g., phototransistors) comprised by such EW and/or DEP configurations to select and move micro-objects and/or droplets of medium in the flow region 106/channel 122 and/or sequestration pens 124, 126, 128, 130.

The imaging module 164 can control the imaging device 194 (not shown). For example, the imaging module 164 can receive and process image data from the imaging device

194. Image data from the imaging device 194 can comprise any type of information captured by the imaging device 194 (e.g., the presence or absence of micro-objects, droplets of medium, accumulation of label, such as fluorescent label, etc.). Using the information captured by the imaging device 194, the imaging module 164 can further calculate the position of objects (e.g., micro-objects, droplets of medium, or the like) and/or the rate of motion of such objects within the microfluidic device 100.

The tilting module 166 can control the tilting motions of tilting device 190 (not shown). In addition, the tilting module 166 can control the tilting rate and timing, for example, to optimize transfer of micro-objects to the one or more sequestration pens via gravitational forces. The tilting module 166 is communicatively coupled with the imaging module 164 to receive data describing the motion of micro-objects and/or droplets of medium in the microfluidic circuit 120. Using this data, the tilting module 166 may adjust the tilt of the microfluidic circuit 120 in order to adjust the rate at which micro-objects and/or droplets of medium move in the microfluidic circuit 120. The tilting module 166 may also use this data to iteratively adjust the position of a micro-object and/or droplet of medium in the microfluidic circuit 120.

In the example shown in FIG. 1A, the microfluidic circuit 120 is illustrated as comprising a single flow region 106 consisting essentially of microfluidic channel 122. Each of sequestration pens 124, 126, 128, and 130 comprises a single opening to flow region 106/channel 122, but otherwise is enclosed such that the pens can substantially isolate micro-objects inside the pen from micro-objects and/or fluidic medium 180 in the flow region 106/channel 122 or in other pens. The walls of the sequestration pen can extend from the inner surface 109 of the base to the inside surface of the cover 110 to thereby facilitate such isolation. The opening of the pen to the flow region 106/channel 122 can be oriented at an angle with respect to the flow of fluidic medium 180 in flow region 106/channel 122 such that the flow of fluidic medium 180 is not directed into the pens. The flow may be, for example, tangential or orthogonal to the plane of the opening of the pen. In some instances, pens 124, 126, 128, and/or 130 are configured to physically corral one or more micro-objects within the microfluidic circuit 120. Sequestration pens in accordance with the present invention can comprise various shapes, surfaces and features that are optimized for use with EW, OEW, DEP, and/or OET forces, fluid flow, and/or gravitational forces, as will be discussed in detail below.

The microfluidic circuit 120 may comprise any number of microfluidic sequestration pens. Although five sequestration pens are shown, microfluidic circuit 120 may have fewer or more sequestration pens. As shown, microfluidic sequestration pens 124, 126, 128, and 130 of microfluidic circuit 120 each comprise differing features and shapes which may provide one or more benefits useful for the manipulation of micro-objects and/or droplets of fluidic medium with the microfluidic device 100. Thus, in some embodiments, the microfluidic circuit 120 may comprise a plurality of microfluidic sequestration pens, wherein two or more of the sequestration pens comprise differing structures and/or features which provide differing benefits. In some embodiments, however, the microfluidic circuit 120 comprises a plurality of identical microfluidic sequestration pens. Microfluidic devices useful the manipulation of micro-objects and/or droplets of medium may include any of the sequestration pens 124, 126, 128, and 130, or variations thereof, including pens configured like those shown in FIGS. 2B, 2C, 2D, 2E and 2F, as discussed below.

In the embodiment illustrated in FIG. 1A, a single flow region 106 is shown. However, other embodiments of microfluidic device 100 may contain multiple flow regions 106, each configured to provide a separate path for fluid to flow through the microfluidic device 100. The microfluidic circuit 120 comprises an inlet valve or port 107 in fluid communication with the flow region 106, whereby fluidic medium 180 can access flow region 106/channel 122 via the inlet port 107. In some instances, the flow region 106 comprises a single flow path. In other instances, the flow region 106 comprises a plurality of flow paths (e.g., 2, 3, 4, 5, 6, or more), each of which may comprise a microchannel (e.g., like channel 122). Two or more (e.g., all) of the plurality of flow paths may be substantially parallel to one another. For example, flow region 106 can split into a plurality of parallel channels (e.g., like channel 122). In certain embodiments, the flow region 106 (and one or more channels comprised by the flow region) is arranged in a zigzag pattern, whereby the flow region 106 travels across the microfluidic device 100 two or more times in alternating directions. In some instances, the fluidic medium within each flow region 106 flows in at least one of a forward or reverse direction. In some instances, a plurality of sequestration pens is configured (e.g., relative to a flow region 106/channel 122) such that the sequestration pens can be loaded with target micro-objects in parallel.

In some embodiments, microfluidic circuit 120 further comprises one or more micro-object traps 132. The traps 132 are generally formed in a wall forming the boundary of a flow region 106/channel 122, and may be positioned opposite an opening of one or more of the microfluidic sequestration pens 124, 126, 128, and 130. In some embodiments, the traps 132 are configured to receive or capture a single micro-object from the flow region 106/channel 122. In some embodiments, the traps 132 are configured to receive or capture a plurality of micro-objects from the flow region 106/channel 122. In some instances, the traps 132 comprise a volume approximately equal to the volume of a single target micro-object.

The traps 132 may further comprise an opening which is configured to assist the flow of targeted micro-objects into the traps 132. In some instances, the traps 132 comprise an opening having a height and width that is size according to the dimensions of a single target micro-object, whereby other micro-objects (or micro-objects that are greater in size) are prevented from entering into the micro-object trap. The traps 132 may further comprise other features configured to assist in retention of targeted micro-objects within the trap 132. In some instances, the trap 132 is aligned with and situated on the opposite side of a channel 122 relative to the opening of a microfluidic sequestration pen, such that upon tilting the microfluidic device 100 about an axis parallel to the channel 122, the trapped micro-object exits the trap 132 at a trajectory that causes the micro-object to fall into the opening of the sequestration pen. In some instances, the trap 132 comprises a side passage 134 that is smaller than the target micro-object in order to facilitate flow through the trap 132 and thereby increase the likelihood of capturing a micro-object in the trap 132.

As discussed in greater detail below, in some embodiments electrowetting (EW) forces are applied at one or more positions on the surface of the support structure 104 (and/or the cover 110) of the microfluidic device 100 (e.g., positions within the flow region and/or the sequestration pens) via one or more electrodes (not shown) to manipulate, transport, separate and sort droplets located in the microfluidic circuit 120. For example, in some embodiments, EW forces are applied at one or more positions on the surface of the support structure 104 (and/or the cover 110) to transfer a droplet from the flow region 106 into a desired microfluidic sequestration pen. In some embodiments, EW forces are used to prevent a droplet within a sequestration pen (e.g., sequestration pen 124, 126, 128, or 130) from being displaced therefrom. Further, in some embodiments, EW forces are used to selectively remove a droplet from a sequestration pen that was previously collected in accordance with the teachings of the instant invention. In some embodiments, the EW forces comprise opto-electrowetting (OEW) forces.

In some embodiments, dielectrophoretic (DEP) forces are applied across the fluidic medium 180 (e.g., in the flow region and/or in the sequestration pens) via one or more electrodes (not shown) to manipulate, transport, separate and sort micro-objects located therein. For example, in some embodiments, DEP forces are applied within one or more portions of microfluidic circuit 120 to transfer a single micro-object from the flow region 106 into a desired microfluidic sequestration pen. In some embodiments, DEP forces are used to prevent a micro-object within a sequestration pen (e.g., sequestration pen 124, 126, 128, or 130) from being displaced therefrom. Further, in some embodiments, DEP forces are used to selectively remove a micro-object from a sequestration pen that was previously collected in accordance with the teachings of the instant invention. In some embodiments, the DEP forces comprise optoelectronic tweezer (OET) forces.

In some embodiments, DEP and/or EW forces are combined with other forces, such as flow and/or gravitational force, so as to manipulate, transport, separate and sort micro-objects and/or droplets within the microfluidic circuit 120. For example, the enclosure 102 can be tilted (e.g., by tilting device 190) to position the flow region 106/channel 122 and micro-objects located therein above the microfluidic sequestration pens, and the force of gravity can transport the micro-objects and/or droplets into the pens. In some embodiments, the DEP and/or EW forces can be applied prior to the other forces. In other embodiments, the DEP and/or EW forces can be applied after the other forces. In still other instances, the DEP and/or EW forces can be applied at the same time as the other forces or in an alternating manner with the other forces.

Figure 2A:
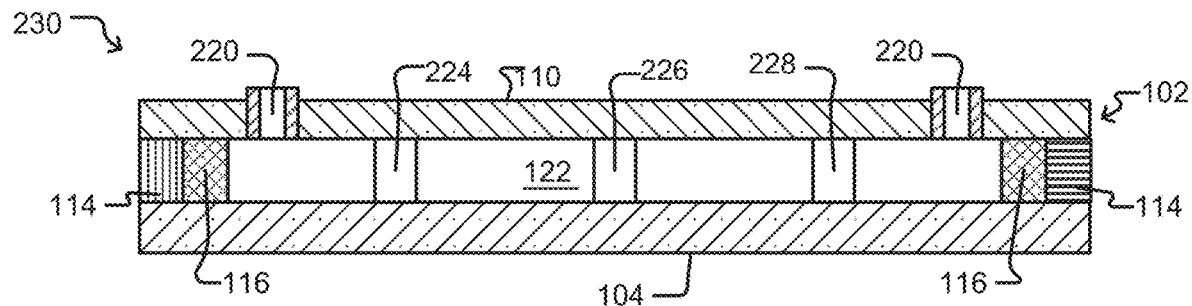
FIGS. 2A and 2B illustrate isolation pens according to some embodiments of the invention.

Microfluidic device motive configurations. As described above, the control and monitoring equipment of the system can comprise a motive module for selecting and moving objects, such as micro-objects or droplets, in the microfluidic circuit of a microfluidic device. The microfluidic devices of the invention can have a variety of motive configurations, depending upon the type of object being moved and other considerations. In particular, the support structure 104 and/or cover 110 of the microfluidic device 100 can comprise an electrowetting (EW) configuration for selectively inducing EW forces on droplets in a fluidic medium 180 in the microfluidic circuit 120 and thereby select, capture, and/or move individual droplets or groups of droplets. In certain embodiments, the microfluidic devices of the invention can comprise a first section having an EW configuration and a second section having a dielectrophoresis (DEP) configuration. Thus, at least a section of the support structure 104 and/or cover 110 of the microfluidic device 100 can comprise a DEP configuration for selectively inducing DEP forces on micro-objects in a fluidic medium 180 in the microfluidic circuit 120 and thereby select, capture, and/or move individual micro-objects or groups of micro-objects Electrowetting configurations. In certain embodiments, a microfluidic device of the invention can comprise an electrowetting configuration which includes a substrate having a dielectric layer and a droplet actuation surface, the droplet actuation surface comprising a hydrophobic layer covalently bonded to the dielectric layer. The dielectric layer can located beneath the hydrophobic layer such that a droplet resting on the substrate directly contacts the hydrophobic layer. FIG. 2A illustrates an example of a portion of such a microfluidic device.

As shown, apparatus 400 can include a base 104 which comprises the substrate and at least one electrode (e.g., a first electrode) 418. The substrate can comprise various layers, including an outer hydrophobic layer 412, an inner dielectric layer 414, a conductive layer 416, an electrode 418, and optionally a support 420. The hydrophobic layer 412 and the inner dielectric layer 414 can provide an inward-facing surface of the substrate 102 that defines, in part, the enclosure.

Apparatus 400 also includes a cover 110, which includes an outer hydrophobic layer 422, an inner layer 428, which may comprise the at least one electrode, and optionally a support 430. Cover 110 and base 104 are substantially parallel to one another and joined together by a spacing element 108 (e.g., microfluidic circuit material) so as to define an enclosure 435 configured to hold a liquid medium. The liquid medium can be, for example, a hydrophobic liquid, such as an oil. In addition, the enclosure 435 can hold a droplet of liquid 440, such as an aqueous medium. Typically, the liquid medium and the liquid of the droplet are selected to be immiscible liquids.

The spacing element 108 can comprise a polymer. The polymer can be, for example, a silicon-based organic polymer, such as polydimethylsiloxane (PDMS) or photo-patternable silicone (PPS), both available from Dow Corning. Alternatively, the spacing element 108 can comprise an epoxy-based adhesive. The epoxy-based adhesive can be, for example, SU-8 or equivalent types of materials. The spacing element 108 can have a thickness (i.e., the gap between the inner surface of the substrate 104 and the cover 110) of at least 30, 40, 50, 60, 70, 80, 90, 100, or more microns. Thus, for example, the thickness of spacing element 108 can be 30-60 microns, 40-80 microns, 50-100 microns, 60-120 microns, 70-140 microns, 75-150 microns, 80-160 microns, 90-180 microns, or 100-200 microns.

Figure 6:
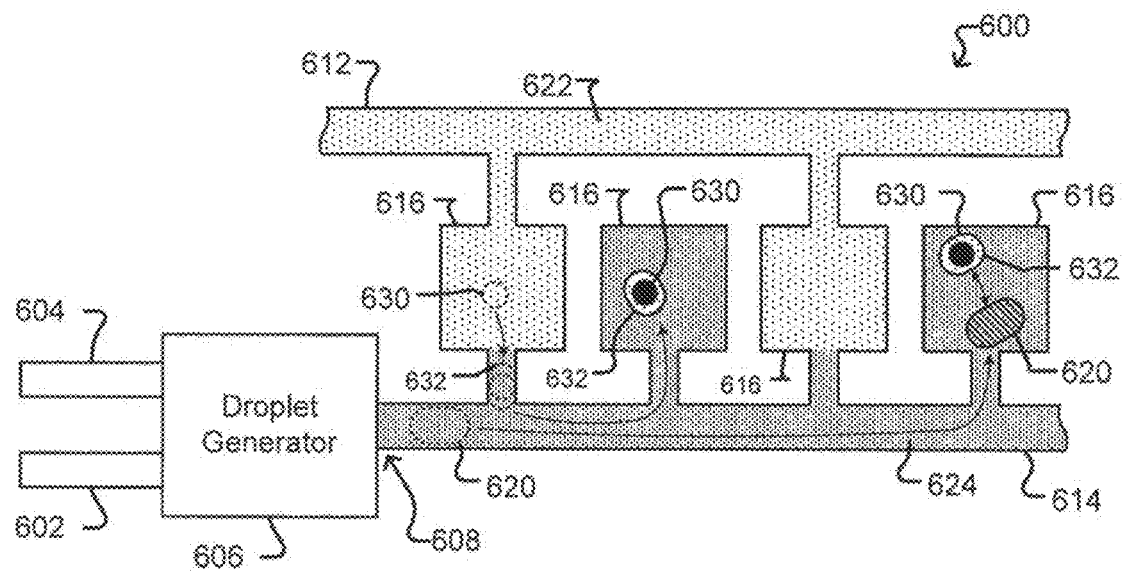
FIG. 6 is a horizontal cross-sectional view of a microfluidic apparatus, which can comprise an electrowetting configuration as shown in FIG. 1B, and which includes multiple microfluidic channels, chambers that open off of at least one of the microfluidic channels, and a droplet generator. In this embodiment, one microfluidic channel contains an aqueous medium (lighter color), while the microfluidic channel connected to the droplet generator contains a non-aqueous medium (darker color). The chambers likewise contain either an aqueous medium or a non-aqueous medium.
Figure 7:
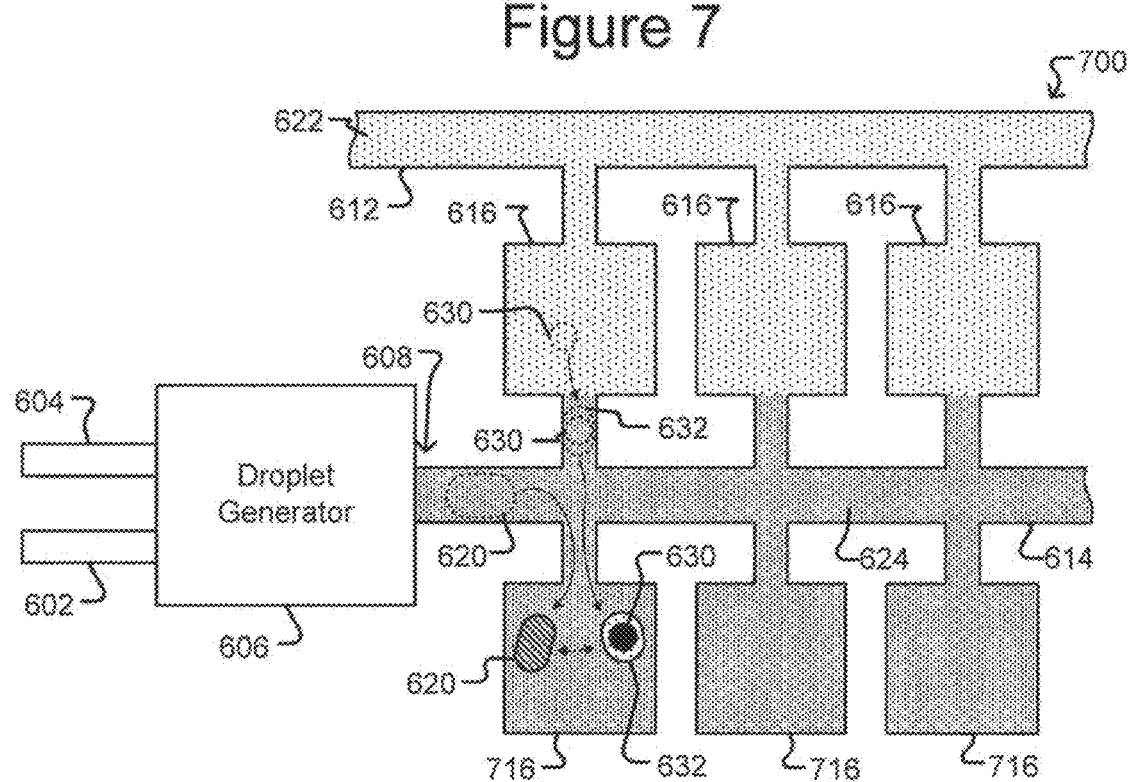
FIG. 7 is a horizontal cross-sectional view of a microfluidic apparatus, which can comprise an electrowetting configuration as shown in FIG. 1B, and which includes multiple microfluidic channels, chambers that open off of at least one of the microfluidic channels, and a droplet generator. In this embodiment, one microfluidic channel and a first set of chambers contains an aqueous medium (lighter color), while the microfluidic channel connected to the droplet generator and a second set of chambers contains a hydrophobic medium (darker color).

The spacing element 108 can define one or more microfluidic channels within the enclosure. In addition, the spacing element 108 can further define a plurality of chambers (or sequestration pens) within the enclosure, wherein each chamber is fluidically connected to and opens off of at least one microfluidic channel Thus, for example, the spacing element 108 can define a single microfluidic channel and a plurality of chambers fluidically connected thereto, or a plurality of microfluidic channels with each channel fluidically connected to a plurality of chambers. Furthermore, each chamber can be fluidically connected to more than one microfluidic channel, as illustrated in FIGS. 6 and 7.

When the at least one electrode 418 of the substrate 104 and the at least one electrode 428 of the cover 110 are connected to opposing terminals of an AC voltage source (not shown), the substrate 104 is capable of applying an electrowetting force to aqueous droplets in contact with the outer hydrophobic surface 412 (i.e., the droplet actuation surface) of the substrate 104. In certain embodiments, the AC voltage used to achieve electrowetting-based movement of a droplet in the microfluidic device is at least 20 Volts peak-to-peak (ppV) (e.g., about 20 to 80 ppV, about 20 to 60 ppV, about 25 to 50 ppV, about 25 to 40 ppV, or about 25 to 35 ppV). In certain embodiments, the frequency of the AC voltage used to achieve electrowetting-based movement of a droplet in the microfluidic device is about 1 to 100 kHz (e.g., about 5 to 90 kHz, about 10 to 80 kHz, about 15 to 70 kHz, about 20 to 60 kHz, about 25 to 50 kHz, or about 30 to 40 kHz).

The outer hydrophobic layer 412 of the substrate 104 and the outer hydrophobic layer 422 of the cover 110 can each comprise a densely packed monolayer of self-associating molecules covalently bound to the inner dielectric layer 414 of the substrate 104 or the inner layer 428 of the cover 110, respectively. The self-associating molecules of the monolayer comprise sufficient two-dimensional packing density so as to create a hydrophobic barrier between a surface to which the monolayer is bound and a hydrophilic liquid (i.e., to prevent intercalation and/or penetration of polar molecules or other chemical species into the monolayer). The packing density of a densely packed monolayer will depend on the self-associating molecules used. A densely packed monolayer comprising alkyl-terminated siloxane will typically comprise at least $1\times10^{14}$ molecules/cm$^2$ (e.g., at least $1.5\times10^{14}$, $2.0\times10^{14}$, $2.5\times10^{14}$, or more molecules/cm$^2$).

As described in greater detail below, the self-associating molecules can each comprise a linking group, such as a siloxane group or a phosphonic acid group. The siloxane groups can be covalently bonded to the molecules of the inner dielectric layer 414 or inner layer 428. Similarly, the phosphonic acid groups can be covalently bonded to the molecules of the inner dielectric layer 414 or inner layer 428. The self-associating molecules can comprise long-chain hydrocarbons, which can be unbranched. Thus, the self-associating molecules can comprise alkyl-terminated siloxane or alkyl-terminated phosphonic acid. The long-chain hydrocarbons can comprise a chain of at least 10 carbons (e.g., at least 16, 18, 20, 22, or more carbons). The self-associating molecules can comprise fluorinated carbon chains. Thus, for example, the self-associating molecules can comprise fluoroalkyl-terminated siloxane or fluoroalkyl-terminated phosphonic acid. The fluorinated carbon chains can have the chemical formula $CF_3-(CF_2)m-(CH_2)n-$, wherein m is at least 2, n is 0, 1, 2, or greater, and m+n is at least 9.

The monolayer of self-associating molecules can have a thickness of less than about 5 nanometers (e.g., about 1.0 to about 4.0 nanometers, about 1.5 to about 3.0 nanometers, or about 2.0 to about 2.5 nanometers).

The outer hydrophobic layer 412 of the substrate 104 can be patterned such that select regions are relatively hydrophilic compared to the remainder of the outer hydrophobic layer. This can be achieved, for example, by increasing the voltage drop across the underlying inner dielectric layer 122 to 50 ppV or greater (e.g., 60, 65, 70, 75, 80, or more ppV) for a period of time. Without intending to be bound by theory, it is believed that the relatively hydrophilic regions comprise water molecules that have intercalated into the monolayer.

In some embodiments, the inner dielectric layer of the substrate can comprise one or more oxide layers. For example, the inner dielectric layer can comprise or consist of a single oxide layer, such as a metal oxide layer. Alternatively, the inner dielectric layer can comprise or consist of two layers. In some embodiments, layer can be silicon dioxide or silicon nitride, and the other layer can be a metal oxide, such as aluminum oxide. In certain embodiment, the thickness of the metal oxide layer can range from about 15 nm to about 45 nm, or about 30 nm to about 40 nm, or about 33 nm to about 36 nm. The metal oxide layer can be deposited by an Atomic Layer Deposition (ALD) technique and the layer comprising silicon dioxide or silicon nitride can be deposited by a Plasma Enhanced Chemical Vapor Deposition (PECVD) technique.

In yet another embodiment, the inner dielectric layer can comprise three layers of dielectric material. In some embodiments, a first layer can comprise a metal oxide, such as aluminum oxide, hafnium oxide, or the like, which can be sandwiched between a silicon dioxide layer and a silicon nitride layer. In certain embodiment, the thickness of the metal oxide layer can range from about 5 nm to about 20 nm, and the layer can be deposited by an Atomic Layer Deposition (ALD) technique. The silicon oxide layer can also be deposited by ALD, and can have a thickness of about 2 nm to about 10 nm. The silicon nitride layer can be deposited by a Plasma Enhanced Chemical Vapor Deposition (PECVD) technique has and can have a thickness of about 80 nm to about 100 nm, or about 90 nm thickness.

Regardless of the number of layers that make up the inner dielectric layer, the inner dielectric layer can have a thickness of about 50 to 105 nanometers and/or an impedance of about 50 to 150 kOhms, with a preferred embodiment of about 100 kOhms.

The substrate 104 can comprise a photoresponsive layer 146 having a first side that contacts the inner dielectric layer 414. The second side of the photoresponsive layer 416 can contact the at least one electrode 418. The photoresponsive layer 416 can comprise hydrogenated amorphous silicon (a-Si:H). For example, the a-Si:H can comprise about 8% to 40% hydrogen (i.e., calculated as 100*the number of hydrogen atoms/total number of hydrogen and silicon atoms). The a-Si:H layer can have a thickness of at least about 500 nanometers (e.g., at least about 600 to 1400, about 700 to 1300, about 800 to 1200, about 900 to 1100, or about 1000 nanometers). However, the thickness of the a-Si:H layer can be varied in accordance with the thickness of the inner dielectric layer 414 so as to achieve a suitable difference between the impedance of the inner dielectric layer 414 and the impedance of the a-Si:H layer when the substrate 104 is in the on state (i.e., illuminated and conducting) and the off state (i.e., dark and non-conducting). For example, the impedance of the inner dielectric layer 414 can be tuned to about 50 kOhms to about 150 kOhms, and the impedance of the a-Si:H layer can be tuned to at least about 0.5 MOhms in the off state and less than or equal to about 1 kOhms in the on state. These are only examples, but they illustrate how the impedances can be tuned to achieve a photoresponsive (in this case, photoconductive) layer 416 displaying robust on/off performance In embodiments where the substrate 104 has a photoresponsive layer 416 formed from a-Si:H layer, the substrate 104 can optionally include floating electrode pads located between the photoresponsive layer 416 and the inner dielectric layer 414. Such floating electrode pads have been described, for example, in U.S. Pat. No. 6,958,132, the contents of which are incorporated herein by reference.

The photoresponsive layer 416 can, alternatively, comprise a plurality of conductors, each conductor controllably connectable to the at least one electrode of the substrate 102 via a phototransistor switch. Conductors controlled by phototransistor switches are well-known in the art and have been described, e.g., in U.S. Patent Application No. 2014/0124370, the contents of which are incorporated herein by reference.

The substrate 104 can comprise a single electrode 418 configured to be connected to an AC voltage source. The single electrode 418 can comprising a layer of indium-tin-oxide (ITO), which can, for example, be formed upon by a glass support 420. Alternatively, the single electrode 418 can comprise a layer of electrically conductive silicon. In other embodiments, the substrate 104 can comprise a plurality of electrodes that are individually addressable, as in the manner of EWOD devices, which are well-known in the art. The individually addressable electrodes can be connectable to one or more AC voltage sources via corresponding transistor switches.

The cover 110 can, in the manner of the substrate, further comprise a dielectric layer (not shown) juxtaposed to the hydrophobic layer 422, and a conductive layer (not shown) juxtaposed between the dielectric layer and the electrode 428. Thus, the microfluidic apparatus 400 can have both the substrate 104 and the cover 110 configured to provide an electrowetting force to an aqueous droplet 440 located within the enclosure 435. In such embodiments, the dielectric layer of the cover 110 can be configured in any of the ways disclosed herein for the inner dielectric layer 414 of the substrate 104, and the conductive layer of the cover 104 can be configured in any of the ways disclosed herein for the conductive layer 126 of the substrate 102.

Figure 1C:
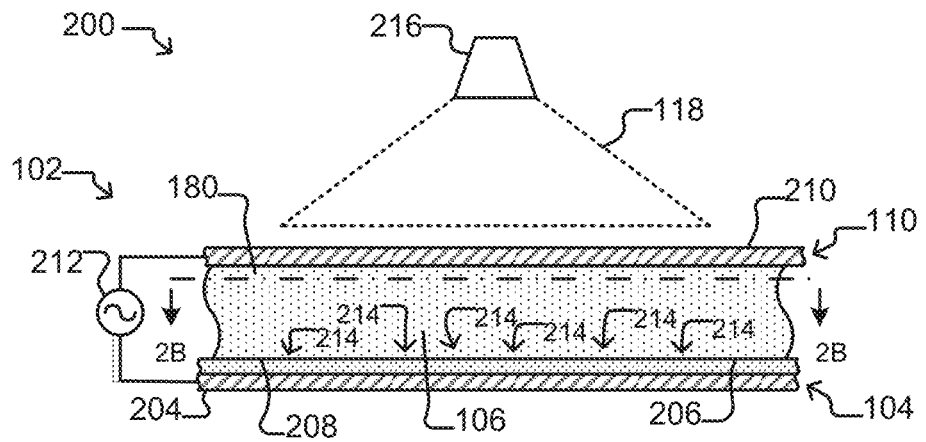
FIGS. 1C and 1D illustrate a microfluidic device according to some embodiments of the invention.
Figure 1D:
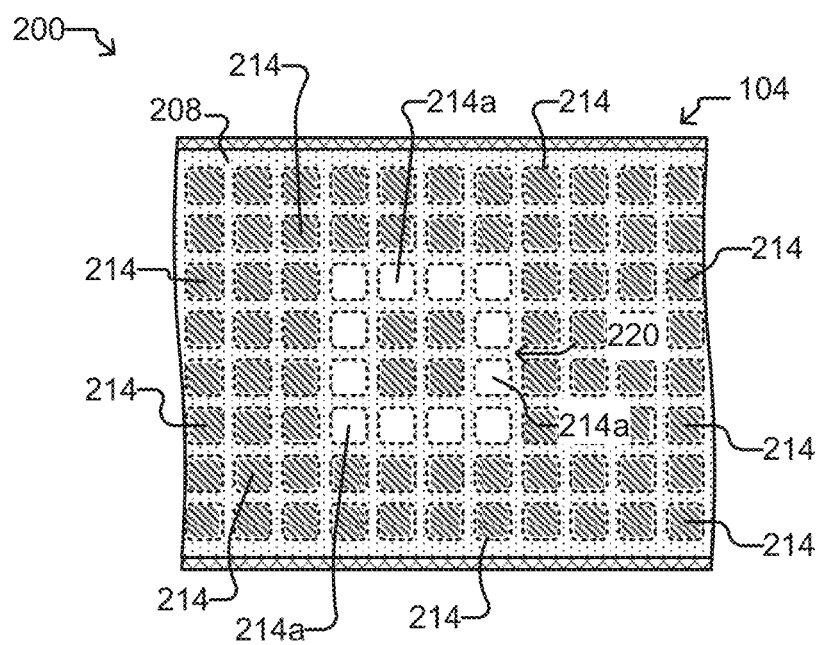

Dielectrophoresis (DEP) configurations. As discussed herein, the microfluidic devices of the invention can include a section having a DEP configuration. One example of such as section is microfluidic device 200 illustrated in FIGS. 1C and 1D While for purposes of simplicity FIGS. 1C and 1D show a vertical cross-sectional view and a horizontal cross-sectional view, respectively, of a portion of an enclosure 102 of the microfluidic device 200 having an open region/chamber 202, it should be understood that the region/chamber 202 may be part of a fluidic circuit element having a more detailed structure, such as a growth chamber, a sequestration pen, a flow region, or a flow channel. Furthermore, the microfluidic device 200 may include other fluidic circuit elements. For example, the microfluidic device 200 can include a plurality of growth chambers or sequestration pens and/or one or more flow regions or flow channels, such as those described herein with respect to microfluidic device 100. A DEP configuration may be incorporated into any such fluidic circuit elements of the microfluidic device 200, or select portions thereof. It should be further appreciated that any of the above or below described microfluidic device components and system components may be incorporated in and/or used in combination with the microfluidic device 200. For example, system 150 including control and monitoring equipment 152, described above, may be used with microfluidic device 200, including one or more of the media module 160, motive module 162, imaging module 164, tilting module 166, and other modules 168.

As seen in FIG. 1C, the microfluidic device 200 includes a support structure 104 having a bottom electrode 204 and an electrode activation substrate 206 overlying the bottom electrode 204, and a cover 110 having a top electrode 210, with the top electrode 210 spaced apart from the bottom electrode 204. The top electrode 210 and the electrode activation substrate 206 define opposing surfaces of the region/chamber 202. A medium 180 contained in the region/chamber 202 thus provides a resistive connection between the top electrode 210 and the electrode activation substrate 206. A power source 212 configured to be connected to the bottom electrode 204 and the top electrode 210 and create a biasing voltage between the electrodes, as required for the generation of DEP forces in the region/chamber 202, is also shown. The power source 212 can be, for example, an alternating current (AC) power source.

In certain embodiments, the microfluidic device 200 illustrated in FIGS. 1C and 1D can have an optically-actuated DEP configuration. Accordingly, changing patterns of light 218 from the light source 216, which may be controlled by the motive module 162, can selectively activate and deactivate changing patterns of DEP electrodes at regions 214 of the inner surface 208 of the electrode activation substrate 206. (Hereinafter the regions 214 of a microfluidic device having a DEP configuration are referred to as "DEP electrode regions.") As illustrated in FIG. 1D, a light pattern 218 directed onto the inner surface 208 of the electrode activation substrate 206 can illuminate select DEP electrode regions 214a (shown in white) in a pattern, such as a square. The non-illuminated DEP electrode regions 214 (cross-hatched) are hereinafter referred to as "dark" DEP electrode regions 214. The relative electrical impedance through the DEP electrode activation substrate 206 (i.e., from the bottom electrode 204 up to the inner surface 208 of the electrode activation substrate 206 which interfaces with the medium 180 in the flow region 106) is greater than the relative electrical impedance through the medium 180 in the region/chamber 202 (i.e., from the inner surface 208 of the electrode activation substrate 206 to the top electrode 210 of the cover 110) at each dark DEP electrode region 214. An illuminated DEP electrode region 214a, however, exhibits a reduced relative impedance through the electrode activation substrate 206 that is less than the relative impedance through the medium 180 in the region/chamber 202 at each illuminated DEP electrode region 214a.

With the power source 212 activated, the foregoing DEP configuration creates an electric field gradient in the fluidic medium 180 between illuminated DEP electrode regions 214a and adjacent dark DEP electrode regions 214, which in turn creates local DEP forces that attract or repel nearby micro-objects (not shown) in the fluidic medium 180. DEP electrodes that attract or repel micro-objects in the fluidic medium 180 can thus be selectively activated and deactivated at many different such DEP electrode regions 214 at the inner surface 208 of the region/chamber 202 by changing light patterns 218 projected from a light source 216 into the microfluidic device 200. Whether the DEP forces attract or repel nearby micro-objects can depend on such parameters as the frequency of the power source 212 and the dielectric properties of the medium 180 and/or micro-objects (not shown).

The square pattern 220 of illuminated DEP electrode regions 214a illustrated in FIG. 1C is an example only. Any pattern of the DEP electrode regions 214 can be illuminated (and thereby activated) by the pattern of light 218 projected into the device 200, and the pattern of illuminated/activated DEP electrode regions 214 can be repeatedly changed by changing or moving the light pattern 218.

In some embodiments, the electrode activation substrate 206 can comprise or consist of a photoconductive material. In such embodiments, the inner surface 208 of the electrode activation substrate 206 can be featureless. For example, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 μm. In such embodiments, the DEP electrode regions 214 can be created anywhere and in any pattern on the inner surface 208 of the electrode activation substrate 206, in accordance with the light pattern 218. The number and pattern of the DEP electrode regions 214 thus need not be fixed, but can correspond to the light pattern 218. Examples of microfluidic devices having a DEP configuration comprising a photoconductive layer such as discussed above have been described, for example, in U.S. Pat. No. RE 44,711 (Wu et al.) (originally issued as U.S. Pat. No. 7,612,355), the entire contents of which are incorporated herein by reference.

Figure 2B:
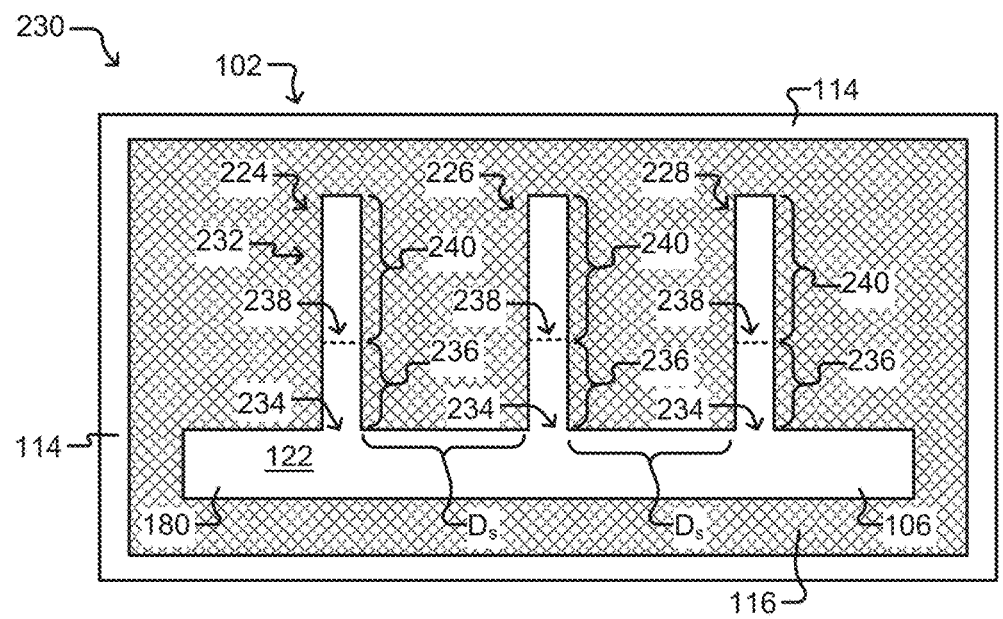

In other embodiments, the electrode activation substrate 206 can comprise a substrate comprising a plurality of doped layers, electrically insulating layers (or regions), and electrically conductive layers that form semiconductor integrated circuits, such as is known in semiconductor fields. For example, the electrode activation substrate 206 can comprise a plurality of phototransistors, including, for example, lateral bipolar phototransistors, each phototransistor corresponding to a DEP electrode region 214. Alternatively, the electrode activation substrate 206 can comprise electrodes (e.g., conductive metal electrodes) controlled by phototransistor switches, with each such electrode corresponding to a DEP electrode region 214. The electrode activation substrate 206 can include a pattern of such phototransistors or phototransistor-controlled electrodes. The pattern, for example, can be an array of substantially square phototransistors or phototransistor-controlled electrodes arranged in rows and columns, such as shown in FIG. 2B. Alternatively, the pattern can be an array of substantially hexagonal phototransistors or phototransistor-controlled electrodes that form a hexagonal lattice. Regardless of the pattern, electric circuit elements can form electrical connections between the DEP electrode regions 214 at the inner surface 208 of the electrode activation substrate 206 and the bottom electrode 210, and those electrical connections (i.e., phototransistors or electrodes) can be selectively activated and deactivated by the light pattern 218. When not activated, each electrical connection can have high impedance such that the relative impedance through the electrode activation substrate 206 (i.e., from the bottom electrode 204 to the inner surface 208 of the electrode activation substrate 206 which interfaces with the medium 180 in the region/chamber 202) is greater than the relative impedance through the medium 180 (i.e., from the inner surface 208 of the electrode activation substrate 206 to the top electrode 210 of the cover 110) at the corresponding DEP electrode region 214. When activated by light in the light pattern 218, however, the relative impedance through the electrode activation substrate 206 is less than the relative impedance through the medium 180 at each illuminated DEP electrode region 214, thereby activating the DEP electrode at the corresponding DEP electrode region 214 as discussed above. DEP electrodes that attract or repel micro-objects (not shown) in the medium 180 can thus be selectively activated and deactivated at many different DEP electrode regions 214 at the inner surface 208 of the electrode activation substrate 206 in the region/chamber 202 in a manner determined by the light pattern 218.

Examples of microfluidic devices having electrode activation substrates that comprise phototransistors have been described, for example, in U.S. Pat. No. 7,956,339 (Ohta et al.) (see, e.g., device 300 illustrated in FIGS. 21 and 22, and descriptions thereof), the entire contents of which are incorporated herein by reference. Examples of microfluidic devices having electrode activation substrates that comprise electrodes controlled by phototransistor switches have been described, for example, in U.S. Patent Publication No. 2014/0124370 (Short et al.) (see, e.g., devices 200, 400, 500, 600, and 900 illustrated throughout the drawings, and descriptions thereof), the entire contents of which are incorporated herein by reference.

In some embodiments of a DEP configured microfluidic device, the top electrode 210 is part of a first wall (or cover 110) of the enclosure 102, and the electrode activation substrate 206 and bottom electrode 204 are part of a second wall (or support structure 104) of the enclosure 102. The region/chamber 202 can be between the first wall and the second wall. In other embodiments, the electrode 210 is part of the second wall (or support structure 104) and one or both of the electrode activation substrate 206 and/or the electrode 210 are part of the first wall (or cover 110). Moreover, the light source 216 can alternatively be used to illuminate the enclosure 102 from below.

With the microfluidic device 200 of FIGS. 1C-1D having a DEP configuration, the motive module 162 can select a micro-object (not shown) in the medium 180 in the region/chamber 202 by projecting a light pattern 218 into the device 200 to activate a first set of one or more DEP electrodes at DEP electrode regions 214a of the inner surface 208 of the electrode activation substrate 206 in a pattern (e.g., square pattern 220) that surrounds and captures the micro-object. The motive module 162 can then move the captured micro-object by moving the light pattern 218 relative to the device 200 to activate a second set of one or more DEP electrodes at DEP electrode regions 214. Alternatively, the device 200 can be moved relative to the light pattern 218.

In other embodiments, the microfluidic device 200 can have a DEP configuration that does not rely upon light activation of DEP electrodes at the inner surface 208 of the electrode activation substrate 206. For example, the electrode activation substrate 206 can comprise selectively addressable and energizable electrodes positioned opposite to a surface including at least one electrode (e.g., cover 110). Switches (e.g., transistor switches in a semiconductor substrate) may be selectively opened and closed to activate or inactivate DEP electrodes at DEP electrode regions 214, thereby creating a net DEP force on a micro-object (not shown) in region/chamber 202 in the vicinity of the activated DEP electrodes. Depending on such characteristics as the frequency of the power source 212 and the dielectric properties of the medium (not shown) and/or micro-objects in the region/chamber 202, the DEP force can attract or repel a nearby micro-object. By selectively activating and deactivating a set of DEP electrodes (e.g., at a set of DEP electrodes regions 214 that forms a square pattern 220), one or more micro-objects in region/chamber 202 can be trapped and moved within the region/chamber 202. The motive module 162 in FIG. 1A can control such switches and thus activate and deactivate individual ones of the DEP electrodes to select, trap, and move particular micro-objects (not shown) around the region/chamber 202. Microfluidic devices having a DEP configuration that includes selectively addressable and energizable electrodes are known in the art and have been described, for example, in U.S. Pat. No. 6,294,063 (Becker et al.) and U.S. Pat. No. 6,942,776 (Medoro), the entire contents of which are incorporated herein by reference.

Microfluidic devices with electrowetting and dielectrophoresis (DEP) configurations. FIG. 4 is a vertical cross-sectional view of a microfluidic device or apparatus 450 that integrates multiple microfluidic applications in accordance with various embodiments. The device 450 comprises two different sections (though there could be more), each having a single microfluidic configuration. Section 460 comprises an electrowetting configuration, which includes a base 104 which comprises the substrate. The substrate comprises various layers, including an outer hydrophobic layer 412, an inner dielectric layer 414, a conductive layer 416, and an electrode 418. The hydrophobic layer 412 and the inner dielectric layer 414 can provide an inward-facing surface of the substrate that defines, in part, the enclosure 435. Section 460 also includes a cover 110 comprising an electrode 428 and an outer hydrophobic layer 422, and microfluidic circuit material 108 that connects the base 104 with the cover 110 and further helps to define the microfluidic circuit of the electrowetting section, including enclosure 435 which is configured to hold an immiscible fluid.

Section 470 of microfluidic device 450 comprises a dielectrophoresis DEP configuration, which includes a base 104, a first electrode 479, an electrode activation substrate 474, and an inward-facing surface that defines, in part, the enclosure 475. Section 470 further includes a cover 110 comprising an electrode 468, and microfluidic circuit material 108 that connects the base 104 with the cover 110 and further helps to define the microfluidic circuit of the DEP section.

As shown in FIG. 4, the electrowetting section 460 and the DEP section 470 can share the same base 104 and cover 110, while their substrates and electrodes are not shared. The electrowetting section 460 and the DEP section 470 of device 450 can be joined by a bridge 465, which can be tubing, an adhesive material, or the like, or any combination thereof.

FIG. 5 is a vertical cross-sectional view of a microfluidic device or apparatus 500 that integrates multiple microfluidic applications in accordance with various embodiments. Like device 400, device 500 comprises two different sections (though there could be more), each having a single microfluidic configuration. Specifically, section 460 comprises an electrowetting configuration and section 470 comprises a DEP configuration. The various components of device 500 have corresponding parts to those in device 400, as shown by corresponding reference numbers. However, device 500 has a monolithic substrate having a conductive layer 416, a first electrode 418, and a second electrode 428, all of which are shared by both sections 460 and 470.

Figure 19A:
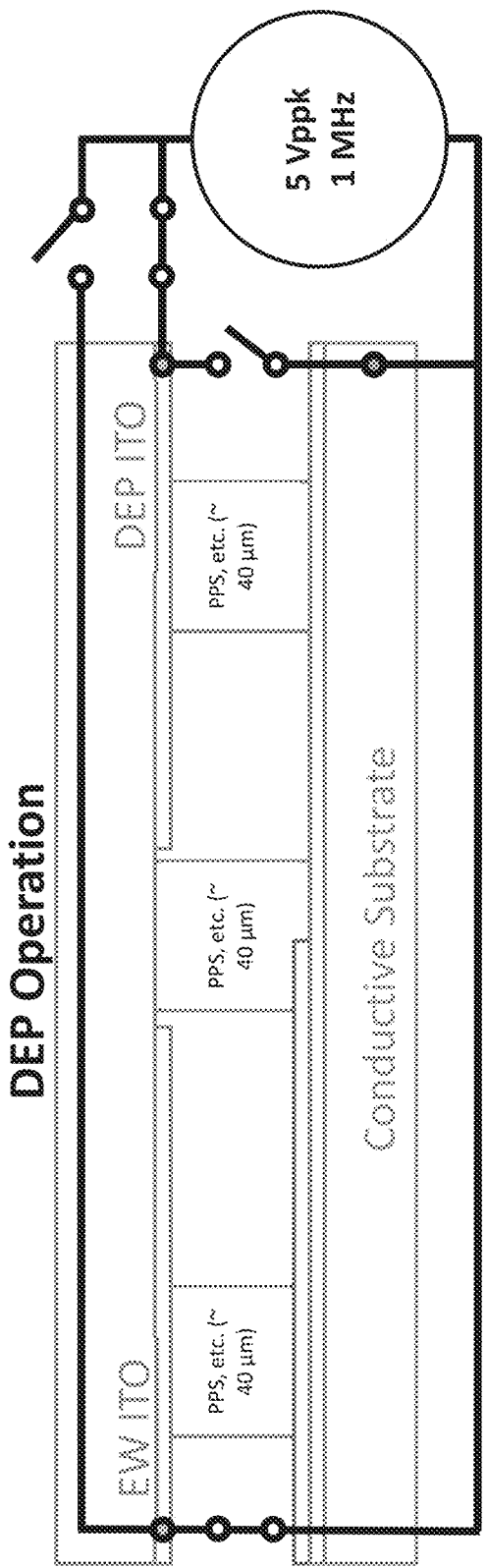
FIG. 19A is a view of an electrical addressing operational representation for one functional aspect in accordance with the embodiment depicted in connection with FIG. 17.
Figure 19B:
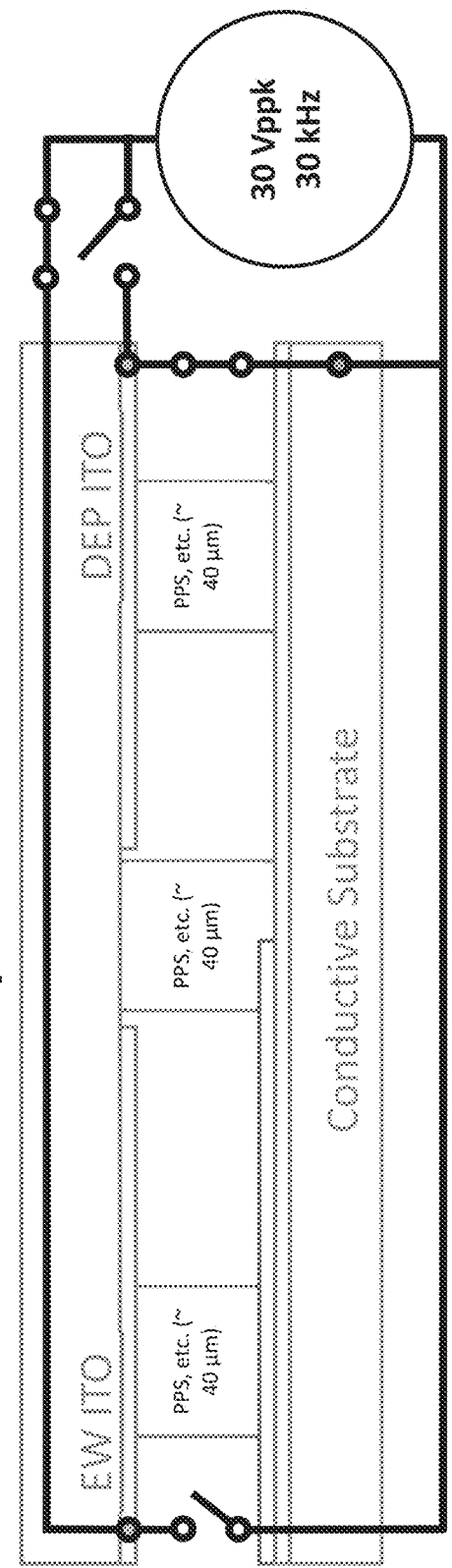
FIG. 19B is a view of an electrical addressing operational representation for one functional aspect in accordance with the embodiment depicted in connection with FIG. 17.

FIGS. 19A and 19B provide a view of an electrical addressing operational representation for one functional aspect in accordance with the embodiments depicted in connection with FIG. 5. As previously described in connection with FIG. 5, the system integrates two microfluidic operations, as depicted by DEP and EW modules that share a monolithic substrate 416. In this embodiment, the DEP (which can be an OET) module has lower impedance relative to the EW module. During operation, the EW module's impedance overcomes the DEP module's impedance and essentially renders the DEP module a short circuit.

In one embodiment as depicted in FIG. 19A, the OEP module operates by applying a voltage in a range of 1-10 Volts at a frequency in a range of 100 kHz to 10 mHz. In the same embodiment, as depicted in FIG. 19B, OEW module operates by applying a voltage in a range of 10-100 Volts at a frequency in a range of 1 kHz to 300 kHz. In one preferred embodiment, the OEP module operates by applying a voltage of 5 Volts at a frequency of 1 Mhz and the OEW module operates by applying a voltage of 30 Volts at a frequency of 30 kHz.

Sequestration pens. Non-limiting examples of generic sequestration pens 224, 226, and 228 are shown within the microfluidic device 230 depicted in FIGS. 2A-2C. Each sequestration pen 224, 226, and 228 can comprise an isolation structure 232 defining an isolation region 240 and a connection region 236 fluidically connecting the isolation region 240 to a channel 122. The connection region 236 can comprise a proximal opening 234 to the channel 122 and a distal opening 238 to the isolation region 240. The connection region 236 can be configured so that the maximum penetration depth of a flow of a fluidic medium (not shown) flowing from the channel 122 into the sequestration pen 224, 226, 228 does not extend into the isolation region 240. Thus, due to the connection region 236, a micro-object (not shown) or other material (not shown) disposed in an isolation region 240 of a sequestration pen 224, 226, 228 can thus be isolated from, and not substantially affected by, a flow of medium 180 in the channel 122.

Figure 2C:
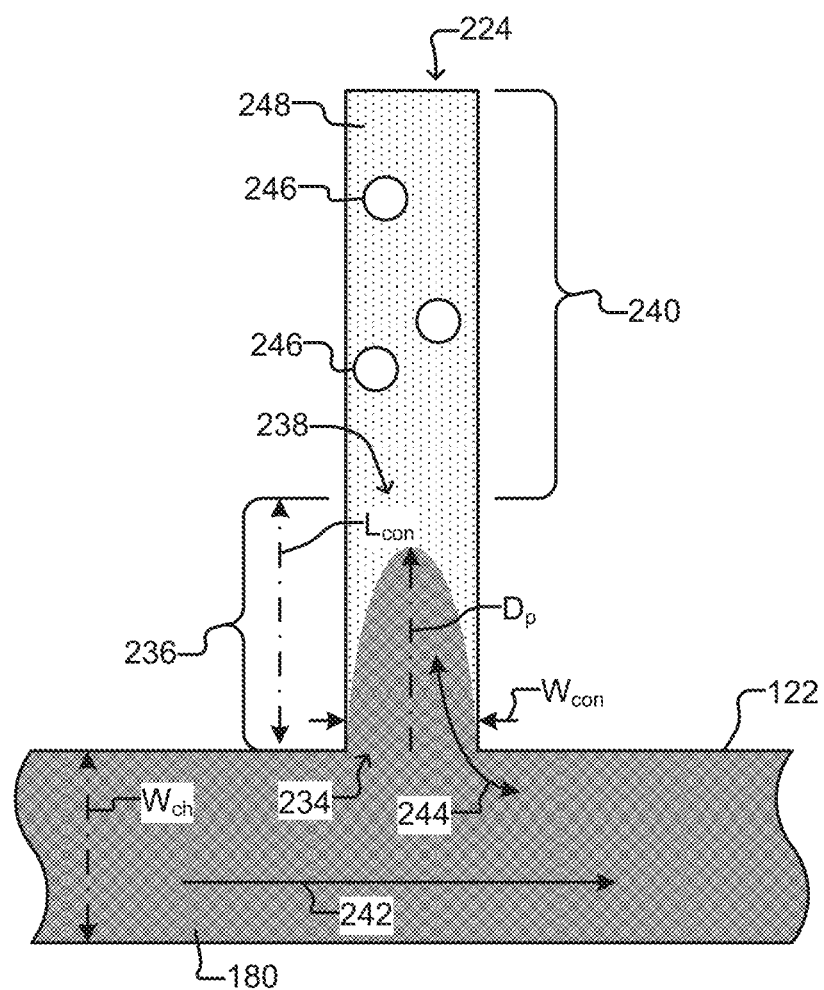
FIG. 2C illustrates a detailed sequestration pen according to some embodiments of the invention.

The sequestration pens 224, 226, and 228 of FIGS. 2A-2C each have a single opening which opens directly to the channel 122. The opening of the sequestration pen opens laterally from the channel 122. The electrode activation substrate 206 underlays both the channel 122 and the sequestration pens 224, 226, and 228. The upper surface of the electrode activation substrate 206 within the enclosure of a sequestration pen, forming the floor of the sequestration pen, is disposed at the same level or substantially the same level of the upper surface the of electrode activation substrate 206 within the channel 122 (or flow region if a channel is not present), forming the floor of the flow channel (or flow region, respectively) of the microfluidic device. The electrode activation substrate 206 may be featureless or may have an irregular or patterned surface that varies from its highest elevation to its lowest depression by less than about 3 microns, 2.5 microns, 2 microns, 1.5 microns, 1 micron, 0.9 microns, 0.5 microns, 0.4 microns, 0.2 microns, 0.1 microns or less. The variation of elevation in the upper surface of the substrate across both the channel 122 (or flow region) and sequestration pens may be less than about 3%, 2%, 1%. 0.9%, 0.8%, 0.5%, 0.3% or 0.1% of the height of the walls of the sequestration pen or walls of the microfluidic device. While described in detail for the microfluidic device 200, this also applies to any of the microfluidic devices 100, 230, 250, 280, 290, 600, 700 described herein.

The channel 122 can thus be an example of a swept region, and the isolation regions 240 of the sequestration pens 224, 226, 228 can be examples of unswept regions. As noted, the channel 122 and sequestration pens 224, 226, 228 can be configured to contain one or more fluidic media 180. In the example shown in FIGS. 2A-2B, the ports 222 are connected to the channel 122 and allow a fluidic medium 180 to be introduced into or removed from the microfluidic device 230. Prior to introduction of the fluidic medium 180, the microfluidic device may be primed with a gas such as carbon dioxide gas. Once the microfluidic device 230 contains the fluidic medium 180, the flow 242 of fluidic medium 180 in the channel 122 can be selectively generated and stopped. For example, as shown, the ports 222 can be disposed at different locations (e.g., opposite ends) of the channel 122, and a flow 242 of medium can be created from one port 222 functioning as an inlet to another port 222 functioning as an outlet.

FIG. 2C illustrates a detailed view of an example of a sequestration pen 224 according to the present invention. Examples of micro-objects 246 are also shown.

As is known, a flow 242 of fluidic medium 180 in a microfluidic channel 122 past a proximal opening 234 of sequestration pen 224 can cause a secondary flow 244 of the medium 180 into and/or out of the sequestration pen 224. To isolate micro-objects 246 in the isolation region 240 of a sequestration pen 224 from the secondary flow 244, the length $L_{con}$ of the connection region 236 of the sequestration pen 224 (i.e., from the proximal opening 234 to the distal opening 238) should be greater than the penetration depth $D_p$ of the secondary flow 244 into the connection region 236. The penetration depth $D_p$ of the secondary flow 244 depends upon the velocity of the fluidic medium 180 flowing in the channel 122 and various parameters relating to the configuration of the channel 122 and the proximal opening 234 of the connection region 236 to the channel 122. For a given microfluidic device, the configurations of the channel 122 and the opening 234 will be fixed, whereas the rate of flow 242 of fluidic medium 180 in the channel 122 will be variable. Accordingly, for each sequestration pen 224, a maximal velocity $V_{max}$ for the flow 242 of fluidic medium 180 in channel 122 can be identified that ensures that the penetration depth $D_p$ of the secondary flow 244 does not exceed the length $L_{con}$ of the connection region 236. As long as the rate of the flow 242 of fluidic medium 180 in the channel 122 does not exceed the maximum velocity $V_{max}$, the resulting secondary flow 244 can be limited to the channel 122 and the connection region 236 and kept out of the isolation region 240. The flow 242 of medium 180 in the channel 122 will thus not draw micro-objects 246 out of the isolation region 240. Rather, micro-objects 246 located in the isolation region 240 will stay in the isolation region 240 regardless of the flow 242 of fluidic medium 180 in the channel 122.

Moreover, as long as the rate of flow 242 of medium 180 in the channel 122 does not exceed $V_{max}$, the flow 242 of fluidic medium 180 in the channel 122 will not move miscellaneous particles (e.g., microparticles and/or nanoparticles) from the channel 122 into the isolation region 240 of a sequestration pen 224. Having the length $L_{con}$ of the connection region 236 be greater than the maximum penetration depth $D_p$ of the secondary flow 244 can thus prevent contamination of one sequestration pen 224 with miscellaneous particles from the channel 122 or another sequestration pen (e.g., sequestration pens 226, 228 in FIG. 2D).

Because the channel 122 and the connection regions 236 of the sequestration pens 224, 226, 228 can be affected by the flow 242 of medium 180 in the channel 122, the channel 122 and connection regions 236 can be deemed swept (or flow) regions of the microfluidic device 230. The isolation regions 240 of the sequestration pens 224, 226, 228, on the other hand, can be deemed unswept (or non-flow) regions. For example, components (not shown) in a first fluidic medium 180 in the channel 122 can mix with a second fluidic medium 248 in the isolation region 240 substantially only by diffusion of components of the first medium 180 from the channel 122 through the connection region 236 and into the second fluidic medium 248 in the isolation region 240. Similarly, components (not shown) of the second medium 248 in the isolation region 240 can mix with the first medium 180 in the channel 122 substantially only by diffusion of components of the second medium 248 from the isolation region 240 through the connection region 236 and into the first medium 180 in the channel 122. In some embodiments, the extent of fluidic medium exchange between the isolation region of a sequestration pen and the flow region by diffusion is greater than about 90%, 91%, 92%, 93%, 94% 95%, 96%, 97%, 98%, or greater than about 99% of fluidic exchange. The first medium 180 can be the same medium or a different medium than the second medium 248. Moreover, the first medium 180 and the second medium 248 can start out being the same, then become different (e.g., through conditioning of the second medium 248 by one or more cells in the isolation region 240, or by changing the medium 180 flowing through the channel 122).

The maximum penetration depth $D_p$ of the secondary flow 244 caused by the flow 242 of fluidic medium 180 in the channel 122 can depend on a number of parameters, as mentioned above. Examples of such parameters include: the shape of the channel 122 (e.g., the channel can direct medium into the connection region 236, divert medium away from the connection region 236, or direct medium in a direction substantially perpendicular to the proximal opening 234 of the connection region 236 to the channel 122); a width $W_{ch}$ (or cross-sectional area) of the channel 122 at the proximal opening 234; and a width $W_{con}$ (or cross-sectional area) of the connection region 236 at the proximal opening 234; the velocity V of the flow 242 of fluidic medium 180 in the channel 122; the viscosity of the first medium 180 and/or the second medium 248, or the like.

In some embodiments, the dimensions of the channel 122 and sequestration pens 224, 226, 228 can be oriented as follows with respect to the vector of the flow 242 of fluidic medium 180 in the channel 122: the channel width $W_{ch}$ (or cross-sectional area of the channel 122) can be substantially perpendicular to the flow 242 of medium 180; the width $W_{con}$ (or cross-sectional area) of the connection region 236 at opening 234 can be substantially parallel to the flow 242 of medium 180 in the channel 122; and/or the length $L_{con}$ of the connection region can be substantially perpendicular to the flow 242 of medium 180 in the channel 122. The foregoing are examples only, and the relative position of the channel 122 and sequestration pens 224, 226, 228 can be in other orientations with respect to each other.

As illustrated in FIG. 2C, the width $W_{con}$ of the connection region 236 can be uniform from the proximal opening 234 to the distal opening 238. The width $W_{con}$ of the connection region 236 at the distal opening 238 can thus be in any of the ranges identified herein for the width $W_{con}$ of the connection region 236 at the proximal opening 234. Alternatively, the width $W_{con}$ of the connection region 236 at the distal opening 238 can be larger than the width $W_{con}$ of the connection region 236 at the proximal opening 234.

As illustrated in FIG. 2C, the width of the isolation region 240 at the distal opening 238 can be substantially the same as the width $W_{con}$ of the connection region 236 at the proximal opening 234. The width of the isolation region 240 at the distal opening 238 can thus be in any of the ranges identified herein for the width $W_{con}$ of the connection region 236 at the proximal opening 234. Alternatively, the width of the isolation region 240 at the distal opening 238 can be larger or smaller than the width $W_{con}$ of the connection region 236 at the proximal opening 234.

Moreover, the distal opening 238 may be smaller than the proximal opening 234 and the width $W_{con}$ of the connection region 236 may be narrowed between the proximal opening 234 and distal opening 238. For example, the connection region 236 may be narrowed between the proximal opening and the distal opening, using a variety of different geometries (e g chamfering the connection region, beveling the connection region). Further, any part or subpart of the connection region 236 may be narrowed (e.g. a portion of the connection region adjacent to the proximal opening 234).

Figure 2D:
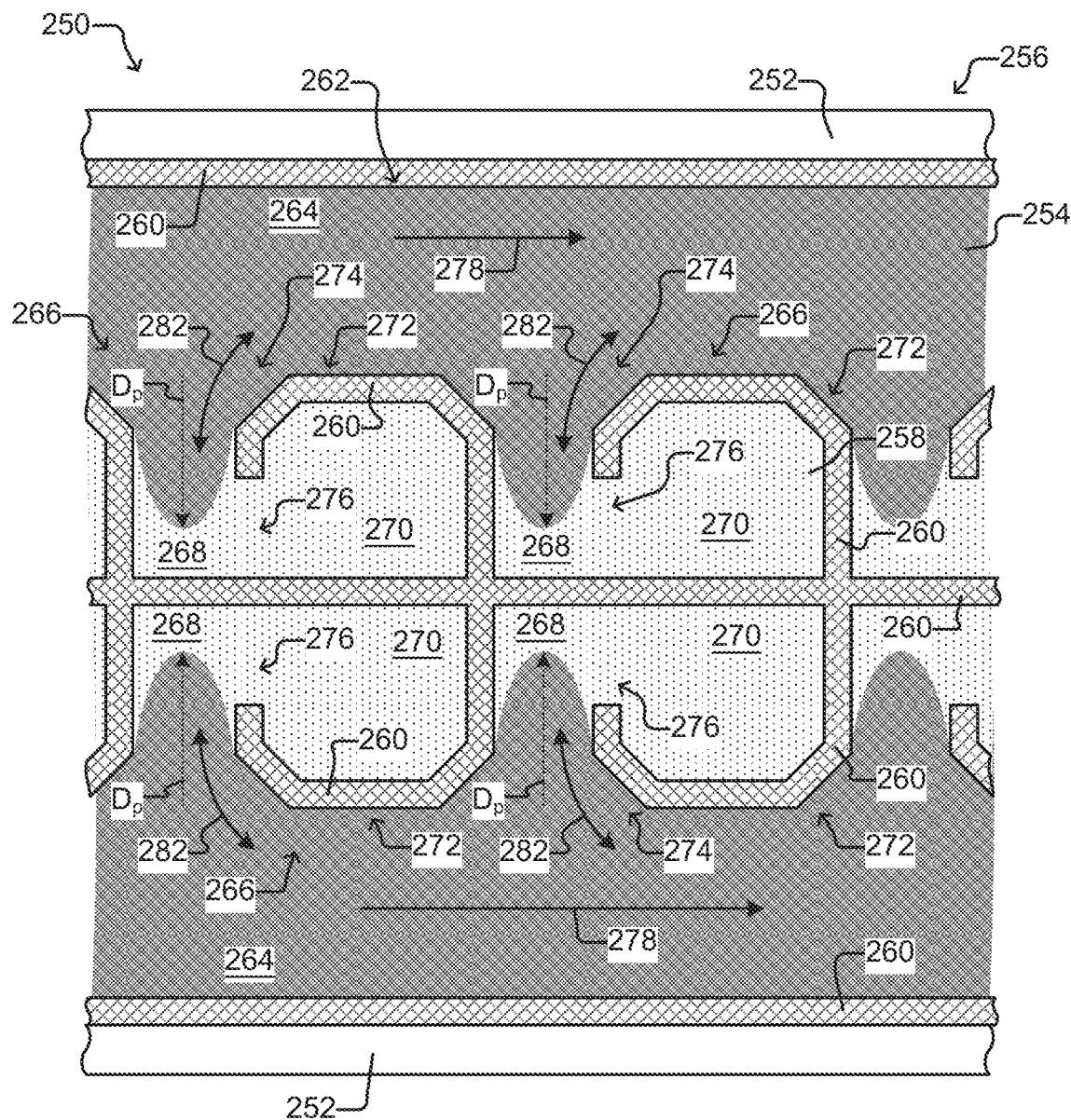
FIGS. 2D-2F illustrate sequestration pens according to some other embodiments of the invention.
Figure 2E:
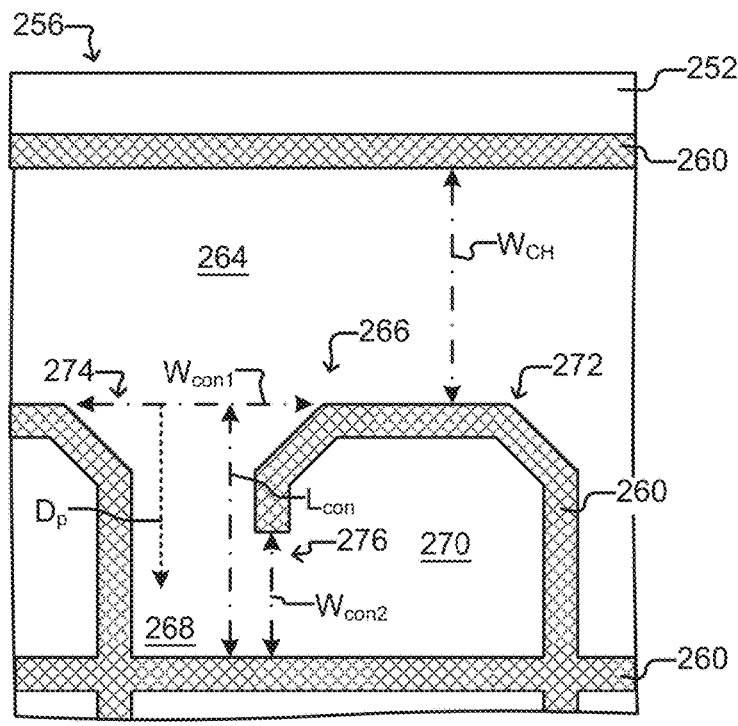
Figure 2F:
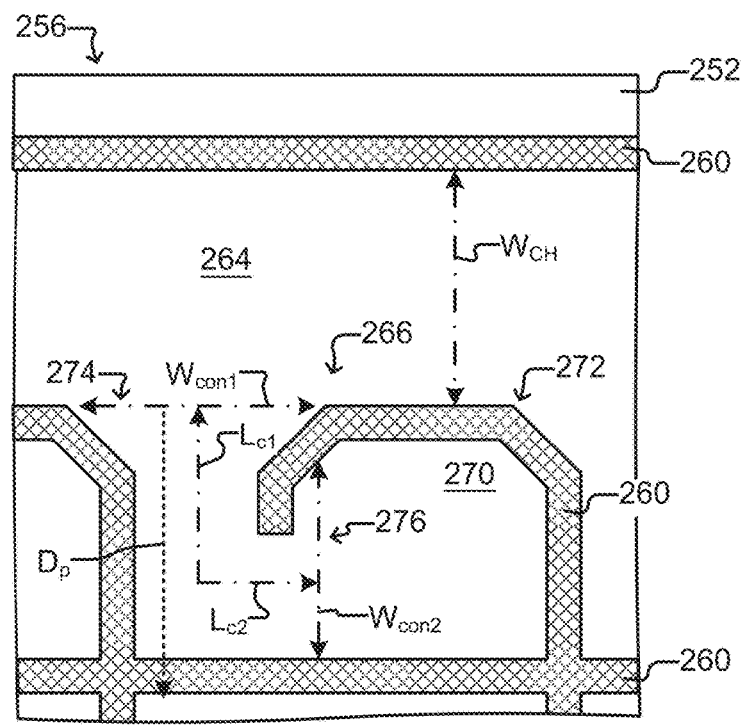

FIGS. 2D-2F depict another exemplary embodiment of a microfluidic device 250 containing a microfluidic circuit 262 and flow channels 264, which are variations of the respective microfluidic device 100, circuit 132 and channel 134 of FIG. 1. The microfluidic device 250 also has a plurality of sequestration pens 266 that are additional variations of the above-described sequestration pens 124, 126, 128, 130, 224, 226 or 228. In particular, it should be appreciated that the sequestration pens 266 of device 250 shown in FIGS. 2D-2F can replace any of the above-described sequestration pens 124, 126, 128, 130, 224, 226 or 228 in devices 100, 200, 230, 280, 290, or 320. Likewise, the microfluidic device 250 is another variant of the microfluidic device 100, and may also have the same or a different DEP configuration as the above-described microfluidic device 100, 200, 230, 280, 290, 320 as well as any of the other microfluidic system components described herein.

The microfluidic device 250 of FIGS. 2D-2F comprises a support structure (not visible in FIGS. 2D-2F, but can be the same or generally similar to the support structure 104 of device 100 depicted in FIG. 1A), a microfluidic circuit structure 256, and a cover (not visible in FIGS. 2D-2F, but can be the same or generally similar to the cover 122 of device 100 depicted in FIG. 1A). The microfluidic circuit structure 256 includes a frame 252 and microfluidic circuit material 260, which can be the same as or generally similar to the frame 114 and microfluidic circuit material 116 of device 100 shown in FIG. 1A. As shown in FIG. 2D, the microfluidic circuit 262 defined by the microfluidic circuit material 260 can comprise multiple channels 264 (two are shown but there can be more) to which multiple sequestration pens 266 are fluidically connected.

Each sequestration pen 266 can comprise an isolation structure 272, an isolation region 270 within the isolation structure 272, and a connection region 268. From a proximal opening 274 at the channel 264 to a distal opening 276 at the isolation structure 272, the connection region 268 fluidically connects the channel 264 to the isolation region 270. Generally, in accordance with the above discussion of FIGS. 2B and 2C, a flow 278 of a first fluidic medium 254 in a channel 264 can create secondary flows 282 of the first medium 254 from the channel 264 into and/or out of the respective connection regions 268 of the sequestration pens 266.

As illustrated in FIG. 2E, the connection region 268 of each sequestration pen 266 generally includes the area extending between the proximal opening 274 to a channel 264 and the distal opening 276 to an isolation structure 272. The length $L_{con}$ of the connection region 268 can be greater than the maximum penetration depth $D_p$ of secondary flow 282, in which case the secondary flow 282 will extend into the connection region 268 without being redirected toward the isolation region 270 (as shown in FIG. 2D). Alternatively, at illustrated in FIG. 2F, the connection region 268 can have a length $L_{con}$ that is less than the maximum penetration depth $D_p$, in which case the secondary flow 282 will extend through the connection region 268 and be redirected toward the isolation region 270. In this latter situation, the sum of lengths $L_{c1}$ and $L_{c2}$ of connection region 268 is greater than the maximum penetration depth $D_p$, so that secondary flow 282 will not extend into isolation region 270. Whether length $L_{con}$ of connection region 268 is greater than the penetration depth $D_p$, or the sum of lengths $L_{c1}$ and $L_{c2}$ of connection region 268 is greater than the penetration depth $D_p$, a flow 278 of a first medium 254 in channel 264 that does not exceed a maximum velocity $V_{max}$ will produce a secondary flow having a penetration depth $D_p$, and micro-objects (not shown but can be the same or generally similar to the micro-objects 246 shown in FIG. 2C) in the isolation region 270 of a sequestration pen 266 will not be drawn out of the isolation region 270 by a flow 278 of first medium 254 in channel 264. Nor will the flow 278 in channel 264 draw miscellaneous materials (not shown) from channel 264 into the isolation region 270 of a sequestration pen 266. As such, diffusion is the only mechanism by which components in a first medium 254 in the channel 264 can move from the channel 264 into a second medium 258 in an isolation region 270 of a sequestration pen 266. Likewise, diffusion is the only mechanism by which components in a second medium 258 in an isolation region 270 of a sequestration pen 266 can move from the isolation region 270 to a first medium 254 in the channel 264. The first medium 254 can be the same medium as the second medium 258, or the first medium 254 can be a different medium than the second medium 258. Alternatively, the first medium 254 and the second medium 258 can start out being the same, then become different, e.g., through conditioning of the second medium by one or more cells in the isolation region 270, or by changing the medium flowing through the channel 264.

As illustrated in FIG. 2E, the width $W_{ch}$ of the channels 264 (i.e., taken transverse to the direction of a fluid medium flow through the channel indicated by arrows 278 in FIG. 2D) in the channel 264 can be substantially perpendicular to a width $W_{con1}$ of the proximal opening 274 and thus substantially parallel to a width $W_{con2}$ of the distal opening 276. The width $W_{con1}$ of the proximal opening 274 and the width $W_{con2}$ of the distal opening 276, however, need not be substantially perpendicular to each other. For example, an angle between an axis (not shown) on which the width $W_{con1}$ of the proximal opening 274 is oriented and another axis on which the width $W_{con2}$ of the distal opening 276 is oriented can be other than perpendicular and thus other than 90°. Examples of alternatively oriented angles include angles in any of the following ranges: from about 30° to about 90°, from about 45° to about 90°, from about 60° to about 90°, or the like.

In various embodiments of sequestration pens (e.g. 124, 126, 128, 130, 224, 226, 228, or 266), the isolation region (e.g. 240 or 270) is configured to contain a plurality of micro-objects. In other embodiments, the isolation region can be configured to contain only one, two, three, four, five, or a similar relatively small number of micro-objects. Accordingly, the volume of an isolation region can be, for example, at least $1 \times 10^6$, $2 \times 10^6$, $4 \times 10^6$, $6 \times 10^6$ cubic microns, or more.

In various embodiments of sequestration pens, the width $W_{ch}$ of the channel (e.g., 122) at a proximal opening (e.g. 234) can be within any of the following ranges: about 50-1000 microns, 50-500 microns, 50-400 microns, 50-300 microns, 50-250 microns, 50-200 microns, 50-150 microns, 50-100 microns, 70-500 microns, 70-400 microns, 70-300 microns, 70-250 microns, 70-200 microns, 70-150 microns, 90-400 microns, 90-300 microns, 90-250 microns, 90-200 microns, 90-150 microns, 100-300 microns, 100-250 microns, 100-200 microns, 100-150 microns, and 100-120 microns. In some other embodiments, the width $W_{ch}$ of the channel (e.g., 122) at a proximal opening (e.g. 234) can be in a range of about 200-800 microns, 200-700 microns, or 200-600 microns. The foregoing are examples only, and the width $W_{ch}$ of the channel 122 can be in other ranges (e.g., a range defined by any of the endpoints listed above). Moreover, the $W_{ch}$ of the channel 122 can be selected to be in any of these ranges in regions of the channel other than at a proximal opening of a sequestration pen.

In some embodiments, a sequestration pen has a height of about 30 to about 200 microns, or about 50 to about 150 microns. In some embodiments, the sequestration pen has a cross-sectional area of about $1 \times 10^4$-$3 \times 10^6$ square microns, $2 \times 10^4$-$2 \times 10^6$ square microns, $4 \times 10^4$-$1 \times 10^6$ square microns, $2 \times 10^4$-$5 \times 10^5$ square microns, $2 \times 10^4$-$1 \times 10^5$ square microns or about $2 \times 10^5$-$2 \times 10^6$ square microns. In some embodiments, the connection region has a cross-sectional width of about 100 to about 500 microns, 200 to about 400 microns or about 200 to about 300 microns.

In various embodiments of sequestration pens, the height $H_{ch}$ of the channel (e.g., 122) at a proximal opening (e.g., 234) can be within any of the following ranges: 20-100 microns, 20-90 microns, 20-80 microns, 20-70 microns, 20-60 microns, 20-50 microns, 30-100 microns, 30-90 microns, 30-80 microns, 30-70 microns, 30-60 microns, 30-50 microns, 40-100 microns, 40-90 microns, 40-80 microns, 40-70 microns, 40-60 microns, or 40-50 microns. The foregoing are examples only, and the height $H_{ch}$ of the channel (e.g., 122) can be in other ranges (e.g., a range defined by any of the endpoints listed above). The height $H_{ch}$ of the channel 122 can be selected to be in any of these ranges in regions of the channel other than at a proximal opening of an sequestration pen.

In various embodiments of sequestration pens a cross-sectional area of the channel (e.g., 122) at a proximal opening (e.g., 234) can be within any of the following ranges: 500-50,000 square microns, 500-40,000 square microns, 500-30,000 square microns, 500-25,000 square microns, 500-20,000 square microns, 500-15,000 square microns, 500-10,000 square microns, 500-7,500 square microns, 500-5,000 square microns, 1,000-25,000 square microns, 1,000-20,000 square microns, 1,000-15,000 square microns, 1,000-10,000 square microns, 1,000-7,500 square microns, 1,000-5,000 square microns, 2,000-20,000 square microns, 2,000-15,000 square microns, 2,000-10,000 square microns, 2,000-7,500 square microns, 2,000-6,000 square microns, 3,000-20,000 square microns, 3,000-15,000 square microns, 3,000-10,000 square microns, 3,000-7,500 square microns, or 3,000 to 6,000 square microns. The foregoing are examples only, and the cross-sectional area of the channel (e.g., 122) at a proximal opening (e.g., 234) can be in other ranges (e.g., a range defined by any of the endpoints listed above).

In various embodiments of sequestration pens, the length $L_{con}$ of the connection region (e.g., 236) can be in any of the following ranges: about 1-600 microns, 5-550 microns, 10-500 microns, 15-400 microns, 20-300 microns, 20-500 microns, 40-400 microns, 60-300 microns, 80-200 microns, or about 100-150 microns. The foregoing are examples only, and length $L_{con}$ of a connection region (e.g., 236) can be in a different range than the foregoing examples (e.g., a range defined by any of the endpoints listed above).

In various embodiments of sequestration pens the width $W_{con}$ of a connection region (e.g., 236) at a proximal opening (e.g., 234) can be in any of the following ranges: 20-500 microns, 20-400 microns, 20-300 microns, 20-200 microns, 20-150 microns, 20-100 microns, 20-80 microns, 20-60 microns, 30-400 microns, 30-300 microns, 30-200 microns, 30-150 microns, 30-100 microns, 30-80 microns, 30-60 microns, 40-300 microns, 40-200 microns, 40-150 microns, 40-100 microns, 40-80 microns, 40-60 microns, 50-250 microns, 50-200 microns, 50-150 microns, 50-100 microns, 50-80 microns, 60-200 microns, 60-150 microns, 60-100 microns, 60-80 microns, 70-150 microns, 70-100 microns, and 80-100 microns. The foregoing are examples only, and the width $W_{con}$ of a connection region (e.g., 236) at a proximal opening (e.g., 234) can be different than the foregoing examples (e.g., a range defined by any of the endpoints listed above).

In various embodiments of sequestration pens, the width $W_{con}$ of a connection region (e.g., 236) at a proximal opening (e.g., 234) can be at least as large as the largest dimension of a micro-object (e.g., biological cell which may be a T cell, B cell, or an ovum or embryo) that the sequestration pen is intended for. For example, the width $W_{con}$ of a connection region 236 at a proximal opening 234 of an sequestration pen that a droplet will be placed into can be in any of the following ranges: about 100 microns, about 110 microns, about 120 microns, about 130 microns, about 140 microns, about 150 microns, about 160 microns, about 170 microns, about 180 microns, about 190 microns, about 200 microns, about 225 microns, about 250 microns, about 300 microns or about 100-400 microns, about 120-350 microns, about 140-200-200 300 microns, or about 140-200 microns. The foregoing are examples only, and the width $W_{con}$ of a connection region (e.g., 236) at a proximal opening (e.g., 234) can be different than the foregoing examples (e.g., a range defined by any of the endpoints listed above).

In various embodiments of sequestration pens, the width $W_pr$ of a proximal opening of a connection region may be at least as large as the largest dimension of a micro-object (e.g., a biological micro-object such as a cell) that the sequestration pen is intended for. For example, the width $W_{pr}$ may be about 50 microns, about 60 microns, about 100 microns, about 200 microns, about 300 microns or may be in a range of about 50-300 microns, about 50-200 microns, about 50-100 microns, about 75-150 microns, about 75-100 microns, or about 200-300 microns In various embodiments of sequestration pens, a ratio of the length $L_{con}$ of a connection region (e.g., 236) to a width $W_{con}$ of the connection region (e.g., 236) at the proximal opening 234 can be greater than or equal to any of the following ratios: 0.5, 1.0, 1.5, 2.0, 2.5, 3.0, 3.5, 4.0, 4.5, 5.0, 6.0, 7.0, 8.0, 9.0, 10.0, or more. The foregoing are examples only, and the ratio of the length Lon of a connection region 236 to a width $W_{con}$ of the connection region 236 at the proximal opening 234 can be different than the foregoing examples.

In various embodiments of microfluidic devices 100, 200, 230, 250, 280, 290, 320, 600, 700 $V_{max}$ can be set around 0.2, 0.3, 0.4, 0.5, 0.6, 0.7, 0.8, 0.9, 1.0, 1.1, 1.2, 1.3, 1.4, or 1.5 μL/sec.

In various embodiments of microfluidic devices having sequestration pens, the volume of an isolation region (e.g., 240) of a sequestration pen can be, for example, at least $5 \times 10^5$, $8 \times 10^5$, $1 \times 10^6$, $2 \times 10^6$, $4 \times 10^6$, $6 \times 10^6$, $8 \times 10^6$, $1 \times 10^7$, $5 \times 10^7$, $1 \times 10^8$, $5 \times 10^8$, or $8 \times 10^8$ cubic microns, or more. In various embodiments of microfluidic devices having sequestration pens, the volume of a sequestration pen may be about $5 \times 10^5$, $6 \times 10^5$, $8 \times 10^5$, $1 \times 10^6$, $2 \times 10^6$, $4 \times 10^6$, $8 \times 10^6$, $1 \times 10^7$, $3 \times 10^7$, $5 \times 10^7$, or about $8 \times 10^7$ cubic microns, or more. In some other embodiments, the volume of a sequestration pen may be about 1 nanoliter to about 50 nanoliters, 2 nanoliters to about 25 nanoliters, 2 nanoliters to about 20 nanoliters, about 2 nanoliters to about 15 nanoliters, or about 2 nanoliters to about 10 nanoliters.

In various embodiment, the microfluidic device has sequestration pens configured as in any of the embodiments discussed herein where the microfluidic device has about 5 to about 10 sequestration pens, about 10 to about 50 sequestration pens, about 100 to about 500 sequestration pens; about 200 to about 1000 sequestration pens, about 500 to about 1500 sequestration pens, about 1000 to about 2000 sequestration pens, or about 1000 to about 3500 sequestration pens. The sequestration pens need not all be the same size and may include a variety of configurations (e.g., different widths, different features within the sequestration pen.

In some other embodiments, the microfluidic device has sequestration pens configured as in any of the embodiments discussed herein where the microfluidic device has about 1500 to about 3000 sequestration pens, about 2000 to about 3500 sequestration pens, about 2500 to about 4000 sequestration pens about 3000 to about 4500 sequestration pens, about 3500 to about 5000 sequestration pens, about 4000 to about 5500 sequestration pens, about 4500 to about 6000 sequestration pens, about 5000 to about 6500 sequestration pens, about 5500 to about 7000 sequestration pens, about 6000 to about 7500 sequestration pens, about 6500 to about 8000 sequestration pens, about 7000 to about 8500 sequestration pens, about 7500 to about 9000 sequestration pens, about 8000 to about 9500 sequestration pens, about 8500 to about 10,000 sequestration pens, about 9000 to about 10,500 sequestration pens, about 9500 to about 11,000 sequestration pens, about 10,000 to about 11,500 sequestration pens, about 10,500 to about 12,000 sequestration pens, about 11,000 to about 12,500 sequestration pens, about 11,500 to about 13,000 sequestration pens, about 12,000 to about 13,500 sequestration pens, about 12,500 to about 14,000 sequestration pens, about 13,000 to about 14,500 sequestration pens, about 13,500 to about 15,000 sequestration pens, about 14,000 to about 15,500 sequestration pens, about 14,500 to about 16,000 sequestration pens, about 15,000 to about 16,500 sequestration pens, about 15,500 to about 17,000 sequestration pens, about 16,000 to about 17,500 sequestration pens, about 16,500 to about 18,000 sequestration pens, about 17,000 to about 18,500 sequestration pens, about 17,500 to about 19,000 sequestration pens, about 18,000 to about 19,500 sequestration pens, about 18,500 to about 20,000 sequestration pens, about 19,000 to about 20,500 sequestration pens, about 19,500 to about 21,000 sequestration pens, or about 20,000 to about 21,500 sequestration pens.

Figure 2G:
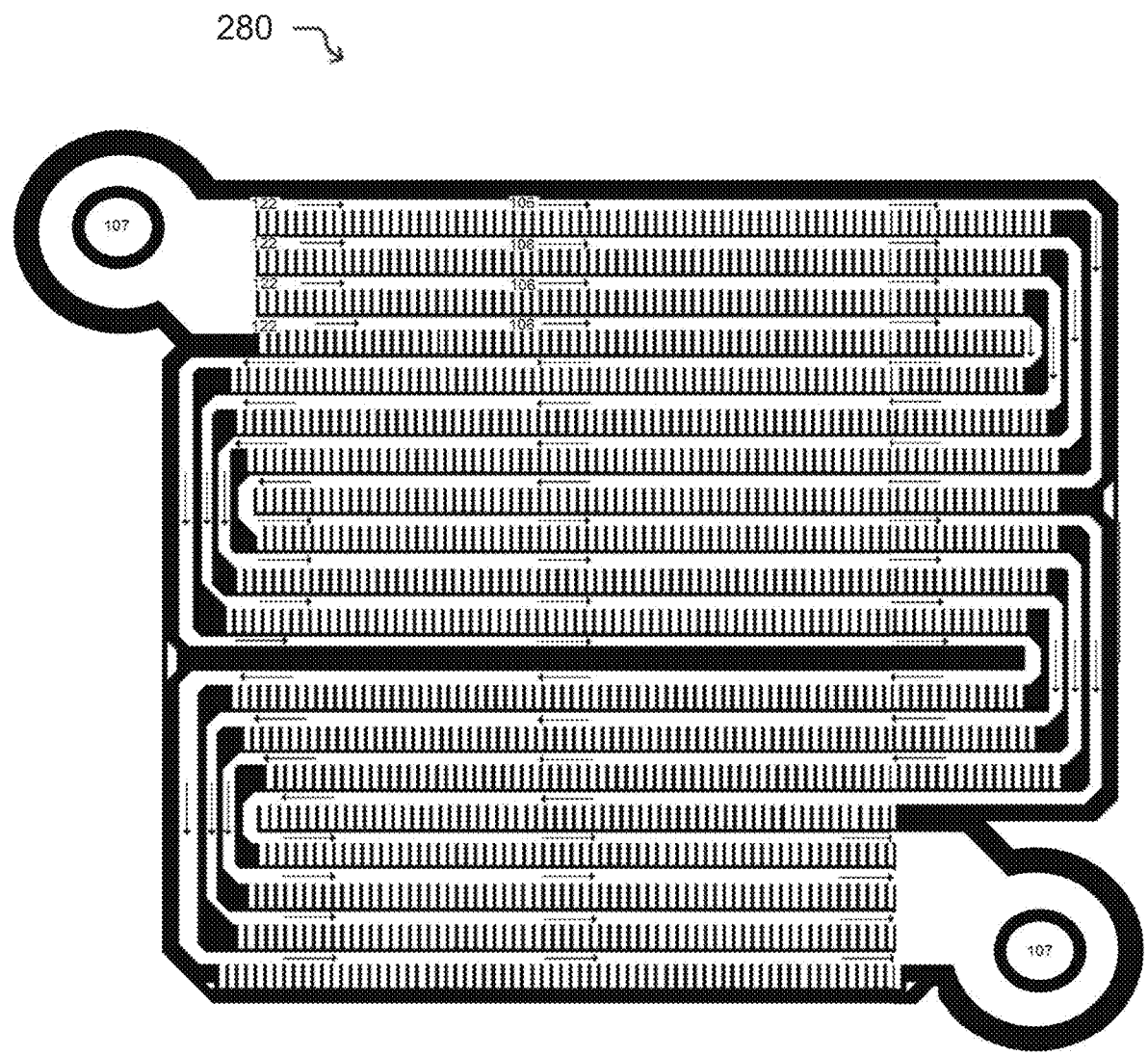
FIG. 2G illustrates a microfluidic device according to an embodiment of the invention.

FIG. 2G illustrates a microfluidic device 280 according to one embodiment. The microfluidic device 280 is illustrated in FIG. 2G is a stylized diagram of a microfluidic device 100. In practice the microfluidic device 280 and its constituent circuit elements (e.g. channels 122 and sequestration pens 128) would have the dimensions discussed herein. The microfluidic circuit 120 illustrated in FIG. 2G has two ports 107 and a flow region 106 with four distinct channels 122. The microfluidic device 280 further comprises a plurality of sequestration pens opening off of each channel 122. In the microfluidic device illustrated in FIG. 2G, the sequestration pens have a geometry similar to the pens illustrated in FIG. 2C and thus, have both connection regions and isolation regions. Accordingly, the microfluidic circuit 120 includes both swept regions (e.g. channels 122 and portions of the connection regions 236 within the maximum penetration depth $D_p$ of the secondary flow 244) and non-swept regions (e.g. isolation regions 240 and portions of the connection regions 236 not within the maximum penetration depth $D_p$ of the secondary flow 244).

Figure 3A:
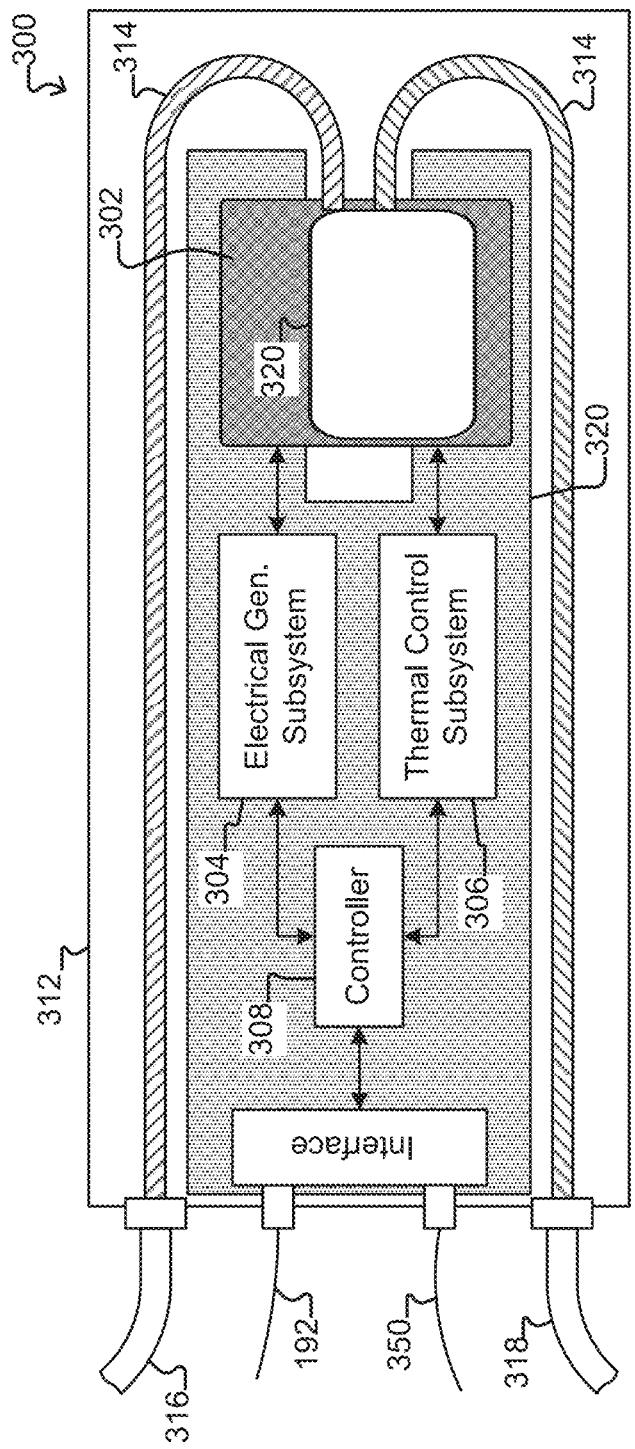
FIG. 3A illustrates a specific example of a system for use with a microfluidic device and associated control equipment according to some embodiments of the invention.
Figure 3B:
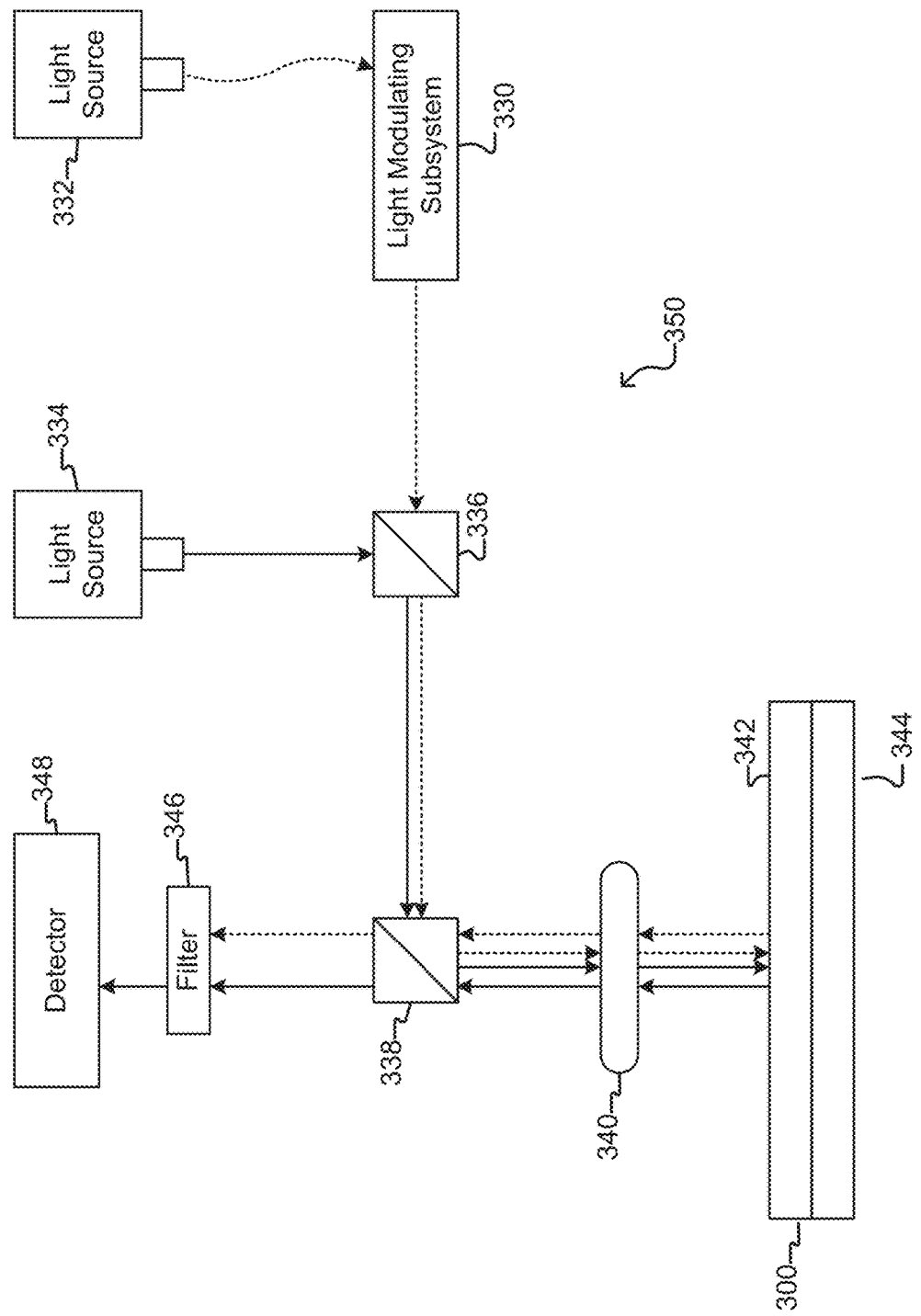
FIG. 3B illustrates an imaging device according to some embodiments of the invention.

FIGS. 3A through 3B shows various embodiments of system 150 which can be used to operate and observe microfluidic devices (e.g. 100, 200, 230, 280, 250, 290, 320) according to the present invention. As illustrated in FIG. 3A, the system 150 can include a structure ("nest") 300 configured to hold a microfluidic device 100 (not shown), or any other microfluidic device described herein. The nest 300 can include a socket 302 capable of interfacing with the microfluidic device 320 (e.g., an optically-actuated electrokinetic device 100) and providing electrical connections from power source 192 to microfluidic device 320. The nest 300 can further include an integrated electrical signal generation subsystem 304. The electrical signal generation subsystem 304 can be configured to supply a biasing voltage to socket 302 such that the biasing voltage is applied across a pair of electrodes in the microfluidic device 320 when it is being held by socket 302. Thus, the electrical signal generation subsystem 304 can be part of power source 192. The ability to apply a biasing voltage to microfluidic device 320 does not mean that a biasing voltage will be applied at all times when the microfluidic device 320 is held by the socket 302. Rather, in most cases, the biasing voltage will be applied intermittently, e.g., only as needed to facilitate the generation of electrokinetic forces, such as dielectrophoresis or electro-wetting, in the microfluidic device 320.

As illustrated in FIG. 3A, the nest 300 can include a printed circuit board assembly (PCBA) 322. The electrical signal generation subsystem 304 can be mounted on and electrically integrated into the PCBA 322. The exemplary support includes socket 302 mounted on PCBA 322, as well.

Typically, the electrical signal generation subsystem 304 will include a waveform generator (not shown). The electrical signal generation subsystem 304 can further include an oscilloscope (not shown) and/or a waveform amplification circuit (not shown) configured to amplify a waveform received from the waveform generator. The oscilloscope, if present, can be configured to measure the waveform supplied to the microfluidic device 320 held by the socket 302. In certain embodiments, the oscilloscope measures the waveform at a location proximal to the microfluidic device 320 (and distal to the waveform generator), thus ensuring greater accuracy in measuring the waveform actually applied to the device. Data obtained from the oscilloscope measurement can be, for example, provided as feedback to the waveform generator, and the waveform generator can be configured to adjust its output based on such feedback. An example of a suitable combined waveform generator and oscilloscope is the Red Pitaya™.

In certain embodiments, the nest 300 further comprises a controller 308, such as a microprocessor used to sense and/or control the electrical signal generation subsystem 304. Examples of suitable microprocessors include the Arduino™ microprocessors, such as the Arduino Nano™. The controller 308 may be used to perform functions and analysis or may communicate with an external master controller 154 (shown in FIG. 1A) to perform functions and analysis. In the embodiment illustrated in FIG. 3A the controller 308 communicates with a master controller 154 through an interface 310 (e.g., a plug or connector).

In some embodiments, the nest 300 can comprise an electrical signal generation subsystem 304 comprising a Red Pitaya™ waveform generator/oscilloscope unit ("Red Pitaya unit") and a waveform amplification circuit that amplifies the waveform generated by the Red Pitaya unit and passes the amplified voltage to the microfluidic device 100. In some embodiments, the Red Pitaya unit is configured to measure the amplified voltage at the microfluidic device 320 and then adjust its own output voltage as needed such that the measured voltage at the microfluidic device 320 is the desired value. In some embodiments, the waveform amplification circuit can have a +6.5V to −6.5V power supply generated by a pair of DC-DC converters mounted on the PCBA 322, resulting in a signal of up to 13 Vpp at the microfluidic device 100.

As illustrated in FIG. 3A, the support structure 300 can further include a thermal control subsystem 306. The thermal control subsystem 306 can be configured to regulate the temperature of microfluidic device 320 held by the support structure 300. For example, the thermal control subsystem 306 can include a Peltier thermoelectric device (not shown) and a cooling unit (not shown). The Peltier thermoelectric device can have a first surface configured to interface with at least one surface of the microfluidic device 320. The cooling unit can be, for example, a cooling block (not shown), such as a liquid-cooled aluminum block. A second surface of the Peltier thermoelectric device (e.g., a surface opposite the first surface) can be configured to interface with a surface of such a cooling block. The cooling block can be connected to a fluidic path 314 configured to circulate cooled fluid through the cooling block. In the embodiment illustrated in FIG. 3A, the support structure 300 comprises an inlet 316 and an outlet 318 to receive cooled fluid from an external reservoir (not shown), introduce the cooled fluid into the fluidic path 314 and through the cooling block, and then return the cooled fluid to the external reservoir. In some embodiments, the Peltier thermoelectric device, the cooling unit, and/or the fluidic path 314 can be mounted on a casing 312 of the support structure 300. In some embodiments, the thermal control subsystem 306 is configured to regulate the temperature of the Peltier thermoelectric device so as to achieve a target temperature for the microfluidic device 320. Temperature regulation of the Peltier thermoelectric device can be achieved, for example, by a thermoelectric power supply, such as a Pololu™ thermoelectric power supply (Pololu Robotics and Electronics Corp.). The thermal control subsystem 306 can include a feedback circuit, such as a temperature value provided by an analog circuit. Alternatively, the feedback circuit can be provided by a digital circuit.

In some embodiments, the nest 300 can include a thermal control subsystem 306 with a feedback circuit that is an analog voltage divider circuit (not shown) which includes a resistor (e.g., with resistance 1 kOhm+/−0.1%, temperature coefficient+/−0.02 ppm/C0) and a NTC thermistor (e.g., with nominal resistance 1 kOhm+/−0.01%). In some instances, the thermal control subsystem 306 measures the voltage from the feedback circuit and then uses the calculated temperature value as input to an on-board PID control loop algorithm. Output from the PID control loop algorithm can drive, for example, both a directional and a pulse-width-modulated signal pin on a Pololu™ motor drive (not shown) to actuate the thermoelectric power supply, thereby controlling the Peltier thermoelectric device.

The nest 300 can include a serial port 324 which allows the microprocessor of the controller 308 to communicate with an external master controller 154 via the interface 310 (not shown). In addition, the microprocessor of the controller 308 can communicate (e.g., via a Plink tool (not shown)) with the electrical signal generation subsystem 304 and thermal control subsystem 306. Thus, via the combination of the controller 308, the interface 310, and the serial port 324, the electrical signal generation subsystem 304 and the thermal control subsystem 306 can communicate with the external master controller 154. In this manner, the master controller 154 can, among other things, assist the electrical signal generation subsystem 304 by performing scaling calculations for output voltage adjustments. A Graphical User Interface (GUI) (not shown) provided via a display device 170 coupled to the external master controller 154, can be configured to plot temperature and waveform data obtained from the thermal control subsystem 306 and the electrical signal generation subsystem 304, respectively. Alternatively, or in addition, the GUI can allow for updates to the controller 308, the thermal control subsystem 306, and the electrical signal generation subsystem 304.

As discussed above, system 150 can include an imaging device 194. In some embodiments, the imaging device 194 comprises a light modulating subsystem 330 (See FIG. 3B).

The light modulating subsystem 330 can include a digital mirror device (DMD) or a microshutter array system (MSA), either of which can be configured to receive light from a light source 332 and transmits a subset of the received light into an optical train of microscope 350. Alternatively, the light modulating subsystem 330 can include a device that produces its own light (and thus dispenses with the need for a light source 332), such as an organic light emitting diode display (OLED), a liquid crystal on silicon (LCOS) device, a ferroelectric liquid crystal on silicon device (FLCOS), or a transmissive liquid crystal display (LCD). The light modulating subsystem 330 can be, for example, a projector. Thus, the light modulating subsystem 330 can be capable of emitting both structured and unstructured light. One example of a suitable light modulating subsystem 330 is the Mosaic™ system from Andor Technologies™. In certain embodiments, imaging module 164 and/or motive module 162 of system 150 can control the light modulating subsystem 330.

In certain embodiments, the imaging device 194 further comprises a microscope 350. In such embodiments, the nest 300 and light modulating subsystem 330 can be individually configured to be mounted on the microscope 350. The microscope 350 can be, for example, a standard research-grade light microscope or fluorescence microscope. Thus, the nest 300 can be configured to be mounted on the stage 344 of the microscope 350 and/or the light modulating subsystem 330 can be configured to mount on a port of microscope 350. In other embodiments, the nest 300 and the light modulating subsystem 330 described herein can be integral components of microscope 350.

In certain embodiments, the microscope 350 can further include one or more detectors 348. In some embodiments, the detector 348 is controlled by the imaging module 164. The detector 348 can include an eye piece, a charge-coupled device (CCD), a camera (e.g., a digital camera), or any combination thereof. If at least two detectors 348 are present, one detector can be, for example, a fast-frame-rate camera while the other detector can be a high sensitivity camera. Furthermore, the microscope 350 can include an optical train configured to receive reflected and/or emitted light from the microfluidic device 320 and focus at least a portion of the reflected and/or emitted light on the one or more detectors 348. The optical train of the microscope can also include different tube lenses (not shown) for the different detectors, such that the final magnification on each detector can be different.

In certain embodiments, imaging device 194 is configured to use at least two light sources. For example, a first light source 332 can be used to produce structured light (e.g., via the light modulating subsystem 330) and a second light source 334 can be used to provide unstructured light. The first light source 332 can produce structured light for optically-actuated electrokinesis and/or fluorescent excitation, and the second light source 334 can be used to provide bright field illumination. In these embodiments, the motive module 164 can be used to control the first light source 332 and the imaging module 164 can be used to control the second light source 334. The optical train of the microscope 350 can be configured to (1) receive structured light from the light modulating subsystem 330 and focus the structured light on at least a first region in a microfluidic device, such as an optically-actuated electrokinetic device, when the device is being held by the nest 300, and (2) receive reflected and/or emitted light from the microfluidic device and focus at least a portion of such reflected and/or emitted light onto detector 348. The optical train can be further configured to receive unstructured light from a second light source and focus the unstructured light on at least a second region of the microfluidic device, when the device is held by the nest 300. In certain embodiments, the first and second regions of the microfluidic device can be overlapping regions. For example, the first region can be a subset of the second region.

In FIG. 3B, the first light source 332 is shown supplying light to a light modulating subsystem 330, which provides structured light to the optical train of the microscope 350 of system 355 (not shown). The second light source 334 is shown providing unstructured light to the optical train via a beam splitter 336. Structured light from the light modulating subsystem 330 and unstructured light from the second light source 334 travel from the beam splitter 336 through the optical train together to reach a second beam splitter (or dichroic filter 338, depending on the light provided by the light modulating subsystem 330), where the light gets reflected down through the objective 336 to the sample plane 342. Reflected and/or emitted light from the sample plane 342 then travels back up through the objective 340, through the beam splitter and/or dichroic filter 338, and to a dichroic filter 346. Only a fraction of the light reaching dichroic filter 346 passes through and reaches the detector 348.

In some embodiments, the second light source 334 emits blue light. With an appropriate dichroic filter 346, blue light reflected from the sample plane 342 is able to pass through dichroic filter 346 and reach the detector 348. In contrast, structured light coming from the light modulating subsystem 330 gets reflected from the sample plane 342, but does not pass through the dichroic filter 346. In this example, the dichroic filter 346 is filtering out visible light having a wavelength longer than 495 nm. Such filtering out of the light from the light modulating subsystem 330 would only be complete (as shown) if the light emitted from the light modulating subsystem did not include any wavelengths shorter than 495 nm. In practice, if the light coming from the light modulating subsystem 330 includes wavelengths shorter than 495 nm (e.g., blue wavelengths), then some of the light from the light modulating subsystem would pass through filter 346 to reach the detector 348. In such an embodiment, the filter 346 acts to change the balance between the amount of light that reaches the detector 348 from the first light source 332 and the second light source 334. This can be beneficial if the first light source 332 is significantly stronger than the second light source 334. In other embodiments, the second light source 334 can emit red light, and the dichroic filter 346 can filter out visible light other than red light (e.g., visible light having a wavelength shorter than 650 nm).

Surface modification. Surfaces of materials, devices, and/or apparatuses for manipulation and storage of biomaterials may have native properties that are not optimized for short and/or long term contact with such material, which may include but is not limited to micro-objects (including but not limited to biological micro-objects such as biological cells), biomolecules, fragments of the biomolecules or biological micro-objects, and any combination thereof. It may be useful to modify one or more surfaces of a material, device or apparatus to decrease one or more undesired phenomena associated with a native surface in contact with one or more biomaterials. In other embodiments, it may be useful to enhance surface properties of the material, device, and/or apparatus to introduce a desired characteristic to the surface, thereby broadening the handling, manipulation or processing capabilities of the material, device, and/or apparatus. To that end, molecules which can modify a surface to either decrease undesired properties or introduce desirable properties are needed.

Compounds useful for modification of surfaces. In various embodiments, a surface modifying compound may include a surface modifying ligand which may be a non-polymeric moiety such as an alkyl moiety or a substituted alkyl moiety, such as a fluoroalkyl moiety (including but not limited to a perfluoroalkyl moiety) which covalently modifies the surface to which it is attached. The surface modifying compound also includes a connecting moiety, which is the group which covalently attaches the surface modifying ligand to the surface, as shown schematically in Equation 1. The covalently modified surface has the surface modifying ligand attached via a linking group LG, which is the product of the reaction of the connecting moiety with functional groups of the surface (including hydroxide, oxide, amine or sulfur).

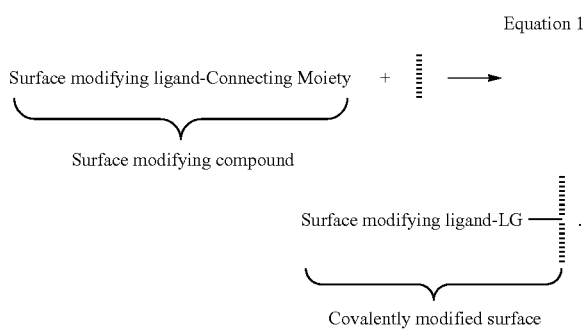

Equation 1

In some embodiments, the surface modifying compound may include carbon atoms forming a linear chain (e.g., a linear chain of at least 10 carbons, or at least 14, 16, 18, 20, 22, or more carbons) and may be an unbranched alkyl moiety. In some embodiments, the alkyl group may include a substituted alkyl group (e.g., some of the carbons in the alkyl group can be fluorinated or perfluorinated). In some embodiments, the alkyl group may include a first segment, which may include a perfluoroalkyl group, joined to a second segment, which may include a non-substituted alkyl group, where the first and second segments may be joined directly or indirectly (e.g., by means of an ether linkage). The first segment of the alkyl group may be located distal to the linking group, and the second segment of the alkyl group may be located proximal to the connecting moiety.

In various embodiments, the surface modifying compound may have a structure of Formula I:

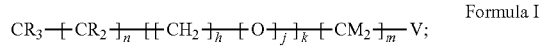

Formula I wherein a connecting moiety V is —P(O)(OH)Q- or —Si(T)$_2$W; W is -T, —SH, or —NH$_2$ and is the moiety configured to connect to the surface; Q is —OH and is the moiety configured to connect to the surface; and T is OH, OC$_{1-3}$alkyl, or Cl. R is hydrogen or fluorine and M is hydrogen or fluorine. Each instance of h independently is an integer of 2 or 3; j is 0 or 1; k is 0 or is 1; m is 0 or an integer of 1 to 25; and n is 0 or an integer of 1 to 25. In some other embodiments, the sum of (n+[(h+j)·k]+m) may be an integer of 11 to 25. In some embodiments, M is hydrogen. In various embodiments, m is 2. In some embodiments, k is 0. In other embodiments, k is 1. In various embodiments, j is 1. For the compound of Formula I, when k is an integer of 1, then m may be at least 2 and M is hydrogen. For the compound of Formula I, when k is 0 and R is fluorine, then m may be at least 2 and M is hydrogen.

In various embodiments, where the surface modifying compound has a structure of Formula I, the connecting moiety V may be —Si(T)$_2$W, where T and W are defined as above. W may be OC$_{1-3}$alkyl, or Cl. W may be methoxy, ethoxy or propoxy. In some embodiments, W may be methoxy. T may be may be OC$_{1-3}$alkyl, or Cl. In various embodiments, connecting moiety V is —Si(OMe)$_3$. In various other embodiments, V may be —P(O)(OH)Q, where Q is OH.

The surface modifying compound of Formula 1 may have a preferred range of number of atoms making up the linear backbone of the compound. As defined above each of the segments that make up the compound of Formula 1 may have a range of sizes. Accordingly, a compound of Formula 1 may have repeating units as defined above such that (n+[(h+j)·k]+m) is equal to 25, which would yield a total length of 26 atoms, including the terminal CR$_3$— group, attached to the connecting moiety. In the instance of (n+[(h+j)·k]+m) equal to 25, a variety of different compositions can be encompassed. For instance, the segment —[CR$_2$]$_n$— may have n=23; —[(CH$_2$)$_h$—(O)$_j$]$_k$— may have k=0; and —[CM$_2$]$_m$— may have m=2. Another instance having the same total (n+[(h+j)·k]+m) equal to 25, may have segment —[CR$_2$]$_n$— where n=6; —[(CH$_2$)h-(O)j]k- where k=3, and includes j=1 and h=2; and —[CM$_2$]$_n$— may have m=4.

In some embodiments, the sum of (n+[(h+j)·k]+m) may be 11, 13, 15, 17, or 21. In other embodiments, the sum of (n+[(h+j)·k]+m) may be 15 or 17. In yet other embodiments, the sum of (n+[(h+j)·k]+m) may be 13 or 15.

In some embodiments, one or more ether linkages may be present in the compound of Formula I. In some embodiments, j may be 1. In some embodiments, where k and j are both 1, m may be at least two.

In yet other embodiments, backbone carbons may be fluorinated. In some embodiments, backbone carbons may be perfluorinated, where each R of CR$_3$—, and/or —[CR$_2$]$_n$— and/or —[CM$_2$]$_m$— may be fluorinated. In some embodiments, a section of the compound may have carbon backbone atoms that are fluorinated and other sections of the compound may have carbon backbone atom that are substituted with hydrogen. For example, in some embodiments, CR$_3$— and —[CR$_2$]$_n$— segments may have fluorine nonbackbone substituents (e.g., R is fluorine) while —[CM]$_m$- segments may have hydrogen nonbackbone substituents (e.g., M is hydrogen). In some embodiments, when R is fluorine, then k is 0. In other embodiments, R may be fluorine and k is 1, j is 1 and his 2. In various embodiments, M may be hydrogen.

In yet other embodiments, the compound of Formula 1 may be synthesized from hydrosilation of an olefin as described below, where m is at least two and M is hydrogen. In some embodiments, m is 2 and M is hydrogen.

Some of the variety of compounds of Formula I may be more readily seen in subsets of compounds described in the following formulae, but these formulae are in no way limiting to the breadth of Formula I.

In some embodiments, the compound of Formula I may include a compound of Formula 110:

$$CH_3(CH_2)_m Si(OC_{1-3}alkyl)_3; \qquad \text{Formula 110}$$

where m is an integer of 9 to 23. In some embodiments, m may be 11, 13, 15, 17, or 19. In some other embodiments m may be 13 or 15.

In other embodiments, the compound of Formula I may include a compound of Formula 111:

$$CF_3(CF_2)_n(CH_2)_2 Si(OC_{1-3}alkyl)_3; \qquad \text{Formula 111}$$

where n may be an integer of 9 to 22. Alternatively, n may be an integer of 11 to 17. In some other embodiments, n may be 9, 11, 13, or 15. In some embodiments, n may be 13 or 15.

In yet other embodiments, the compound of Formula I may include a compound of Formula 112:

$$CR_3(CR_2)_n(CH_2)_hO(CH_2)_m Si(OC_{1-3}alkyl)_3; \qquad \text{Formula 112}$$

where n is an integer of 3 to 19; h is an integer of 2 or 3; and m is an integer of 2 to 18. In some embodiments, R may be fluorine. In some embodiments n may be an integer of 3 to 11, h may be 2, and m may be an integer of 2 to 15.

Alternatively, the compound of Formula I may include a compound of Formula 113:

$$CR_3(CR_2)_n(CM_2)_m P(O)(OH)_2; \qquad \text{Formula 113}$$

where n is an integer of 3 to 21; and m is an integer of 2 to 21. In some embodiments of the compound of Formula 113, R may be fluorine. In some embodiments, M may be hydrogen. In various embodiments, n may be 5, 7, 9, or 11. In other embodiments, m may be 2, 4, 5, 7, 9, 11 or 13.

Surfaces for modification. A surface capable of being modified by the surface modifying compounds described herein, including a compound of Formula I, may be a metal, metal oxide, glass or polymer. Some materials that may have a covalently modified surface introduced therein in may include but not be limited to silicon and its oxides, silicones, aluminum or its oxide thereof (Al$_2$O$_3$), Indium Tantalum Oxide (ITO), titanium dioxide (TiO$_2$), zirconium oxide (ZrO2), hafnium (IV) oxide (HfO$_2$), tantalum (V) oxide (Ta$_2$O$_5$), or any combination thereof. The surface may be a wafer or sheet of these materials, or may be incorporated within an apparatus or device. In some embodiments, the surface including any of these materials may be incorporated within a microfluidic device as described herein.

Polymers may include any suitable polymer. A suitable polymer may include but is not limited to (e.g. rubber, plastic, elastomer, silicone, organosilicone, such as polydimethylsiloxane ("PDMS"), or the like), which can be gas permeable. Other examples can include molded glass, a patternable material such as a silicone polymer (e.g. photo-patternable silicone or "PPS"), photo-resist (e.g., an epoxy-based photo-resist such as SU8), or the like. In other embodiments, a surface of a material such as a natural fiber or wood may be functionalized by the surface modifying compounds described herein, including a compound of Formula I, to introduce a covalently modified surface.

The surface to be modified may include a nucleophilic moiety including but not limited to hydroxide, amino and thiol. The nucleophilic moiety (e.g., hydroxide (in some embodiments referred to as oxide)) on the surface may react with the surface modifying compounds described herein, including a compound of Formula I, to covalently link the surface modifying ligand to the surface, via a siloxy linking group or phosphonate linking group, to provide the functionalized surface. The surface to be modified may include native nucleophilic moieties, or may be treated with reagents (e.g., piranha solution) or by plasma treatment to introduce nucleophilic moieties (e.g., hydroxide (alternatively referred to as oxide)).

In some embodiments, the surface may be formed from any of the above materials, singly or in any combination. The surface may include a semiconductor substrate. In various embodiments, the surface including a semiconductor substrate may further include a DEP or EW substrate as described herein. In some embodiments, the surface including a semiconductor substrate having a DEP or EW substrate may be part of a microfluidic device as described herein.

In some embodiments, the modified surface may be at least one inward-facing surface of a microfluidic device as described herein. The at least one surface may be part of the flow region of the microfluidic device (which may include a channel) or may include a surface of an enclosed structure such as a pen, which may include a sequestration pen as described herein.

Covalently modified surface. A covalently modified surface may include a surface modifying ligand, which may be a non-polymeric moiety such as an alkyl moiety, a substituted alkyl moiety, such as a fluoroalkyl moiety (including but not limited to a perfluoroalkyl moiety) and may be any surface modifying ligand described above, which is covalently bound to the surface via a linking group, which is the moiety resultant from reaction of the connecting moiety with the surface. The linking group may be a siloxy linking group or a phosphonate linking group.

In some embodiments, the surface modifying ligand may include carbon atoms forming a linear chain (e.g., a linear chain of at least 10 carbons, or at least 14, 16, 18, 20, 22, or more carbons) and may be an unbranched alkyl moiety. In some embodiments, the alkyl group may include a substituted alkyl group (e.g., some of the carbons in the alkyl group can be fluorinated or perfluorinated). In some embodiments, the alkyl group may include a first segment, which may include a perfluoroalkyl group, joined to a second segment, which may include a non-substituted alkyl group, where the first and second segments may be joined directly or indirectly (e.g., by means of an ether linkage). The first segment of the alkyl group may be located distal to the linking group, and the second segment of the alkyl group may be located proximal to the linking group.

Covalently modified surface of Formula II. In some embodiments, a covalently modified surface has a structure of Formula II:

Formula II

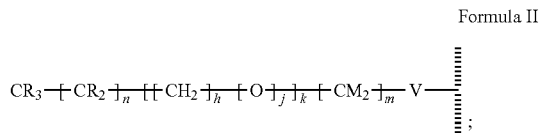

wherein is the surface; V is —P(O)(OY)W— or —Si(OZ)$_2$W. W is —O—, —S—, or —NH— and connects to the surface. Z is a bond to an adjacent silicon atom attached to the surface or is a bond to the surface. Y is a bond to an adjacent phosphorus atom attached to the surface or is a bond to the surface. For the covalently modified surface of Formula II, R, M, h, j, k, m, and n are as defined above. When k is an integer of 1, then m is at least 2 and M is hydrogen. When k is 0 and R is fluorine, then m is at least 2 and M is hydrogen. The covalently modified surface of Formula II can be described as a surface modifying ligand attached via a linking group LG, as in Formula IIA, where LG is linked to the surface:

Formula IIA

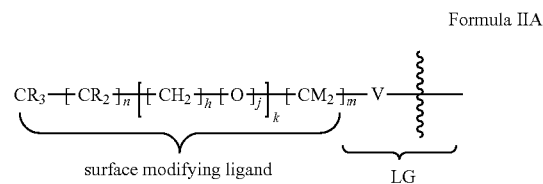

The covalently modified surface may include any surface of Formula II, in any combination, as described above for the surface modifying compound of Formula I.

In some embodiments, the covalently modified surface of Formula II may be a surface of Formula 210:

Formula 210

wherein is the surface, oxygen attached to the silicon atom is also bound to the surface, and m is an integer of 11 to 23. In some embodiments, m may be 11, 13, 15, 17, or 19. In some other embodiments m may be 13 or 15.

In some other embodiments, the covalently modified surface of Formula II may be a surface of Formula 211:

Formula 211

wherein is the surface, oxygen attached to the silicon atom is also bound to the surface, and n may be an integer of 9 to 22. Alternatively, n may be an integer of 11 to 17. In some other embodiments, n may be 7, 9, 11, 13, or 15. In some embodiments, n may be 13 or 15.

In yet other embodiments, the covalently modified surface of Formula II may be a surface of Formula 212:

Formula 212

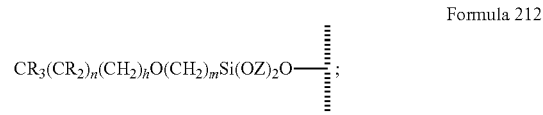

wherein is the surface, oxygen attached to the silicon atom is also bound to the surface, and n is an integer of 3 to 21, h is an integer of 2 or 3, and m is an integer of 2 to 21. In some embodiments, R may be fluorine. In some embodiments, n may be an integer of 3 to 11, h may be 2, and m may be an integer of 2 to 15.

Alternatively, the covalently modified surface of Formula II may be a surface of Formula 213:

Formula 213

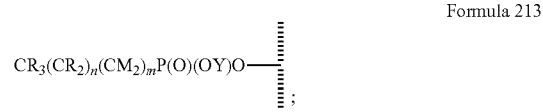

wherein ≡ is the surface, oxygen attached to the phosphorus atom is also bound to the surface, n is an integer of 3 to 21 and m is an integer of 2 to 21. In some embodiments of the compound of Formula 113, R may be fluorine. In some embodiments, M may be hydrogen. In various embodiments, n may be 5, 7, 9, or 11. In other embodiments, m may be 2, 4, 5, 7, 9, 11 or 13.

In some embodiments, the microfluidic device comprises a flow region fluidically connected to a first inlet and a first outlet, the flow region configured to contain a flow of a first fluidic medium. The microfluidic device may include one or more chambers opening to the flow region. The covalently modified surface may be a covalently modified substrate of the microfluidic device and may underlay the flow region and/or at least one chamber. In some embodiments, all or substantially all the interior surfaces of the microfluidic device configured to face fluid have a covalently modified surface of Formula II.

Figure 2H:
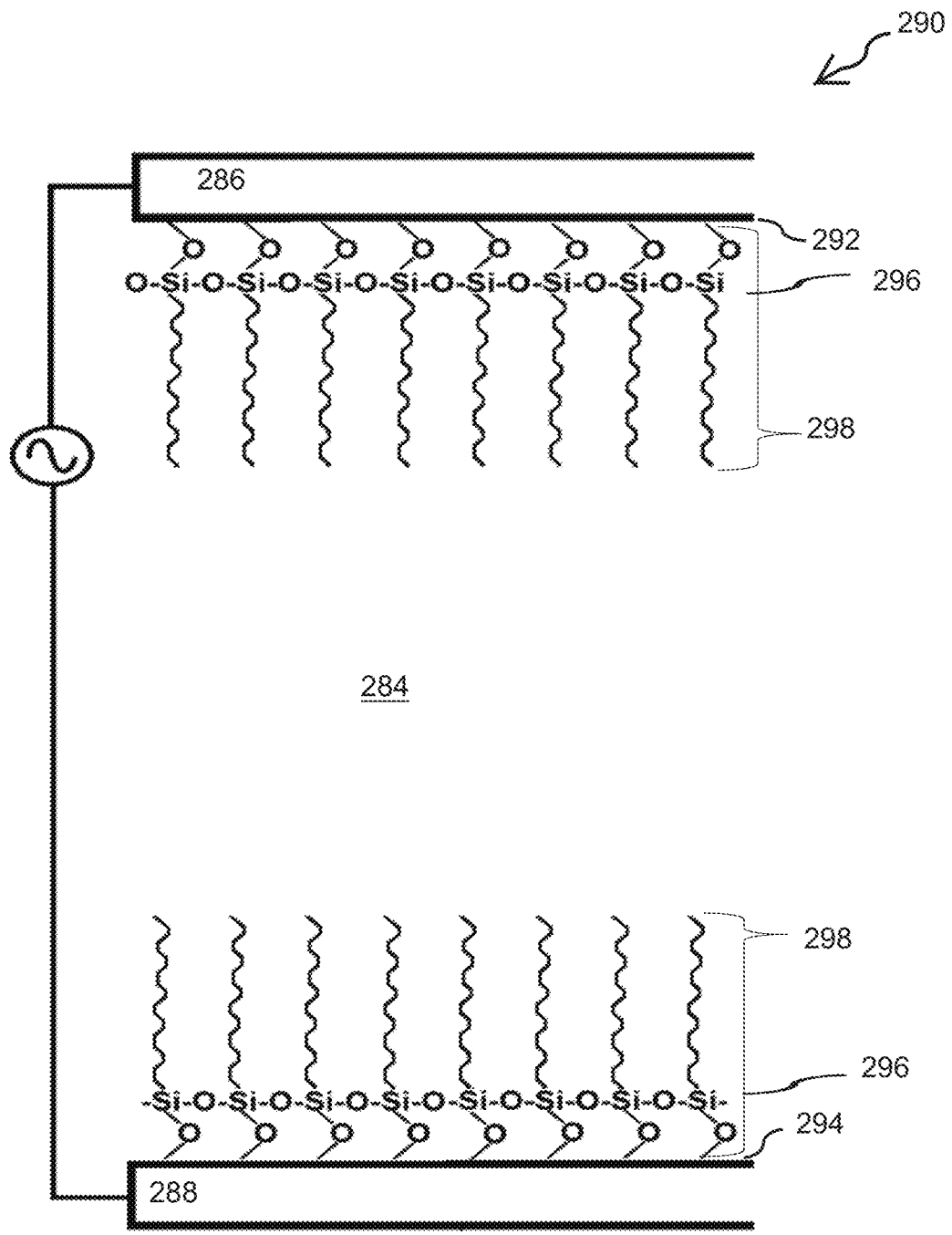
FIG. 2H illustrates a coated surface of the microfluidic device according to an embodiment of the invention.

FIG. 2H depicts a cross-sectional view of a microfluidic device 290 comprising an exemplary covalently modified surface 298. As illustrated, the covalently modified surface 298 (shown schematically) can comprise a monolayer of densely-packed molecules covalently bound to both the inner surface 294 of the substrate 286 and the inner surface 292 of the cover 288 of the microfluidic device 290. The covalently modified surface s 298 can be disposed on substantially all inner surfaces 294, 292 proximal to, and facing inwards towards, the enclosure 284 of the microfluidic device 290, including, in some embodiments and as discussed above, the surfaces of microfluidic circuit material (not shown) used to define circuit elements and/or structures within the microfluidic device 290. In alternate embodiments, the covalently modified surface 298 can be disposed on only one or some of the inner surfaces of the microfluidic device 290.

In the embodiment shown in FIG. 2H, the covalently modified surface 298 comprises a monolayer of alkyl-terminated siloxane molecules, each molecule covalently bonded to the inner surfaces 292, 294 of the microfluidic device 290 via a siloxy linker 296. For simplicity, additional silicon oxide bonds are shown linking to adjacent silicon atoms, but the invention is not so limited. In some embodiments, the covalently modified surface 298 can comprise a fluoroalkyl group (e.g. a fluorinated alkyl group or a perfluorinated alkyl group) at its enclosure-facing terminus (i.e. the portion of the monolayer of the surface modifying ligand 298 that is not bound to the inner surfaces 292, 294 and is proximal to the enclosure 284). While FIG. 2H is discussed as having an alkyl-terminated modified surface, any suitable surface modifying compound may be used, as described herein.

Native surface. The at least one surface of the microfluidic device to be modified may be glass, metal, metal oxide or polymer. Some materials that may be incorporated within the microfluidic device and may be modified to have a covalently modified surface of Formula II introduced therein in may include but not be limited to silicon and its oxides, silicones, aluminum or its oxide thereof ($Al_2O_3$), Indium Tantalum Oxide (ITO), titanium dioxide ($TiO_2$), zirconium oxide (ZrO2), hafnium (IV) oxide ($HfO_2$), tantalum (V) oxide ($Ta_2O_5$), or any combination thereof. Polymers may include any suitable polymer. A suitable polymer may include but is not limited to (e.g. rubber, plastic, elastomer, silicone, organosilicone, such as polydimethylsiloxane ("PDMS"), or the like), which can be gas permeable. Other examples can include molded glass, a patternable material such as a silicone polymer (e.g. photo-patternable silicone or "PPS"), photo-resist (e.g., an epoxy-based photo-resist such as SU8), or the like.

Physical and performance properties of the covalently modified surface. In some embodiments, the covalently modified surface may have increased hydrophobic character. The increased hydrophobic character of the modified surface may prevent fouling by biomaterials. Surface fouling, as used herein, refers to the amount of material indiscriminately deposited on the surface of the microfluidic device, which may include permanent or semi-permanent deposition of biomaterials such as protein and degradation products, nucleic acids, and respective degradation products. Such fouling can increase the amount of adhesion of biological micro-objects to the surface. In other embodiments, increased hydrophobic character of a covalently modified surface may decrease adhesion of biological micro-objects on the surface, independently of adhesion initiated by surface fouling.

Modification of the surface may increase the durability, functionality, and/or biocompatibility of the surface. Each of these characteristics may further benefit the viability (including growth rate and/or cell doubling rate), nature of the colony formed upon a covalently modified surface as described herein, including a surface having a structure of Formula II, or portability (including viability upon export) of micro-objects or biomolecules upon the modified surface and within devices and/or apparatuses having a covalently modified surface.

In some embodiments, the covalently modified surface, which may be any surface as described herein, including a surface of Formula II, may have a thickness of less than 10 nm (e.g., less than about 7 nm, less than about 5 nm, or about 1.5 to 3.0 nm). This may provide an advantageously thin layer on the modified surface, particularly in contrast with other hydrophobic materials such as CYTOP®, a perfluoro tetrahydrofuranyl polymer which is spin-coated yielding a typical thickness of about 30 to 50 nm. Data shown in Table 1 is for a silicon/silicon oxide surface which is treated to have a covalently modified surface as shown in the table. Contact angle measurements were obtained using the static sessile drop method. (Drelich, J. Colloid Interface Sci. 179, 37-50, 1996.) Thickness was measured by ellipsometry.

Contact angle hysteresis measurements were performed using a Biolin Scientific contact angle goniometer. Chemically modified OEW surfaces were placed in a bath of 5 cSt silicone oil encased in a transparent holder. A phosphate buffered saline (PBS) droplet was then dispensed onto the surface in the oil. A platinum (Pt) wire electrode was inserted into the droplet, and the sessile water contact angle was measured. Next, an applied AC voltage of 50 Vppk at 30 kHz frequency was applied between the OEW substrate and the Pt wire inserted into the PBS droplet for 10 seconds. Next, the applied voltage was removed, and the contact angle was measured again. The contact angle hysteresis was calculated by subtracting the contact angle at zero bias after applying the 50 Vppk AC voltage from the original contact angle at zero bias before applying the voltage.

TABLE 1

Physical data for selected surfaces.

| No. | Modified Surface | Contact Angle (water or aqueous solution) | Contact angle hysteresis | Thickness |
| --- | --- | --- | --- | --- |
| 201 | $CH_3(CH_2)_{17}\text{-}Si(OT)_2O\text{-}(surface)$ | 110-112° | 5°, less than 10° | Approx. 2 nm |
| 202 | $CF_3(CF_2)_{13}(CH_2)_2Si(OT)_2O\text{-}(surface)$ | 110-115° | data | Approx. 2 nm |
| 203 | $CF_3(CF_2)_7(CH_2)_2Si(OT)_2O\text{-}(surface)$ | 110-115° | >10° | Approx 1 nm |
| 204 | $CH_3(CH_2)_{21}Si(OT)_2O\text{-}(surface)$ | 110-112° | n/a | Approx. 2-2.5 nm |
| 205 | $CH_3(CH_2)_{15}Si(OT)_2O\text{-}(surface)$ | 110-112° | >10° | n/a |
| 206 | $CF_3(CF_2)_5(CH_2)_2O(CH_2)_{11}Si(OT)_2O\text{-}(surface)$ | 110-114° | n/a | Approx. 2 nm |
| 207 | $CH_3(CH_2)_{17}P(O)(OQ)O\text{-}(surface)$ | 110° | n/a | n/a |
| 208 | $CF_3(CF_2)_7(CH_2)_{11}Si(OT)_2O\text{-}(surface)$ | 113° | n/a | Approx. 2 nm |
| 209 | $CF3(CF2)_{11}(CH_2)_2\ Si(OT)_2O\text{-}(surface)$ | 112° | n/a | Approx. 1.5-2 nm |

T and Q are as described above.

The contact angles observed for modified surfaces are in contrast to the contact angle for water on a plasma cleaned silicon surface of less than 10 degrees. Each of these surfaces is less wettable than that of the native silicon/silicon oxide surface.

Other analytical methods suitable to characterize the surface can include infrared spectroscopy and/or X-ray photoelectron spectroscopy.

Another desirable characteristic of the modified surfaces of the invention is a lack of autofluorescence, which can be dependent upon the chemical nature of the surface modifying compound.

In some embodiments, the covalently modified surface described herein, including a surface of Formula II, may form a monolayer. The uniformity and evenness of a monolayer modified surface may provide advantageous performance, particularly if the monolayer modified surface has other functional attributes. For example, the covalently modified surface described herein, including a surface of Formula II, may also include an electrode activation substrate, and optionally further may include a dielectric layer, as may be found in materials, devices and/or apparatuses having a dielectrophoresis configuration or an electrowetting configuration. The lack of unsaturation of the perfluoroalkyl moieties of the modified surface can minimize "charge trapping" compared to a monolayer containing, for example olefinic or aromatic moieties. Additionally, the densely packed nature of the monolayer formed in the surface described herein, including a surface of Formula II, may minimize the potential for cations to be driven through the monolayer to the underlying metal, metal oxide, glass or polymer substrate. Without being limited by theory, the disruption of the substrate surface by addition of cations to substrate composition may disrupt the electrical properties of the substrate, thereby reducing its ability to function electrokinetically.

Further, the ability to introduce the modified surface via a covalent linkage may increase the dielectric strength of the modified surface and protect the underlying material from breakdown under application of an electric field. The uniformity and thinness of an dielectrophoretic or electrowetting surface of a material, device and/or apparatus having a covalently modified surface described herein, including a surface of Formula II, may further provide advantageous benefit for such modified dielectrophoretic and/or electrowetting surface when the material, device and/or apparatus is optically actuated.

Methods of preparation of the covalently modified surface. A surface of a material that may be used as a component of a device or apparatus may be modified before assembly of the device or apparatus. Alternatively, partially or completely constructed device or apparatus may be modified such that all surfaces that will contact biomaterials including biomolecules and/or micro-objects (which may include biological micro-objects) are modified at the same time. In some embodiments, the entire interior of a device and/or apparatus may be modified, even if there are differing materials at different surfaces within the device and/or apparatus. In some embodiments, the partially or completely constructed device and/or apparatus may be a microfluidic device as described herein, or a component thereof.

The surface to be modified may be cleaned before modification to ensure that the nucleophilic moieties on the surface are freely available for reaction, e.g., not covered by oils or adhesives. Cleaning may be accomplished by any suitable method including treatment with solvents including alcohols or acetone, sonication, steam cleaning and the like. In some embodiments, the surface to be modified is treated with oxygen plasma treatment which removes contaminants, which at the same time, can introduce additional oxide (e.g., hydroxide) moieties on the surface. This can advantageously provide more sites for modification on the surface, thereby providing a more closely packed modified surface layer.

The surface to be modified may be cleaned before modification to ensure that the nucleophilic moieties on the surface are freely available for reaction, e.g., not covered by oils or adhesives. Cleaning may be accomplished by any suitable method including treatment with solvents including alcohols or acetone, sonication, steam cleaning and the like. In some embodiments, the surface to be modified is treated with oxygen plasma treatment which removes contaminants, which at the same time, can introduce additional oxide (e.g., hydroxide) moieties on the surface. This can advantageously provide more sites for modification on the surface, thereby providing a more closely packed modified surface layer.

In some embodiments, the method of covalently modifying a surface includes the steps of: contacting the surface with a compound of Formula I:

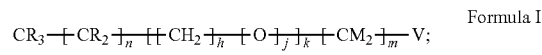

Formula I where V is —P(O)(OH)Q or —Si(T)$_2$W. W is -T, —SH, or —NH$_2$ and is the moiety configured to connect to the surface. Alternatively, when V is —P(O)(OH)Q, Q is —OH and is the moiety configured to connect to the surface. T is OH, OC$_{1-3}$alkyl, or Cl. Each of R, M, h, j, k, m, and n are as defined above for the compound of Formula I. The sum of (n+[(h+j)·k]+m) is an integer of 11 to 25. In various embodiments, when k is an integer of 1, then m is at least 2 and M is hydrogen; and when k is 0 and R is fluorine, then m is at least 2 and M is hydrogen. The compound of Formula I reacts with a nucleophilic moiety of the surface; and the covalently modified surface is formed. Any combination or subcombination of the compound of Formula I may be used, as described above.

In various embodiments of the method, the covalent modified surface so formed may be a monolayer.

In some embodiments of the method, the compound of Formula I may be a compound of Formula 110:

$$CH_3(CH_2)_m Si(OC_{1-3}alkyl)_3; \qquad \text{Formula 110}$$

where m is an integer of 9 to 23. In some embodiments, m may be 11, 13, 15, 17, or 19. In some other embodiments m may be 13 or 15.

In other embodiments of the method, the compound of Formula I may be a compound of Formula 111:

$$CF_3(CF_2)_n(CH_2)_2 Si(OC_{1-3}alkyl)_3; \qquad \text{Formula 111}$$

where n is an integer of 9 to 22. Alternatively, n may be an integer of 11 to 17. In other embodiments, n may be an integer of 11 to 17. In some other embodiments, n may be 9, 11, 13, or 15. In some embodiments, n may be 13 or 15.

In yet other embodiments of the method, the compound of Formula I may be a compound of Formula 112:

$$CR_3(CR_2)_n(CH_2)_h O(CH_2)_m Si(OC_{1-3}alkyl)_3; \qquad \text{Formula 112}$$

where n is an integer of 3 to 21; h is an integer of 2 or 3; and m is an integer of 2 to 21. In some embodiments, R may be fluorine. In some embodiments n may be an integer of 3 to 11, h may be 2, and m may be an integer of 2 to 15.

Alternatively, the surface may be contacted by a compound of Formula I which may be a compound of Formula 113:

$$CR_3(CR_2)_n(CM_2)_m P(O)(OH)_2; \qquad \text{Formula 113}$$

where n is an integer of 3 to 21; and m is an integer of 2 to 21. In some embodiments of the compound of Formula 113, R may be fluorine. In some embodiments, M may be hydrogen. In various embodiments, n may be 5, 7, 9, or 11. In other embodiments, m may be 2, 4, 5, 7, 9, 11 or 13.

The contacting step may be performed by contacting the surface with a liquid solution containing the compound of Formula I. For example, surfaces may be exposed to solutions containing 0.01 mM, 0.1 mM, 0.5 mM, 1 mM, 10 mM, or 100 mM of the compound of Formula I. The reaction may be performed at ambient temperature and may be carried out for a period of time in the range of about 2 h, 4 h, 8 h, 12 h, 18 h, 24 h, or any value inbetween. Examples of solvents include but are not limited to: toluene, 1,3 bistrifluorobenzene, or Fluorinert™ (3M) fluorinated solvents. An acid such as acetic acid may be added to the solution to increase the reaction rate by promoting hydrolysis of the trialkoxy groups, if present.

Alternatively, the surface may be contacted with a vapor phase containing the compound of Formula I. In some embodiments, when the reacting step is performed by contacting the surface with the compound of Formula I in the vapor phase, a controlled amount of water vapor is also present. The controlled amount of water vapor may be provided by placing a preselected amount of magnesium sulfate heptahydrate in the same chamber or enclosure with the object having the surface to be modified. In other embodiments, a controlled amount of water may be introduced into the reaction chamber or enclosure via an external water vapor feed. The reaction may take place under reduced pressure, relative to atmospheric pressure. In some embodiments, the reduced pressure may be 100 Torr or less. In other embodiments, the reduced pressure may be less than 10 Torr or less than 1 Torr.

The reaction may be conducted at a temperature in a range from about 150° C. to about 200° C. In various embodiments, the reaction may be conducted at a temperature of about 150° C., 155° C., 160° C., 165° C., 170° C., 175° C., 180° C., 185° C., or about 190° C. The reaction may be permitted to continue for about 2 h, 6 h, 8 h, 18 h, 24 h, 48 h, 72 h, 84 h, or more.

In some embodiments, the covalently modified surface may have a structure of Formula II:

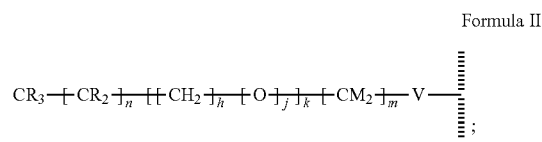

Formula II wherein R, M, n, h, j, k, m and V are as described above, in any combination. In some embodiments of the method, the covalently modified surface may have a formula of Formula 210, 211, 212, or 213 as described above, having any combination of permissible elements for each formula.

In various embodiments of the method, the surface may include a nucleophilic moiety selected from the group consisting of hydroxide, amino and thiol. The surface may be a metal, metal oxide, glass, polymer, or any combination thereof. The metal surface may include silicon, silicon oxide, hafnium oxide, indium tantalum oxide, alumina, or any combination thereof.

In various embodiments of the method, wherein the step of forming covalently modified surface may be performed on a DEP substrate or a EW substrate. The step of forming the covalently modified surface may include forming the covalently modified surface on at least one surface of a microfluidic circuit element of a microfluidic device. The microfluidic circuit elements may include walls, flow regions, pens, and electrode activation substrates, including DEP or EW substrates. The surface within the microfluidic circuit which may be covalently modified, may be all or substantially all of the surfaces facing fluid bearing portions of a microfluidic device. For example, in microfluidic devices 200, 230 the inner surface of the top electrode 210, the upper surface of the electrode activation substrate 206, the surfaces of the microfluidic circuit material 116 (See FIGS. 1B, 1C, 2A, 2B), all of which face the microfluidic channel 122 and pens 244, 246, 248 may be modified. Similarly, in FIGS. 2D-2F, the inner surfaces of microfluidic circuit material 260, surfaces of isolation structures 272 which define the sequestration pen 266, or all the surfaces facing the microfluidic circuit 262 may be modified covalently by the methods described herein.

Immiscible medium. Movement of aqueous droplets upon the surface of the substrate may be performed within a water immiscible fluidic medium distributed regionally within one or more flow regions (which may include flow channels) and, if present, within chambers fluidically connected to the flow regions. The water immiscible fluidic medium may have a kinematic viscosity greater than that of a droplet of pure water. The water immiscible fluidic medium may have a kinematic viscosity in the range of about 1 Centistoke (cSt) to about 15 cSt, where 1 cSt is equal to 1 millipascal or to 1 centipoise (CPS). In some embodiments, the water immiscible fluidic medium may have a viscosity in the range of about 3 cSt to about 10 cSt or about 3 cSt to about 8 cSt. The water immiscible fluidic medium may be nonflammable at temperatures of at least 100° C. The water immiscible fluidic medium may be non-toxic to living biological cells over the duration of time that biological cells are processed, cultured or stored within the aqueous droplet within the water immiscible fluidic medium.

The water immiscible fluidic medium may have low or very little solubility in water. The water immiscible fluidic medium may dissolve less than about 5%, 4%, 3%, 2%, 1% or less than 1% of its total volume of water, when contacted with a layer of water (e.g, partitioning with water). The water immiscible fluidic medium may not solubilize more than about 5%, about 10%, about 15%, about 20%, about 25%, or about 30% of the volume of an aqueous droplet present within the water immiscible fluidic medium at a temperature in the range of about 25° C. to about 38° C. In some embodiments, the water immiscible fluidic medium solubilizes less than about 20% of the volume of an aqueous droplet present within the water immiscible fluidic medium.

The water immiscible fluidic medium may include at least one organic or organosilicon compound having a backbone structure comprising atoms selected from carbon, silicon, and oxygen. In some embodiments, the water immiscible fluidic medium may include more than one organic/organosilicon compound, wherein the more than one compound is a polymeric organic/organosilicon compound having a range of molecular weights of the subunits of the polymeric compound. For example, the polymeric organic/organosilicon compound may have two different sub-units making up the polymer (e.g., a copolymer) and each of the two different sub-units may be present in a range of repeats, having a generic formula AaBb where A and B are two different polymer subunits, and a and b are the number of repeats of each subunit. The number of repeats, a and b, may not be a single integer but may be a range of repeat units.

In other embodiments, the water immiscible fluidic medium including more than one organic/organosilicon compound, may include a mixture of organic compounds, a mixture of organosilicon compounds, or any combination thereof. The water immiscible fluidic medium may include any suitable mixture of compounds having different chemical structures and/or molecular weights that will provide suitable performance.

A compound of the water immiscible fluidic medium may have a molecular weight of less than about 1000 Da, about 700 Da, about 500 Da, or about 350 Da. In other embodiments, the compound(s) of the water immiscible medium may have a higher molecular weight than about 1000 Da and still provide suitable performance.

In various embodiments, the organic/organosilicon compound(s) of the water immiscible fluidic medium may have a backbone structure where the atoms making up the backbone are carbon, silicon or oxygen. The substituents of the backbone carbons may be hydrogen or fluorine. In some embodiments, the water immiscible fluidic medium may include one or more organosilicon compounds, where the backbone of the organosilicon compound(s) may include silicon and oxygen atoms. The silicon atoms of the organosilicon compound(s) may have carbon substituents, which in turn may have hydrogen or fluorine substituents. In some embodiments, the carbon substituents of an organosilicon compound may be all fluorine (e.g., perfluorinated). In other embodiments, the carbon substituents of an organosilicon compound may be partially fluorinated. In various embodiments, the substituents of carbon atoms of an organosilicon compound may be no more than about 90% fluorine, 80% fluorine, 70% fluorine, 60% fluorine, 50% fluorine, 40% fluorine, 30% fluorine, 20% fluorine or less.

In other embodiments, the organic compound(s) of the water immiscible fluidic medium may have a backbone structure where the atoms making up the backbone are carbon or oxygen. In some embodiments, the substituents of the backbone carbons may be hydrogen or fluorine. In other embodiments, the substituents of the backbone carbons may include an oxygen containing moeity such as an ether, carbonyl, or carbonate component. In some embodiments, the organic compound(s) of the water immiscible fluidic medium may have an all-carbon backbone structure. In some embodiments of the all-carbon backbone structure of the organic compound(s) of the water immiscible fluidic medium may have all fluorine substituents on the carbon atoms (e.g., is perfluorinated). In other embodiments, the substituents of an organic compound may be partially fluorinated (e.g., is not perfluorinated). In various embodiments, the substituents of carbon atoms of an organic compound, including a compound having an all-carbon backbone, may be no more than about 90% fluorine, 80% fluorine, 70% fluorine, 60% fluorine, 50% fluorine, 40% fluorine or less. In some embodiments, a suitable organic compound of the water immiscible fluidic medium may include or may be a monofluoro-substituted hydrocarbon such as 1-fluorooctane, 1-fluorodecane, 1-fluorododecane, or 1-fluorotetradecane.

In other embodiments, the organic compound(s) of the water immiscible fluidic medium may have no fluorine substituents on the carbons, but may have hydrogen substituents. In some embodiments, the organic compound(s) of the water immiscible fluidic medium may have unsaturated carbon-carbon linkages, e.g., an olefinic group either within the backbone carbons or at a terminal position.

In some embodiments, selection of an appropriate compound to be included in the water immiscible fluidic medium will include consideration of other properties of the compound. In various embodiments, a compound suitable for use within a water immiscible fluidic medium will not autofluoresce when illuminated by a laser, structured light projected into a microfluidic device, or daylight/laboratory lighting.

In other embodiments, the nature of the covalently modified hydrophobic surface will influence the selection of suitable compounds for use within the water immiscible fluidic medium. For example, a covalently modified surface may be sufficiently hydrophobic such that a droplet of water within a perfluorinated water immiscible fluidic medium may demonstrate sufficiently high surface tension that the droplet of water may not be movable using an opto-electrowetting configuration as described herein.

In some other embodiments, the nature of the microfluidic circuit material may influence selection of suitable compounds for use within the water immiscible fluidic medium. Swelling of the circuit material by the water immiscible fluidic medium may be kept within acceptable limits. For example, in some embodiments, if the microfluidic circuit material includes SU8 or a photopatternable aryl-substituted organosilicone, then linear hydocarbon, linear fluorocarbon, or carbon-backbone compounds including cyclic, aryl or heteroaryl groups may be selected for use.

In other embodiments, the microfluidic circuit material may include other materials such as a photopatternable organosilicone containing no aryl substitution, and swelling may be limited to acceptable limits by use of different compounds in the water immiscible fluidic medium. For example, swelling of less than about 40%, 30%, 20%, or 10% compared to pre-exposure to the water immiscible fluidic medium may be acceptable. However, in some embodiments, a compound within the water immiscible fluidic medium that causes swelling may still be selected for use.

In some embodiments, the compound of the water immiscible fluidic medium may be an organic compound having a backbone containing carbon or oxygen atoms. In some embodiments, the organic compound may have a backbone that contains carbon atoms and does not contain oxygen atoms, and further where the carbon atom backbone is branched. In various embodiments, the branched carbon atom backbone of the organic compound of the water immiscible fluidic medium is acyclic. The organic compound of the water immiscible fluidic medium having a branched carbon backbone may further not contain any cyclized moiety.

While the above selection criteria may be used to select one or more compounds to be incorporated within a water immiscible fluidic medium, and eliminate compounds which may not provide acceptable performance, an acceptable water immiscible fluidic medium may be a multi-component mixture, and may include some portion of an individual organic or organosilicon compound that would not provide acceptable performance when used as a sole component of a water immiscible fluidic medium. For example, a component may be too highly fluorinated or may unacceptably swell the microfluidic circuit material when used alone, but may be used in combination with other organic or organosilicon compounds to form a water immiscible fluidic medium.

Some suitable organic compounds for use in the water immiscible fluidic medium, either singly or in combination of any kind may include isocetane, 2-(Trifluoromethyl)-3-ethoxydodecafluorohexane (HFE-7500, 3M™, Novec™), heptamethyl nonane (HMN), bis(2-ethylhexyl) carbonate (TEGOSOFT® DEC, (Evonik)), and (Tridecafluoro-1, 1, 2, 2,-tetrahydrooctyl) tetramethydisiloxane (Gelest, Cat #SIB1816.0), or silicone oil (5 centistoke viscosity, Gelest Cat. #DMS-T05).

Aqueous droplet. The aqueous droplet may contain one or more micro-objects, which may include a biological cell or a bead. The aqueous droplet may contain biological products which may include nucleic acid or protein. In some other embodiments, the aqueous droplet may contain reagents for an assay, which may be any kind of reagent such as an enzyme, an antibody, a fluorescently labeled probe, or a chemical reagent.

In some embodiments, the aqueous droplet may also include a surfactant. The surfactant may increase the portability of the aqueous droplet within the water immiscible fluidic medium. In some embodiments, a suitable surfactant may include a non-ionic surfactant. In various embodiments, a surfactant may be, but is not limited to a Pluronic® block alkylene oxide copolymer, including F68 (ThermoFisher Cat. #2400032); a fatty ester ethoxylated sorbitan such as TWEEN® 20 (Signa Aldrich Cat. #P1379) or TWEEN® 60 (Sigma Aldrich P1629); 2, 4, 7, 9, Tetramethyl-5-decyne-4, 7,-diol ethoxylate (TET, Sigma Aldrich Cat #9014-85-1); an ethoxylated nonionic fluorosurfactant such as Capstone® FS-30 (DuPont™, Synquest Laboratories Cat. #2108-3-38).

In some embodiments, sodium dodecyl sulfate (SDS) may be used as a surfactant. In various embodiments, phosphate buffered saline (PBS) may be used as a surfactant. The surfactant may be added to the aqueous droplet in a range of about 1%, 3%, 5%, 10%, 15%, 20%, about 25% v/v or any value in between.

Systems. A system for transporting micro-objects, biological products, and/or reagents that are compatible with and/or soluble in aqueous media is provided by the invention. The system can include, for example, any of the microfluidic devices disclosed herein (e.g., a microfluidic device having an enclosure comprising a base and a microfluidic circuit structure, wherein the base comprises a hydrophobic monolayer covalently bonded to at least a portion of an upper surface of the base). In addition, the systems include a fluidic medium and an aqueous droplet, wherein the fluidic medium and the aqueous droplet are immiscible fluids. The fluidic medium can be any of the immiscible media described herein, and the aqueous droplet can comprise any of the biological materials and/or chemical agents described herein (e.g., proteins, nucleic acids, detergents, surfactants, and the like).

Kits. The invention also provides kits that are suitable for transporting micro-objects, biological products, and/or reagents that are compatible with and/or soluble in aqueous media. The kits can comprise any of the microfluidic devices disclosed herein (e.g., microfluidic devices having an enclosure comprising a base and a microfluidic circuit structure, wherein the base comprises a hydrophobic monolayer covalently bonded to at least a portion of an upper surface of the base). The kits can further comprise a fluidic medium that is immiscible with aqueous media, as well as other useful reagents (e.g., surfactants and the like).

Methods of Manufacturing Microfluidic Devices. A microfluidic device of the invention, such as apparatus 400, can be manufactured by (i) bonding a spacing element 108 to an inner surface 428 of a cover 110 having at least one electrode configured to be connected to an AC voltage source (not shown), (ii) bonding the spacing element 108 (and associated cover 110) to a dielectric surface 414 of a substrate 104 having at least one electrode 418 configured to be connected to an AC voltage source (not shown), whereby the spacing element 108 becomes sandwiched between the inner surface 428 of the cover 110 and the dielectric surface 414 of the substrate 104, with the cover 110 and the substrate 104 oriented substantially parallel to one another, and the substrate 104, spacing element 108, and cover 110 collectively defining an enclosure 435 configured to hold a liquid, and (iii) forming, by vapor deposition, an outer hydrophobic layer 412 on at least a portion of the inner surface 428 of the cover 110 and an out hydrophobic layer 412 on at least a portion of the inner dielectric layer 414 of the substrate 104.

Through vapor deposition of amphiphilic molecules, the hydrophobic layers 422 and 412 can achieve densely packed monolayers in which the amphiphilic molecules are covalently bonded to the molecules of the inner surface 428 of the cover 110 and the inner dielectric surface 414 of the substrate 104, respectively. Any of the self-associating molecules described herein, and equivalents thereof, can be vapor deposited on the inner surfaces of a microfluidic apparatus. To achieve a desirable packing density, self-associating molecules comprising, for example, alkyl-terminated siloxane can be vapor deposited at a temperature of at least 110° C. (e.g., at least 120, 130, 140, 150, 160, etc.), for a period of at least 15 hours (e.g., at least 20, 25, 30, 35, 40, 45, or more hours). Such vapor deposition is typically performed under vacuum and in the presence of a water source, such as magnesium sulfate heptahydrate (i.e., $MgSO_4 \cdot 7H_2O$). Typically, increasing the temperature and duration of the vapor deposition produces improved characteristics of the hydrophobic layers 422 and 412. The vapor deposition process can be optionally improved, for example, by pre-cleaning the cover 110 (with spacing elements 108) and substrate 104. For example, such pre-cleaning can include a solvent bath, such as an acetone bath, an ethanol bath, or a combination thereof. The solvent bath can include sonication. Alternatively, or in addition, such pre-cleaning can include treating the cover 110 (with spacing elements 108) and substrate 104 in an oxygen plasma cleaner. The oxygen plasma cleaner can be operated, for example, under vacuum conditions, at 100 W for 60 seconds.

FIG. 6 illustrates an example a microfluidic apparatus 600 which comprises an enclosure having microfluidic channels 612, 614 and a plurality of chambers 616, and a droplet generator 606 for providing fluidic droplets 620 to the enclosure. Microfluidic channel 614 is configured to hold a first fluidic medium 624. Typically, the first fluidic medium is a hydrophobic fluid, such as an oil (e.g., a silicone oil or a fluorinated oil). Microfluidic channel 614 is connected to the droplet generator 606 via an interface 608, which allows channel 614 to receive droplets 620 generated by the droplet generator 606. The received droplets 620 comprise a liquid which is immiscible in the first fluidic medium 624. Typically, the received droplets will comprise an aqueous medium, which may contain micro-objects, such as cells or beads, or reagents that are soluble in aqueous media. Microfluidic channel 614 is also connected to each of the plurality of chambers 616, facilitating movement of received droplets 620 (as well as droplets 632 pulled from a reservoir of fluid immiscible in the first fluidic medium 624) into and between chambers 616.

Microfluidic channel 612 of apparatus 600 is connected to a subset of chambers 616, and thus is indirectly connected to microfluidic channel 614 via such chambers 616. As illustrated, microfluidic channel 612 and the chambers 616 connected thereto contains a fluidic medium 622 which is immiscible in the first fluidic medium 624. Thus, for example, fluidic medium 622 can be an aqueous medium, such as a cell culture medium. When fluidic medium 622 is a cell culture medium, the chambers 616 that contain culture medium can be used as culture chambers for growing cells, and microfluidic channel 612 can be a perfusion channel that provides a flow of fresh culture medium. As discussed herein, the flow of fresh culture medium in a perfusion channel can, via diffusion of molecules between the perfusion channel and a culture chamber, provide nutrients to the chamber and remove waste from the chamber, thus facilitating continued cell growth.

FIG. 7 illustrates another example a microfluidic apparatus 700 which comprises an enclosure having microfluidic channels 612, 614, a first plurality of chambers 716, and a second plurality of chambers 616, and a droplet generator 606 for providing fluidic droplets 620 to the enclosure. FIG. 7 presents a variation on the microfluidic apparatus 600 shown in FIG. 6, wherein chambers 616 contain a medium 622 that is immiscible in the first fluidic medium 624 (located in microfluidic channel 614) and are located directly across microfluidic channel 614 from corresponding chambers 716. This configuration facilitates movement of fluid droplets 632 (optionally containing micro-objects 630 or biological material) from a select chamber 616 to the corresponding chamber 716, where the fluid droplets (and any micro-objects 630 or biological material) can be processed.

Another example a microfluidic apparatus comprises an enclosure having microfluidic channels 612, 614, a first plurality of chambers 716, and a second plurality of chambers 616, and a droplet generator 606 for providing fluidic droplets 620 to the enclosure. This embodiment presents a variation on the microfluidic apparatus 700 shown in FIG. 7, wherein chambers 616 are tapered at one end to facilitate the movement of micro-particles to the interface of the first fluidic medium 624 and the second fluidic medium 622 when the microfluidic apparatus is tilted such that the tapered ends of chambers 616 have a lower potential energy (in the applicable gravitational field) relative to the ends that are not tapered.

The microfluidic circuits formed by the microfluidic channels 612,614 and chambers 616, 716 are merely examples, and many other configurations of channels and chambers are encompassed by the invention. For example, in each of apparatuses 600 and 700, microfluidic channel 612 and the chambers 616 directly connected to channel 612 are optional features. Thus, apparatuses 600 and 700 can lack perfusion channels and culture chambers.

In embodiments where microfluidic channel 612 is present, the substrate which helps to define channel 612 and/or directly connected chambers 616 (e.g., by forming the base of the channel and/or chambers) can have an electrowetting configuration. Alternatively, however, the substrate which helps to define the channel 612 and/or directly connected chambers 616 can lack an electrowetting configuration (e.g., and instead can have a DEP configuration, or neither an electrowetting nor a DEP configuration). In embodiments in which microfluidic channel 612 is present, and the substrate which helps to define channel 612 and/or directly connected chambers 616 has an electrowetting configuration, the outer hydrophobic surface of the substrate can be patterned to be more hydrophilic than the outer hydrophobic surface of the substrate which helps to define channel 614. The increased hydrophilicity can be achieved, for example, as discussed above.

The droplet generator 606 and any microfluidic circuit to which it provides droplets can be part of a microfluidic device (either an integral part or connected thereto), which can be like any of the microfluidic devices illustrated in the drawings or described herein. Although one droplet generator 606 is shown in FIGS. 6 and 7, more than one such droplet generator 606 can provide droplets to the microfluidic circuit of apparatuses 600 and 700. The droplet generator 606 itself can include an electrowetting configuration, and can thus comprise a substrate having a photoresponsive layer, which can comprise a-Si:H (e.g., as illustrated in U.S. Pat. No. 6,958,132), a photo-actuated circuit substrate (e.g., as illustrated in U.S. Patent Application Publication No. 2014/0124370), a phototransistor-based substrate (e.g., as illustrated in U.S. Pat. No. 7,956,339), or an electrically-actuated circuit substrate (e.g., as illustrated in U.S. Pat. No. 8,685,344). Alternatively, the droplet generator can have a T- or Y-shaped hydrodynamic structure (e.g., as illustrated in U.S. Pat. Nos. 7,708,949, 7,041,481 (reissued as RE41,780), 2008/0014589, 2008/0003142, 2010/0137163, and 2010/0172803). All of the foregoing U.S. patent documents are incorporated by reference herein in their entirety.

As shown, the droplet generator 606 can comprise one or more fluidic inputs 602 and 604 (two are shown but there can be fewer or more) and a fluidic output 208, which can be connected to the microfluidic channel 614. Liquid media 622, 624, biological micro-objects 630, reagents, and/or other biological media can be loaded through the inputs 602 and 604 into the droplet generator 606. The droplet generator 606 can generate and output into the channel 614 droplets 620 of the liquid medium 622 (which can, but need not, contain one or more biological micro-objects 630), reagents, or other biological medium. If the channel 614 has an electrowetting configuration, the droplets 620 can be moved in the channel 614 utilizing electrowetting (or optoelectrowetting). Alternatively, the droplets 620 can be moved in the channel 614 by other means. For example, the droplets 620 can be moved in the channel 614 using fluidic flow, gravity, or the like.

As discussed above, the microfluidic channel 614 and select chambers 616/716 can be filled with a first fluidic medium 624, and microfluidic channel 612 and chambers 616 connected directly thereto can be filled with a second fluidic medium 622. The second fluidic medium 622 (hereinafter an "aqueous medium") can be an aqueous medium, such as a sample medium for maintaining, culturing, or the like biological micro-objects 630. The first fluidic medium 624 (hereinafter an "immiscible medium") can be a medium in which the aqueous medium 622 is immiscible. Examples of the aqueous medium 622 and the immiscible medium 624 include any of the examples discussed above for various media.

The droplet generator 606 can be utilized to load biological micro-objects and/or facilitate the running of biochemical and/or molecular biological workflows on the microfluidic apparatus. FIGS. 6 and 7 illustrate non-limiting examples. By using a droplet generator, the apparatus can have an electrowetting configuration throughout the fluidic circuit.

FIGS. 6 and 7 illustrate an example in which the droplet generator 606 generates a droplet 620 comprising a reagent (or other biological material). The reagent-containing droplet 620 can be moved through the microfluidic channel 614 and into one of the chambers 616/716 containing the immiscible medium 624. Prior to or after moving the reagent-containing droplet 620 into one of the chambers 616/716, one or more micro-objects 630 in one or more droplets 632 can be moved into the same chambers 616/716. The reagent-containing droplet 620 can then be merged with the droplet 632 containing the micro-object 630, allowing the reagents of droplet 620 to mix and chemically react with the contents of droplet 632. The one or more micro-object-containing droplets 632 can be supplied by the droplet generator 606 (not shown) or can be obtained from a holding pen 616, as shown in FIGS. 6 AND 7. The micro-object 630 can be a biological micro-object, such as a cell, which has optionally been cultured (e.g., in a chamber 616) prior to being moved to the processing chamber 616/716. Alternatively, the micro-object 630 can be a bead, such as an affinity bead that is capable of binding to molecules of interest in a sample (e.g., cell secretions present in sample material 622 after the sample material 622 has been used to culture one or more biological cells). In still other alternatives, the one or more droplets 632 can contain no micro-objects but only aqueous medium, such as sample material 622, e.g., that contains cell secretions after the sample material 622 has been used to culture one or more biological cells.

Figure 8:
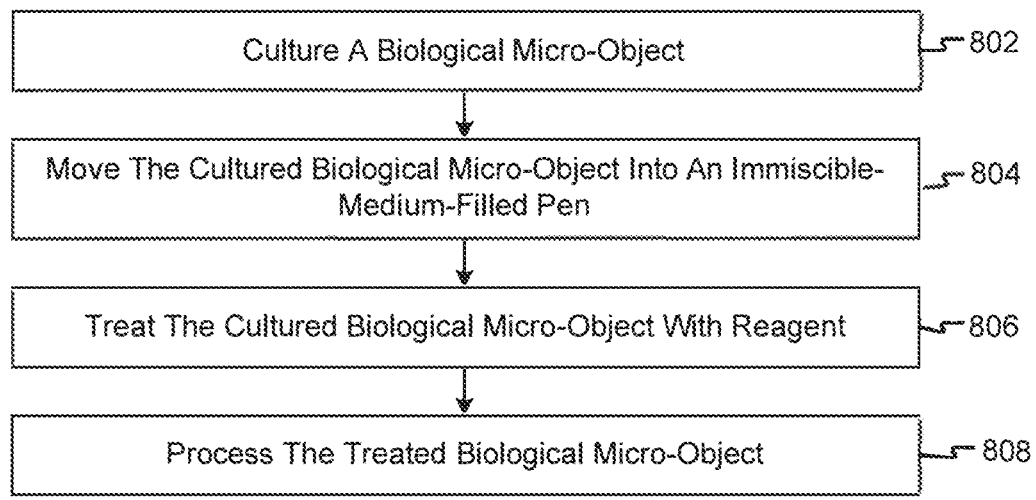
FIG. 8 is a diagram of a method of processing biological micro-objects within a microfluidic apparatus.

FIG. 8 illustrates an example of a process 800 that can be performed in a microfluidic device comprising a microfluidic circuit like any of apparatuses 600 and 700.

At step 802 of the process 800, a biological micro-object can be cultured in a holding pen filled with a sample medium (e.g., cell culture medium). For example, a micro-object 630 of FIG. 6 or 7 can be biological and can be cultured in its chamber 616. Culturing can be generally as discussed above. For example, culturing can include perfusing the channel 612 with a culture medium 622. Step 802 can be performed over a specified period of time.

At step 804, the cultured biological micro-object can be moved from the sample-medium-filled chamber 616 in which it was cultured to a chamber 616/716 filled with a medium in which the sample medium is immiscible. For example, the cultured micro-object 630 can be moved in a droplet 620 or 632 of sample medium 622 from one of the holding pens 616 into one of the holding pens 616/716, as illustrated in FIGS. 6 and 7, as discussed above.

At step 806, the cultured biological micro-object can be subjected to one or more treatments or processes in the immiscible-medium-filled holding pen. For example, one or more droplets 620 containing one or more reagents can be produced by the droplet generator 606 and moved into an immiscible-medium-filled chamber 612/716 and merged with the droplet 632 containing the cultured biological micro-object 630, as shown in FIGS. 6 and 7 and discussed above. For example, a first reagent-containing droplet 620 can contain a lysing reagent. Merger of the droplet 632 containing the cultured biological micro-object 630 with the first reagent-containing droplet 620 containing lysing reagent, would result in the lysis of the cultured biological micro-object 630. In other words, a combined droplet (not shown) would be formed that contains a cell lysate from the cultured biological micro-object 630. Additional (e.g., second, third, fourth, etc.) reagent-containing droplets 620 could then be merged with the cell lysate-containing new droplet, so as to further process the cell lysate as desired.

In addition or as another example, one or more droplets containing one or more labeled capture micro-objects (not shown) having an affinity for a secretion or other material or materials of interest (e.g., nucleic acids such as DNA or RNA, proteins, metabolites, or other biological molecules) produced the cultured biological micro-object 630 can be generated by the droplet generator 606 and moved into the immiscible-medium-filled pen 616 or 716 and merged with the droplet of sample medium 622 containing the cultured biological micro-object 630 in a similar manner In cases where the cultured biological micro-object 630 has already been lysed, capture micro-object-containing droplet 620 could contain one or more affinity beads (e.g., having affinity for nucleic acids, such as DNA, RNA, microRNAs, or the like) which, upon merger with the cell lysate-containing droplet in holding pen 616 or 716, could bind to target molecules present in the lysate.

At step 808, the treated biological micro-object can be optionally processed. For example, if at step 806, a capture object (not shown) is moved into the immiscible-medium-filled chamber 616/716 with the cultured biological micro-object 630, the chamber 616/716 can be monitored at step 808 for a reaction (e.g., a fluorescent signal) indicative of a quantity of the material of interest bound to the labeled capture micro-object. Alternatively, such a capture micro-object (not shown) can be removed (e.g., in a droplet 622) from the chamber 616/716 and exported from the microfluidic device (not shown in FIGS. 6 and 7) for subsequent analysis. As yet another example, the treated biological micro-object 630 can be removed (e.g., in a droplet 632) from the chamber 616/716 and exported from the microfluidic device (not shown) for subsequent analysis.

Figure 9:
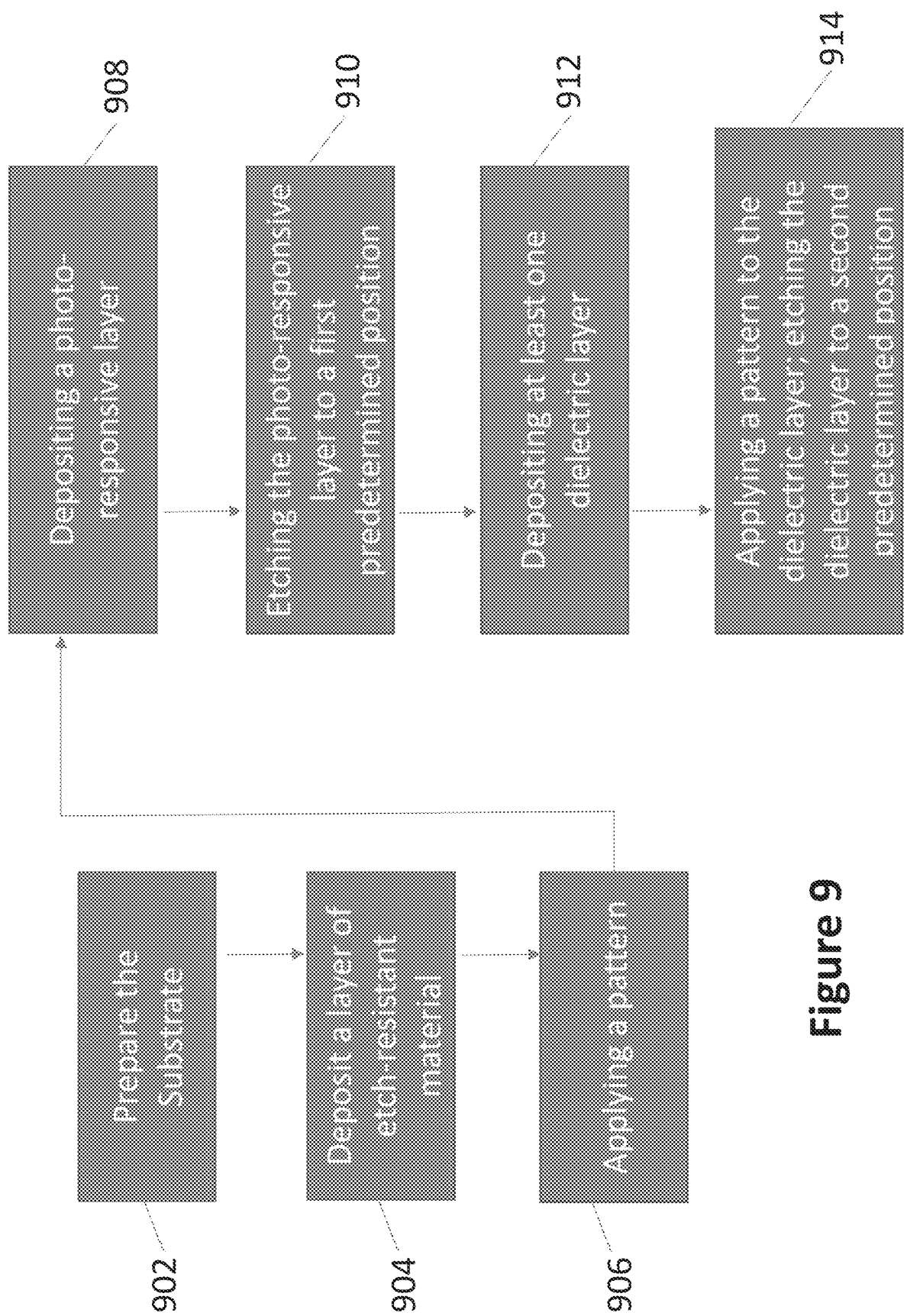
FIG. 9 is a method that can be applied to manufacture a substrate for a microfluidic device having a first section with an electrowetting configuration and a second section with a dielectrophoresis configuration.
Figure 10:
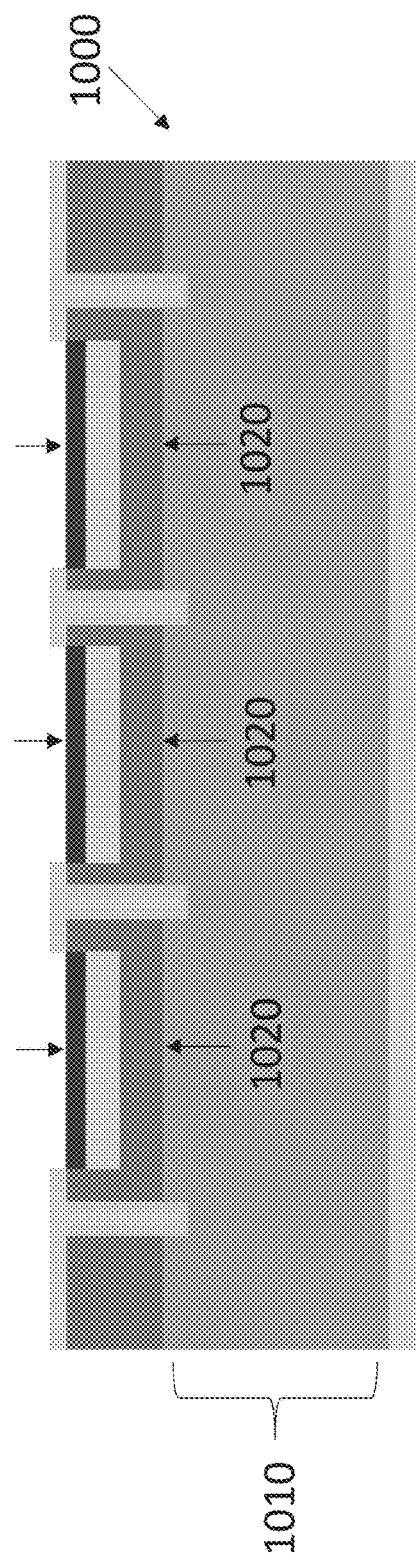
Figure 11:
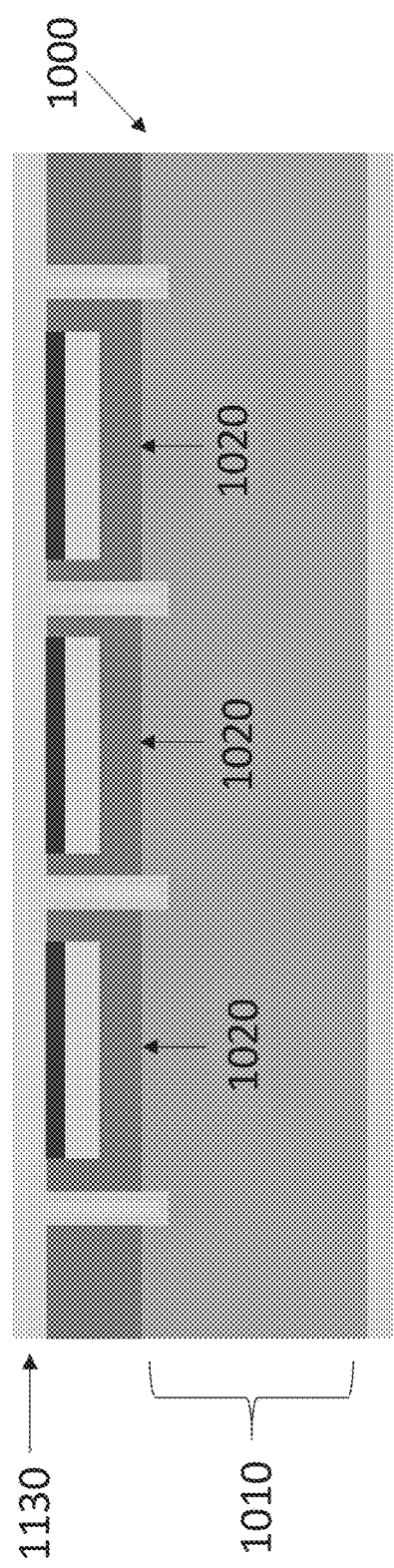

FIG. 9 outlines a method for forming a substrate for a microfluidic device that includes both an electrowetting configuration and a dielectrophoresis (DEP) configuration. For example, the method depicted in FIG. 9 can be utilized to form a monolithic substrate of the type shown in the microfluidic device of FIG. 5. FIGS. 10-18 depict cross-sectional views of intermediate structures formed after various steps in the method of FIG. 9 have been performed. A substrate having a DEP configuration that includes an array of phototransistors is the starting point in FIGS. 10-18. Of course, as persons skilled in the art will understand, the starting substrate is not limited to a DEP configured substrate having an array of phototransistors, but rather can be applied to other types of substrates, such as a substrate comprising a layer of amorphous silicon or an array of electrodes that are electrically actuated. Moreover, steps in the method of FIG. 9 can be used individually and/or in other combinations to produce other types of microfluidic devices having a conductive substrate, including other microfluidic devices that have been described herein.

Step 902 in the method of FIG. 9 includes preparing an initial substrate for further processing. As shown in vertical cross-section in FIG. 10, the initial substrate 1000 includes a highly doped layer of conductive silicon 1010, upon which an array of phototransistors 1020 has been formed. The step of preparing the substrate 1000 can include a thermal anneal process. The process of step 902 can prepare the surface of substrate 1000 to ensure proper bonding of materials subsequently deposited on the substrate 1000.

Step 904 in the method of FIG. 9 includes the deposition of a selectively etch-resistant material on a top surface of the initial substrate. As shown in vertical cross-section in FIG. 11, a layer of conditionally etch-resistant material 1130 is deposited on a top surface of the substrate 1000 such that it covers the surfaces of the phototransistors 1020 in the array. In some embodiments, the conditionally etch-resistant material 1130 can be a nitride.

Step 906 in the method of FIG. 9 includes applying a first pattern upon the conditionally etch-resistant material that was deposited on the substrate during step 904. As shown in FIG. 12, the pattern allows conditionally etch-resistant material 1130 to be removed from the substrate 1000 in select regions (e.g., the surface of the phototransistor array on the left side of substrate 1000). Applying the pattern to the conditionally etch-resistant material 1130 that was deposited on the substrate 1000 during step 904 can be achieved by a lithography process, as is well known in the semiconductor processing industry. Such lithography processes include, for example, E-beam, X-Ray, UV, and Deep UV. Typically, a polymer is used to define the pattern.

As set forth in step 908 of the method of FIG. 9, the pattern (e.g., polymer) deposited in step 906 is subsequently processed by depositing a photo-responsive layer upon the pattern and then selectively exposing portions of the photo-responsive layer to light (e.g., light having a suitable wavelength and intensity for the material of the photo-responsive layer).

Step 910 in the method of FIG. 9 includes etching the photo-responsive layer (and any conditionally etch-resistant material located beneath the etchable portions of the photo-responsive layer) down to a first predetermined position. As shown in FIG. 12, the first predetermined position can be, for example, the surface of the substrate (e.g., the surface of the phototransistors 1020).

Figure 14:
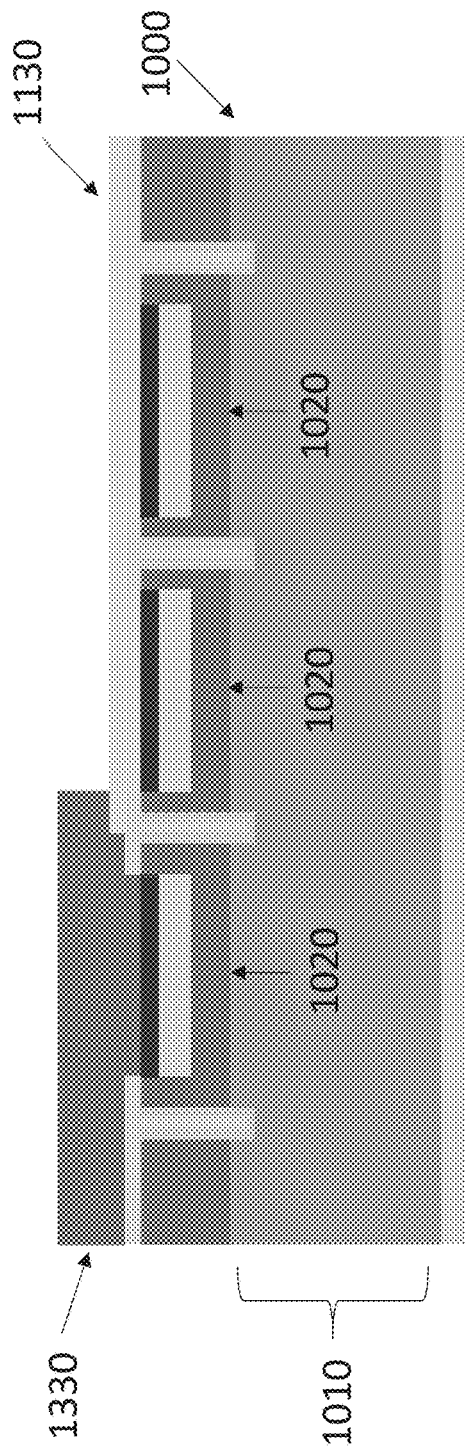

An optional subsequent set of steps (not shown) in the method of FIG. 9 is the deposition, patterning and etching of a layer of conductive material once the substrate has been patterned with respect to the conditionally etch-resistant layer. As shown in FIG. 13, the conductive material 1330 can be deposited upon both the substrate surface (e.g., the surface of the phototransistors 1020 on the left side of the substrate 1000) and the portion of the conditionally etch-resistant layer 1130 that was not removed during steps 908 and 910. The conductive material 1330 can be, for example, conductive silicon, such as amorphous silicon or highly-doped silicon. As shown in FIG. 14, the patterning and etching of the conductive material 1330 can then result in a first portion of the substrate 1000 having a layer of conductive material 1330 directly deposited thereon (e.g., on the surfaces of the phototransistors 1020 on the left side of the substrate 1000), and a second portion of the substrate 1000 having a layer 1130 of conditionally etch-resistant material directly deposited thereon (e.g., on the surfaces of the phototransistors 1020 on the right side of the substrate 1000).

Figure 15:
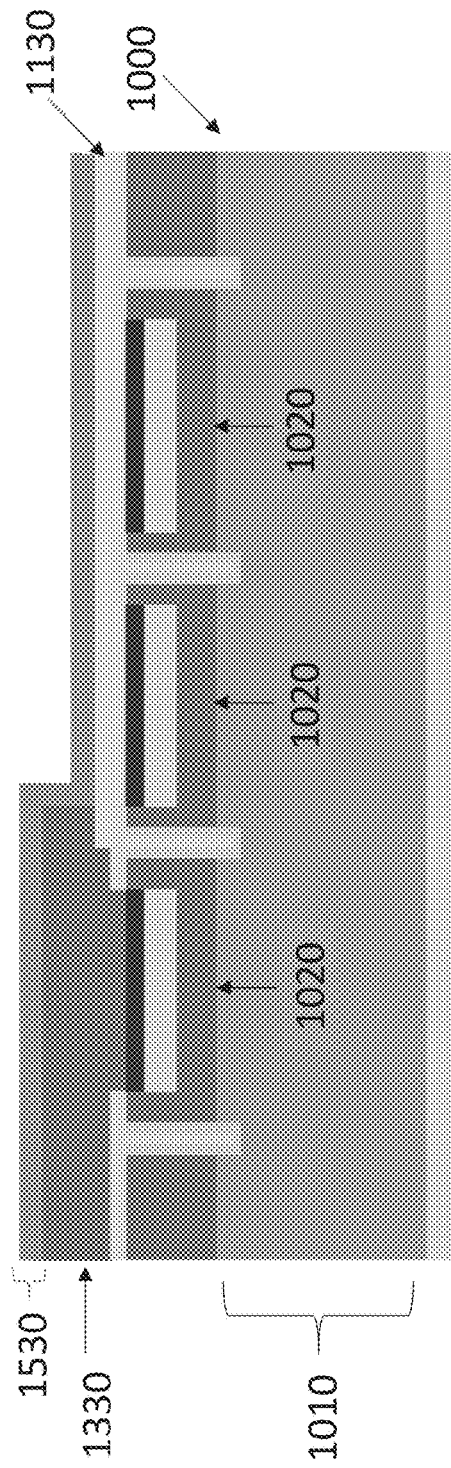

Step 912 in the method of FIG. 9 includes depositing at least one dielectric layer upon the substrate (or any materials already deposited on the substrate and not etched away). As discussed elsewhere herein (e.g., in connection with the device of FIG. 1B), individual layers of a stack of dielectric layers (e.g., a first layer of dielectric material, a second layer of dielectric material, a third layer of dielectric material, etc.) can be sequentially deposited on the substrate. For example, as shown in FIG. 15, a dielectric stack 1530 consisting of two layers of dielectric material can be deposited upon the substrate 1000. For consistency with other sections herein, the first layer of the dielectric stack 1530 need not be the first layer deposited on the substrate 1000. Rather, the terms first and second can be used arbitrarily or with respect to the order of the layers of dielectric material starting from the surface and moving inward into the substrate. Thus, in the context of FIG. 15, the first layer of dielectric material deposited on the substrate 1000 can be a "second layer" of dielectric material, and the second layer of dielectric material deposited on the substrate 1000 can be a "first layer" of dielectric material.

Figure 16:
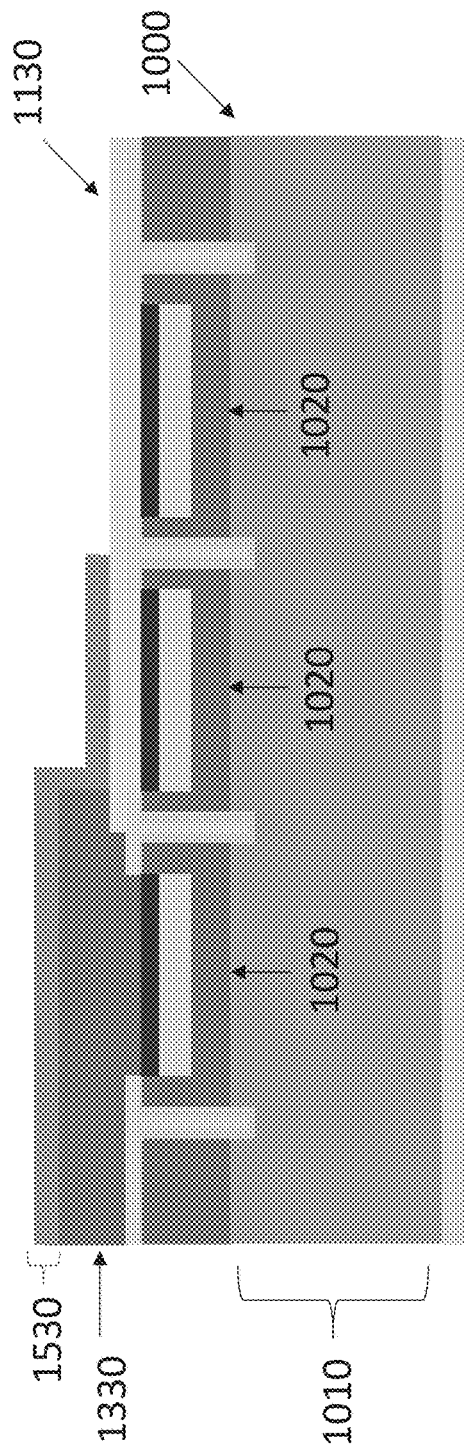

Step 914 in the method of FIG. 9 includes applying a second pattern on top of at least one dielectric layer and etching the at least one dielectric layer to a second predetermined location. In some embodiments, the second predetermined location can be a surface of the layer of conditionally etch-resistant material 1130. Thus, as shown in FIG. 16, the layers of the dielectric stack 1530 can be etched away from a selected portion of the substrate 1000 down to the surface of the conditionally etch resistant material 1130. As discussed above, the conditionally etch-resistant material 1130 can be a nitride. Accordingly, the etching material used in step 914 can be suitable for etching away dielectric materials but not nitride.

Figure 17:
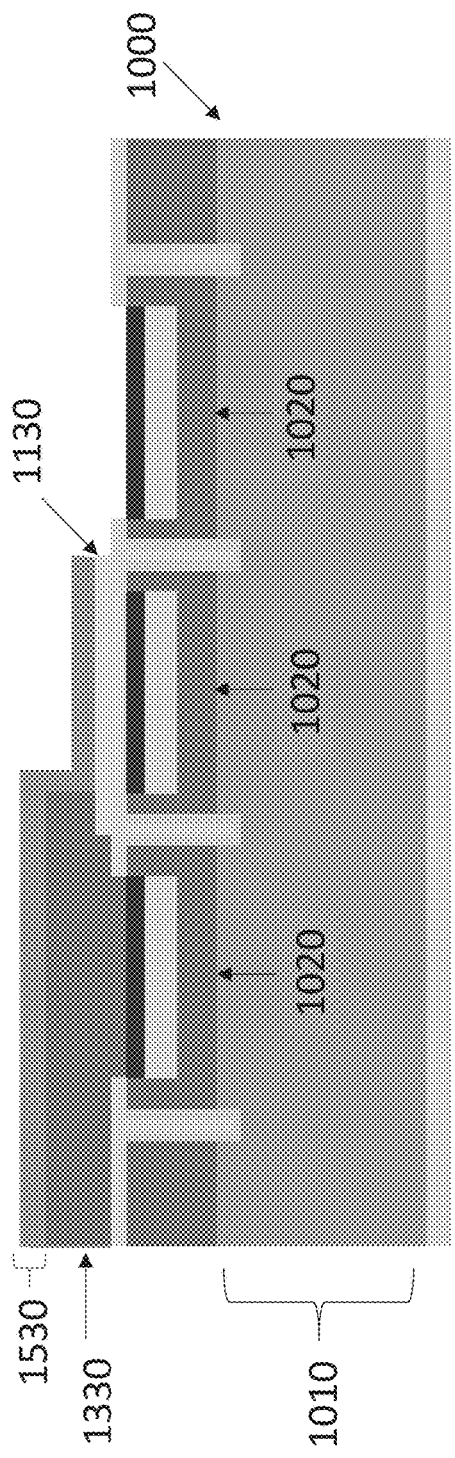
Figure 18:
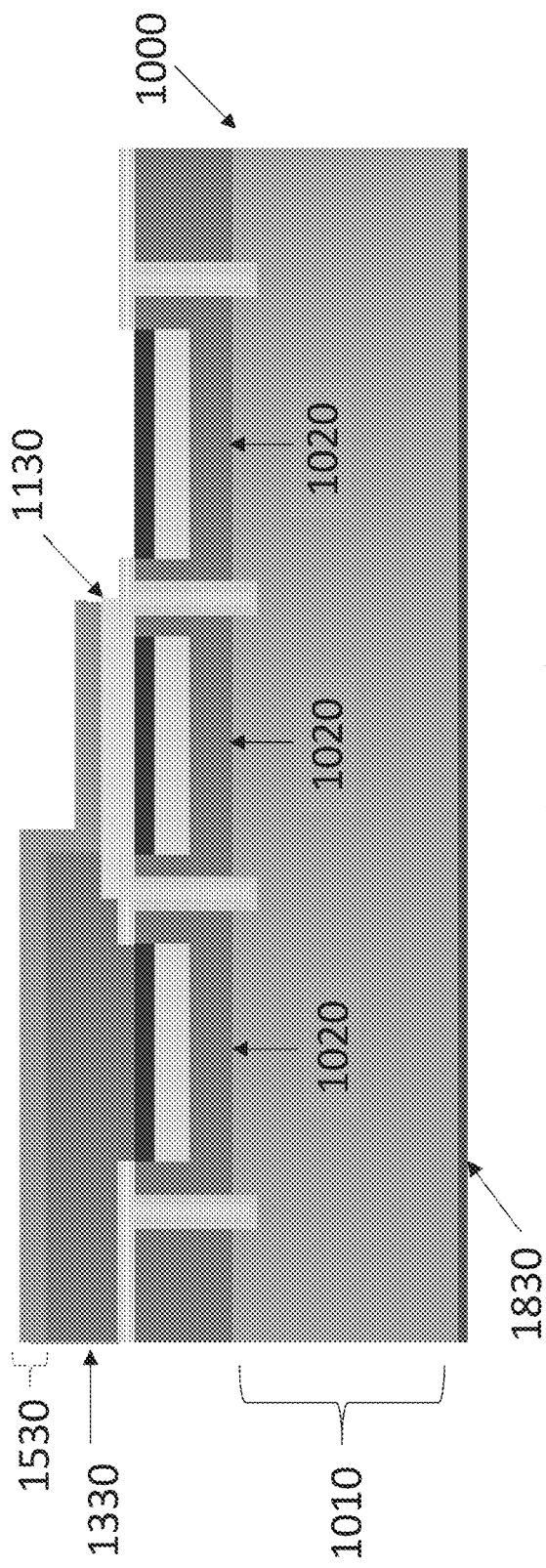

In various embodiments, optional steps may be further performed. For example, a third pattern can be deposited, and a stripping of the conditionally etch-resistant layer can be performed (which optionally can result in up to a 10 um etch into the silicon substrate). As shown in FIG. 17, the conditionally etch-resistant layer 1130 has been etched away from the right side of the substrate 1000, resulting in the surface of the phototransistors 1020 on the right side becoming exposed once again. In addition, steps can be taken to perform an oxide strip of the bottom of the substrate 1000 and a backside metallization to add a layer of conductive metal 1830 (e.g., silver or gold) to the substrate, as shown in FIG. 18. The resulting substrate shown in FIG. 18 can have a first section (e.g., on the right side) that is configured to produce DEP forces, and a second section (e.g., on the left side) that is configured to produce electrowetting forces. At the junction between the first and second sections, the substrate can be electrically inactive, at least with respect to generating DEP and electrowetting forces. The thickness of the inactive region will depend upon the precision of the masking and etching steps, and can be, for example, less than 2 mm in thickness (e.g., less than 1.5 mm, less than 1.0 mm, less than 0.5 mm, or less).

Although specific embodiments and applications of the invention have been described in this specification, these embodiments and applications are exemplary only, and many variations are possible. For example, the methods of FIG. 8 can be performed with respect to sample material contain cell secretions (e.g., after the sample material 682 has been used to culture one or more biological cells). In such an embodiment, step 802 would remain the same, but step 804 would involve moving droplets 632 which can contain no micro-objects but only aqueous medium, such as sample material 622 containing cell secretions, into immiscible-medium-containing chambers 616/716, and steps 806 and 808 would be performed with respect to such aqueous medium-containing droplets 632. Furthermore, the electrowetting configurations discussed herein can be any type of electronic wetting configuration known in the art, examples of which are disclosed in U.S. Pat. No. 6,958,132 (for OEW configurations) and US Patent Application Publication No. US2016/0158748 (for single-sided OEW configurations). Other examples of electrowetting configurations include electrowetting on dielectric (EWOD) devices, which can be electronically controlled, an example of which is disclosed in U.S. Pat. No. 8,685,344. Similarly, the dielectrophoresis configurations discussed herein can be any type of dielectrophoresis configuration known in the art, examples of which are disclosed in U.S. Pat. No. RE 44,711 (Wu et al.), U.S. Pat. No. 7,956,339 (Ohta et al.), U.S. Pat. No. 6,294,063 (Becker et al.), U.S. Pat. No. 6,942,776 (Medoro), and U.S. Pat. No. 9,403,172 (Wu et al.). All of the foregoing US patent documents are incorporated herein in their entirety by reference.

EXAMPLES

System and Microfluidic device: The microfluidic device and instrument for operating it were manufactured by Berkeley Lights, Inc. The system included at least a flow controller, temperature controller, fluidic medium conditioning and pump component, light source for light activated DEP or EW configurations, mounting stage, and a camera. The microfluidic device included an EW configuration with a surface as described below.

Figures 20A, 20B, 20C:
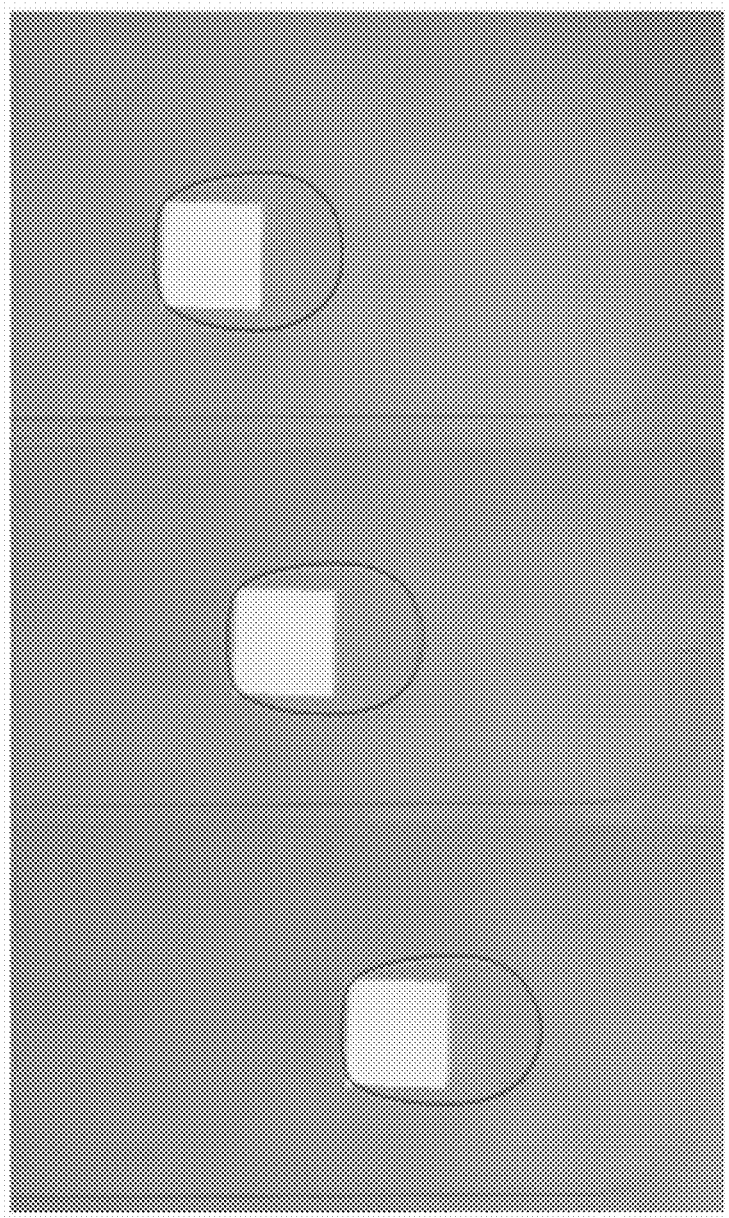
FIGS. 20A-20C are photographic representations of the movement of an aqueous droplet on a modified microfluidic surface according to an embodiment of the invention.

Example 1. Preparation of an Electrowetting Microfluidic Device Having Modified interior surfaces. A microfluidic device (Berkeley Lights, Inc.) having a base that included an electrode activation substrate having a semiconductive layer of photosensitive silicon and a dielectric layer having an upper surface of alumina, a cover having a glass support with an ITO electrode, and microfluidic circuit material of photopatterned silicone separating the base and the cover, was treated in an oxygen plasma cleaner (Nordson Asymtek) for 1 min, using 100 W power, 240 mTorr pressure and 440 sccm oxygen flow rate. The plasma treated microfluidic device was treated in a vacuum reactor with trimethoxy (3, 3, 4, 4, 5, 5, 6, 6, 7, 7, 8, 8, 9, 9, 10, 10, 11, 11, 12, 12, 13, 13, 14, 14, 15, 15, 16, 16, 16-nonaicosafluorohexadecyl)silane (0.3 g, details of synthesis as described in U.S. Provisional Application 62/410,238, filed Oct. 19, 2016) in a foil boat in the bottom of the vacuum reactor in the presence of magnesium sulfate heptahydrate (0.5 g, Acros), as a water reactant source, in a separate foil boat in the bottom of the vacuum reactor. The chamber was then pumped to 750 mTorr using a vacuum pump and sealed. The vacuum reactor was placed within an oven heated to 180° C. for 24-48 h. After cooling to room temperature and introducing argon to the evacuated chamber, the microfluidic device having an outer hydrophobic layer of dimethoxy (3, 3, 4, 4, 5, 5, 6, 6, 7, 7, 8, 8, 9, 9, 10, 10, 11, 11, 12, 12, 13, 13, 14, 14, 15, 15, 16, 16, 16-nonacosafluoro-hexadecyl)siloxy moieties on all interior surfaces was removed from the reactor. Following removal, the microfluidic device was primed with silicone oil (5 centistoke viscosity, Gelest Cat. #DMS-T05) prior to use. FIGS. 20A-20C are successive photographic images of a droplet of water being moved around upon the hydrophobic layer (i.e., the droplet actuation surface), within an immiscible silicone oil phase. The droplet demonstrated excellent ability to be moved using the optically actuated electrowetting configuration and droplet actuation surface of the microfluidic device.

RECITATION OF EMBODIMENTS

1. A microfluidic device having an electrowetting configuration, the microfluidic device comprising:
 a substrate having a dielectric layer, a droplet actuation surface, and a first electrode configured to be connected to an AC voltage source; and
 a second electrode configured to be connected to the AC voltage source;
 wherein the dielectric layer is electrically coupled to the first electrode, and
 wherein the droplet actuation surface comprises a hydrophobic layer covalently bonded to the dielectric layer.
2. The microfluidic device of embodiment 1, wherein the device has a single-sided electrowetting configuration.
3. The microfluidic device of embodiment 2, wherein the second electrode is a mesh electrode comprised by the substrate.
4. The microfluidic device of embodiment 1, wherein the device has an opto-electrowetting (OEW) configuration.
5. The microfluidic device of embodiment 1, wherein the device has an electrowetting on dielectric (EWOD) configuration.
6. The microfluidic device of any one of embodiments 1 to 5, wherein the hydrophobic layer is a monolayer comprising a surface modifying ligand and a linking group that links the surface modifying ligand to the surface, wherein the droplet actuation surface has a structure of Formula II:

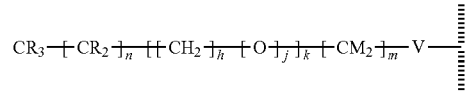

Formula II wherein ⦀ is a surface of the dielectric layer; V is —P(O)(OY)W— or —Si(OZ)$_2$W—; W is —O—, —S—, or —NH— and connects to the surface; Z is a bond to an adjacent silicon atom attached to the surface or is a bond to the surface; Y is a bond to an adjacent phosphorus atom attached to the surface or is a bond to the surface; R is hydrogen or fluorine; M is hydrogen or fluorine; h is independently an integer of 2 or 3; j is 1; k is 0 or 1; m is 0 or an integer of 1 to 20; n is 0 or an integer of 1 to 20; the sum of (n+[(h+j)·k]+m) is an integer of 11 to 25; when k is 1, then m is at least 2 and M is hydrogen; and when k is 0 and R is fluorine, then m is at least 2 and M is hydrogen.

7. The microfluidic device of any one of embodiments 1 to 6, wherein the electrowetting configuration of the device is comprised by a first section of the device, and wherein the device further comprises a second section having a dielectrophoresis (DEP) configuration.

8. A microfluidic device comprising: a substrate having at least one electrode configured to be connected to a voltage source; a cover having at least one electrode configured to be connected to the voltage source; and at least one spacing element,
wherein the substrate and the cover are substantially parallel to one another and joined together by the spacing element so as to define an enclosure configured to hold a liquid, wherein the substrate has a droplet actuation surface that defines, in part, the enclosure, the droplet actuation surface having an inner dielectric layer and an outer hydrophobic layer,
wherein the outer hydrophobic layer comprises self-associating molecules covalently bonded to a surface of the inner dielectric layer, to thereby form a densely packed hydrophobic monolayer thereon, and
wherein, when the at least one electrode of the substrate and the at least one electrode of the cover are connected to opposing terminals of the voltage source, the substrate is capable of applying an electrowetting force to aqueous droplets in contact with the droplet actuating surface of the substrate.

9. The microfluidic apparatus of embodiment 8, wherein the self-associating molecules of the hydrophobic monolayer each comprise a surface modifying ligand and a linking group that links the surface modifying ligand to the surface of the inner dielectric layer, wherein the droplet actuation surface has a structure of Formula II:

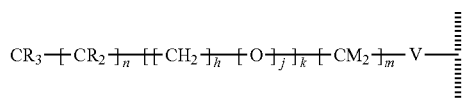

Formula II wherein ▌ is a surface of the dielectric layer; V is —P(O)(OY)W— or —Si(OZ)$_2$W—; W is —O—, —S—, or —NH— and connects to the surface; Z is a bond to an adjacent silicon atom attached to the surface or is a bond to the surface; Y is a bond to an adjacent phosphorus atom attached to the surface or is a bond to the surface; R is hydrogen or fluorine; M is hydrogen or fluorine; h is independently an integer of 2 or 3; j is 1; k is 0 or 1; m is 0 or an integer of 1 to 20; n is 0 or an integer of 1 to 20; the sum of (n+[(h+j)·k]+m) is an integer of 11 to 25; when k is 1, then m is at least 2 and M is hydrogen; and when k is 0 and R is fluorine, then m is at least 2 and M is hydrogen.

10. The microfluidic device of embodiment 9, wherein V is —Si(OZ)$_2$W—.

11. The microfluidic device of embodiment 9, wherein V is —P(O)(OY)W—.

12. The microfluidic device of any one of embodiments 9 to 11, wherein n is an integer of 1 to 20, and wherein R is hydrogen.

13. The microfluidic device of embodiment 12, wherein m is an integer of 1 to 20, and
wherein M is hydrogen.

14. The microfluidic device of embodiment 13, wherein m is 2.

15. The microfluidic device of any one of embodiments 9 to 11, wherein n is an integer of 1 to 20, and wherein R is fluorine.

16. The microfluidic device of embodiment 15, wherein m is an integer of 1 to 20, and
wherein M is hydrogen.

17. The microfluidic device of embodiment 16, wherein m is 2.

18. The microfluidic device of any one of embodiments 9 to 17, wherein k is 1.

19. The microfluidic device of any one of embodiments 9 to 17, wherein k is 0.

20. The microfluidic device of any one of embodiments 9 to 19, wherein the sum of (n+[(h+j)·k]+m) is an integer of 13 to 19.

21. The microfluidic device of any one of embodiments 8 to 20, wherein the outer hydrophobic layer of the droplet actuation surface of the substrate has a thickness of less than 5 nanometers.

22. The microfluidic device of any one of embodiments 8 to 21, wherein the outer hydrophobic layer of the droplet actuation surface of the substrate is patterned such that select regions are relatively hydrophilic compared to the remainder of the outer hydrophobic layer.

23. The microfluidic device of any one of embodiments 8 to 22, wherein the inner dielectric layer of the droplet actuation surface of the substrate comprises a first layer of dielectric material comprising an oxide.

24. The microfluidic device of any one of embodiments 8 to 23, wherein the oxide is a metal oxide.

25. The microfluidic device of embodiment 24, wherein the metal oxide is aluminum oxide.

26. The microfluidic device of any one of embodiments 23 to 25, wherein the first layer of dielectric material is formed by atomic layer deposition.

27. The microfluidic device of any one of embodiments 23 to 26, wherein the inner dielectric layer of the droplet actuation surface of the substrate further comprises a second layer of dielectric material, and wherein the outer hydrophobic layer is covalently bonded to the first layer of dielectric material.

28. The microfluidic device of embodiment 27, wherein the second layer of dielectric material comprises an oxide or a nitride.

29. The microfluidic device of embodiment 28, wherein the second layer of dielectric material is selected from the group consisting of silicon dioxide and silicon nitride.

30. The microfluidic device of any one of embodiments 27 to 29, wherein the second layer of dielectric material is formed by plasma enhanced chemical vapor deposition.

31. The microfluidic device of any one of embodiments 23 to 30, wherein the first layer of dielectric material comprises first and second sublayers of dielectric materials, wherein the first sublayer is covalently bonded to the hydrophobic layer.

32. The microfluidic device of embodiment 31, wherein the first sublayer of dielectric material comprises silicon oxide.

33. The microfluidic device of embodiment 31, wherein the first sublayer of dielectric material is deposited by ALD.

34. The microfluidic device of any one of embodiments 31 to 33, wherein the first layer of dielectric material has a thickness of about 10 nm to about 20 nm.

35. The microfluidic device of embodiment 34, wherein the first sublayer of dielectric material has a thickness of about 2 nm to about 10 nm.

36. The microfluidic device of any one of embodiments 8 to 35, wherein the inner dielectric layer of the droplet actuation surface of the substrate has a thickness of at least about 40 nanometers.

37. The microfluidic device of embodiment 36, wherein the inner dielectric layer of the droplet actuation surface of the substrate has a thickness of about 40 nanometers to about 120 nanometers.

38. The microfluidic device of any one of embodiments 8 to 37, wherein the substrate further comprises a photoresponsive layer having a first side that contacts the inner dielectric layer and a second side that contacts the at least one electrode.

39. The microfluidic device of embodiment 38, wherein the photoresponsive layer comprises hydrogenated amorphous silicon (a-Si:H).

40. The microfluidic device of embodiment 38 or 39, wherein the photoresponsive layer has a thickness of at least 900 nanometers.

41. The microfluidic device of embodiment 40, wherein the photoresponsive layer has a thickness of about 900 to 1100 nanometers.

42. The microfluidic device of embodiment 38, wherein the photoresponsive layer comprises a plurality of conductors, each conductor controllably connectable to the at least one electrode of the substrate via a phototransistor switch.

43. The microfluidic device of any one of embodiments 8 to 42, wherein the substrate comprises a single electrode configured to be connected to an AC voltage source, the single electrode comprising a layer of indium-tin-oxide (ITO).

44. The microfluidic device of any one of embodiments 8 to 42, wherein the substrate comprises a single electrode configured to be connected to an AC voltage source, the single electrode comprising a layer of electrically conductive silicon.

45. The microfluidic device of any one of embodiments 8 to 37, wherein the substrate comprises a plurality of electrodes, each electrode configured to be connected to one or more AC voltage source(s).

46. The microfluidic device of embodiment 45, wherein each electrode of the plurality is connectable to one of the one or more AC voltage source(s) via a transistor switch.

47. The microfluidic device of any one of embodiments 8 to 46, wherein the cover has an inward-facing surface that defines, in part, the enclosure, the inward-facing surface of the cover having an inner layer and an outer hydrophobic layer, wherein the outer hydrophobic layer of the cover comprises self-associating molecules covalently bonded to a surface of the inner layer of the cover, to thereby form a densely packed hydrophobic monolayer thereon.

48. The microfluidic device of embodiment 47, wherein the self-associating molecules of the hydrophobic monolayer of the cover each comprise a surface modifying ligand and a linking group that links the surface modifying ligand to the surface of the inner layer of the cover, wherein the inward-facing surface of the cover has a structure of Formula II:

Formula II

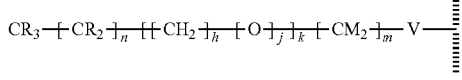

wherein ▌ is a surface of the dielectric layer; V is —P(O)(OY)W— or —Si(OZ)$_2$W—; W is —O—, —S—, or —NH— and connects to the surface; Z is a bond to an adjacent silicon atom attached to the surface or is a bond to the surface; Y is a bond to an adjacent phosphorus atom attached to the surface or is a bond to the surface; R is hydrogen or fluorine; M is hydrogen or fluorine; h is independently an integer of 2 or 3; j is 1; k is 0 or 1; m is 0 or an integer of 1 to 20; n is 0 or an integer of 1 to 20; the sum of (n+[(h+j)·k]+m) is an integer of 11 to 25; when k is 1, then m is at least 2 and M is hydrogen; and when k is 0 and R is fluorine, then m is at least 2 and M is hydrogen.

49. The microfluidic device of embodiment 48, wherein the self-associating molecules of the hydrophobic monolayer of the cover are the same as the self-associating molecules of the hydrophobic monolayer of the droplet actuating surface of the substrate.

50. The microfluidic device of any one of embodiments 47 to 49, wherein the outer hydrophobic layer of the inward-facing surface of the cover has a thickness of less than 5 nanometers.

51. The microfluidic device of any one of embodiments 47 to 50, wherein the inner layer of the cover is an inner dielectric layer.

52. The microfluidic device of embodiment 51, wherein the cover further comprises a photoresponsive layer.

53. The microfluidic device of embodiment 51, wherein the cover comprises a plurality of electrodes, each electrode configured to be connected to one or more AC voltage source(s).

54. The microfluidic device of embodiment 8, wherein the at least one spacing element comprises a silicon-based organic polymer.

55. The microfluidic device of embodiment 54, wherein the silicon-based organic polymer is selected from the group consisting of polydimethylsiloxane (PDMS) and photo-patternable silicone (PPS).

56. The microfluidic device of any one of embodiments 8 to 53, wherein the at least one spacing element comprises SU-8.

57. The microfluidic device of any one of embodiments 8 to 56, wherein the at least one spacing element has a thickness of at least 30 microns.

58. The microfluidic device of any one of embodiments 8 to 57, wherein the at least one spacing element defines one or more microchannels within the enclosure.

59. The microfluidic device of embodiment 58, wherein the at least one spacing element further defines a plurality of chambers within the enclosure, wherein each chamber opens off of at least one microchannel.

60. A method of manufacturing a microfluidic apparatus, the method comprising:
bonding a spacing element to an inner surface of a cover having at least one electrode configured to be connected to a voltage source;
bonding the spacing element and cover to a dielectric surface of a substrate having at least one electrode configured to be connected to a voltage source, whereby the spacing element becomes sandwiched between the inner surface of the cover and the dielectric surface of the substrate, with the cover and the substrate oriented substantially parallel to one another, and the substrate, spacing element, and cover collectively defining an enclosure configured to hold a liquid;
forming, by vapor deposition, a densely packed hydrophobic monolayer on at least a portion of the inner surface of the cover, wherein the hydrophobic monolayer comprises self-associating molecules covalently bonded to the inner surface of the cover; and forming, by vapor deposition, a densely packed hydrophobic monolayer on at least a portion of the dielectric surface of the substrate, wherein the hydrophobic monolayer comprises self-associating molecules covalently bonded to the dielectric surface of the substrate.

61. The method of embodiment 60, wherein the self-associating molecules of the hydrophobic monolayer of the cover and the self-associating molecules of the hydrophobic monolayer of the substrate each comprise a surface modifying ligand and a linking group that links the surface modifying ligand to the inner surface of the cover and the dielectric surface of the substrate, respectively, wherein the resulting surfaces of the cover and the substrate have a structure of Formula II:

Formula II

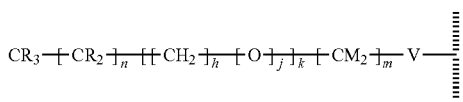

wherein ≣ is a surface of the dielectric layer; V is —P(O)(OY)W— or —Si(OZ)$_2$W—; W is —O—, —S—, or —NH— and connects to the surface; Z is a bond to an adjacent silicon atom attached to the surface or is a bond to the surface; Y is a bond to an adjacent phosphorus atom attached to the surface or is a bond to the surface; R is hydrogen or fluorine; M is hydrogen or fluorine; h is independently an integer of 2 or 3; j is 1; k is 0 or 1; m is 0 or an integer of 1 to 20; n is 0 or an integer of 1 to 20; the sum of (n+[(h+j)·k]+m) is an integer of 11 to 25; when k is 1, then m is at least 2 and M is hydrogen; and when k is 0 and R is fluorine, then m is at least 2 and M is hydrogen.

62. The method of embodiment 61, wherein V is —Si(OZ)$_2$W—.

63. The method of embodiment 61, wherein V is —P(O)(OY)W—.

64. The method of any one of embodiments 61 to 63, wherein n is an integer of 1 to 20, and wherein R is hydrogen.

65. The method of embodiment 64, wherein m is an integer of 1 to 20, and wherein M is hydrogen.

66. The method of embodiment 65, wherein m is 2.

67. The method of any one of embodiments 61 to 63, wherein n is an integer of 1 to 20, and wherein R is fluorine.

68. The method of embodiment 67, wherein m is an integer of 1 to 20, and wherein M is hydrogen.

69. The method of embodiment 68, wherein m is 2.

70. The method of any one of embodiments 61 to 69, wherein k is 1.

71. The method of any one of embodiments 61 to 69, wherein k is 0.

72. The microfluidic device of any one of embodiments 61 to 71, wherein the sum of (n+[(h+j)·k]+m) is an integer of 13 to 19.

73. A microfluidic apparatus comprising: a conductive silicon substrate having a dielectric stack and at least one electrode configured to be connected to a voltage source; a cover having at least one electrode configured to be connected to a voltage source; and at least one spacing element, wherein the conductive silicon substrate and the cover are substantially parallel to one another and joined together by the spacing element so as to define an enclosure configured to hold a liquid, wherein the conductive silicon substrate has an inward-facing surface that defines, in part, the enclosure, the inward-facing surface comprising the outermost surface of the dielectric stack, and wherein, when the at least one electrode of the substrate and the at least one electrode of the cover are connected to opposing terminals of an AC voltage source, the substrate is capable of applying an electrowetting force to aqueous droplets in contact with the inward-facing surface of the substrate.

74. The microfluidic apparatus of embodiment 73, wherein the conductive silicon substrate comprises amorphous silicon.

75. The microfluidic apparatus of embodiment 73 wherein the conductive silicon substrate comprises a phototransistor array.

76. The microfluidic apparatus of embodiment 73 wherein the conductive silicon substrate comprises an array of electrodes.

77. The microfluidic apparatus of any one of embodiments 73 to 76, wherein the inward-facing surface of the conductive silicon substrate further comprises an outer hydrophobic layer, the outer hydrophobic layer comprising self-associating molecules covalently bonded to the inner dielectric stack.

78. The microfluidic apparatus of any one of embodiments 73 to 77, wherein the inner dielectric stack comprises a first layer of dielectric material and a second layer of dielectric material.

79. The microfluidic apparatus of embodiment 78, wherein the first layer of dielectric material has a first surface and an opposing surface, wherein the first surface of the first layer adjoins the second layer, and wherein the opposing surface of the first layer forms the outermost surface of the dielectric stack.

80. The microfluidic apparatus of embodiment 78 or 79, wherein the first layer of dielectric material comprises a metal oxide.

81. The microfluidic apparatus of embodiment 80, wherein the first layer of dielectric material comprises aluminum oxide or hafnium oxide.

82. The microfluidic apparatus of any one of embodiments 78 to 81, wherein the second layer of dielectric material comprises an oxide or a nitride.

83. The microfluidic apparatus of embodiment 82, wherein the second layer of dielectric material comprises silicon oxide or silicon nitride.

84. The microfluidic apparatus of any one of embodiments 78 to 83, wherein the second layer is deposited by a Plasma Enhanced Chemical Vapor Deposition (PECVD) technique.

85. The microfluidic apparatus of any one of embodiments 78 to 84, wherein the first layer is deposited by an Atomic Layer Deposition (ALD) technique.

86. The microfluidic apparatus of any one of embodiments 78 to 85, wherein the inner dielectric stack comprises a third layer having a first surface and an opposing surface, wherein the first surface of the third layer adjoins the opposing surface of the first layer, and wherein the opposing surface of the third layer forms the outermost surface of the dielectric stack.

87. The microfluidic apparatus of embodiment 86, wherein the third layer comprises silicon oxide.

88. The microfluidic apparatus of embodiment 86 or 87, wherein the third layer is deposited by an Atomic Layer Deposition (ALD) technique.

89. The microfluidic apparatus of any one of embodiments 78 to 85, wherein the first layer of dielectric material has a thickness of about 10 nm to about 50 nm.

90. The microfluidic apparatus of any one of embodiments 86 to 88, wherein the first layer of dielectric material has a thickness of about 5 nm to about 20 nm and the third layer of dielectric material has a thickness of about 2 nm to about 10 nm.

91. The microfluidic apparatus of any one of embodiments 78 to 90, wherein the second layer of dielectric material has a thickness of about 30 nm to about 100 nm.

92. The microfluidic apparatus of any one of embodiments 73 to 91, wherein the dielectric stack of the droplet actuation surface of the substrate has a thickness of at least about 40 nanometers.

93. The microfluidic apparatus of embodiment 92, wherein the dielectric stack of the droplet actuation surface of the substrate has a thickness of about 40 nanometers to about 120 nanometers.

94. The microfluidic apparatus of any one of embodiments 73 to 93, wherein the dielectric layer has an impedance of about 50 kOhms to about 150 kOhms.

95. The microfluidic apparatus of any one of embodiments 73 to 94, wherein the apparatus comprises:
a dielectrophoresis module to perform a first microfluidic operation in response to a first applied voltage at a first frequency; and
an electrowetting module to receive an output from the dielectrophoresis module, and to perform a second microfluidic operation in response to a second applied voltage at a second frequency,
wherein the electrowetting module comprises the dielectric stack of the conductive silicon substrate.

96. The microfluidic apparatus of embodiment 95, further comprising a bridge between the first module and the second module.

97. The microfluidic apparatus of embodiment 96 wherein the bridge does not perform the first or second microfluidic operation.

98. The microfluidic apparatus of embodiment 96 or 97, wherein the bridge is an electrically neutral zone.

99. The microfluidic apparatus of any one of embodiments 96 to 98, wherein the bridge comprises tubing.

100. The microfluidic apparatus of any one of embodiments 96 to 98, wherein the bridge comprises a polymer.

101. The microfluidic apparatus of any one of embodiments 95 to 100, wherein the output is a biological material.

102. The microfluidic apparatus of any one of embodiments 95 to 101, wherein the first frequency is within a range of 100 kHz to 10 mHz.

103. The microfluidic apparatus of any one of embodiments 95 to 102, wherein the second frequency is within a range of 1 kHz to 300 kHz.

104. The microfluidic apparatus of any one of embodiments 95 to 103, wherein the first voltage is within a range 1 to 10 Volts.

105. The microfluidic apparatus of any one of embodiments 95 to 104, wherein the second voltage is within a range 10 to 100 Volts.

106. The microfluidic apparatus of any one of embodiments 95 to 105, wherein the conductive silicon substrate is monolithic.

107. The microfluidic apparatus of any one of embodiments 95 to 106, wherein the conductive silicon substrate is duolithic.

108. The microfluidic apparatus of embodiment 106, wherein the conductive silicon substrate comprises amorphous silicon.

109. The microfluidic apparatus of embodiment 107, wherein the conductive silicon substrate comprises amorphous silicon.

110. The microfluidic apparatus of embodiment 106, wherein the conductive silicon substrate comprises a phototransistor array.

111. The microfluidic apparatus of embodiment 107, wherein the conductive silicon substrate comprises a phototransistor array.

112. The microfluidic apparatus of embodiment 106, wherein the conductive silicon substrate comprises an array of electrodes.

113. The microfluidic apparatus of embodiment 107, wherein the conductive silicon substrate comprises an array of electrodes.

114. A system for transporting micro-objects, biological products, and/or reagents that are compatible with and/or soluble in aqueous media, the system comprising:
a microfluidic device having an enclosure comprising a base and a microfluidic circuit structure,
wherein the base comprises a hydrophobic monolayer covalently bonded to at least a portion of an upper surface of the base;
a first fluidic medium that is immiscible with aqueous media; and
at least one aqueous droplet.

115. The system of embodiment 114, wherein the hydrophobic monolayer has a surface modifying ligand and a linking group that links the surface modifying ligand to the surface, wherein the hydrophobic surface has a structure of Formula II:

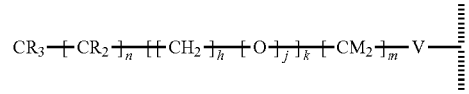

Formula II wherein ▦ is the surface; V is —P(O)(OY)W— or —Si(OZ)$_2$W—; W is —O—, —S—, or —NH— and connects to the surface; Z is a bond to an adjacent silicon atom attached to the surface or is a bond to the surface; Y is a bond to an adjacent phosphorus atom attached to the surface or is a bond to the surface; R is hydrogen or fluorine; M is hydrogen or fluorine; h is independently an integer of 2 or 3; j is 1; k is 0 or 1; m is 0 or an integer of 1 to 20; n is 0 or an integer of 1 to 20; the sum of (n+[(h+j)·k]+m) is an integer of 11 to 25; when k is 1, then m is at least 2 and M is hydrogen; and when k is 0 and R is fluorine, then m is at least 2 and M is hydrogen.

116. The system of embodiment 114 or 115, wherein the base comprises a conductive substrate.

117. The system of any one of embodiments 114 to 116, wherein the microfluidic device is a microfluidic device according to any one of embodiments 1 to 59.

118. The system of embodiment 117, wherein the microfluidic device comprises an optically actuated EW configuration.

119. The system of embodiment 117 or 118, wherein the microfluidic device further comprises a DEP configuration.

120. The system of any one of embodiments 114 to 119, wherein the first fluidic medium comprises at least one organic or organosilicon compound having a backbone structure comprising atoms selected from carbon, silicon, and oxygen.

121. The system of embodiment 120, wherein the backbone structure of the at least one organosilicon compound comprises silicon atoms, and optionally, oxygen atoms.

122. The system of embodiment 120, wherein the backbone structure of at least one organic compound comprises carbon atoms, and optionally, oxygen atoms.

123. The system of embodiment 122, wherein the backbone structure is branched.

124. The system of any one of embodiments 120 to 123, wherein the first fluidic medium comprises one or more acyclic organic or organosilicon compounds.

125. The system of embodiment 124, wherein the first fluidic medium consists of acyclic organic or organosilicon compounds.

126. The system of any one of embodiments 114 to 125, wherein the first fluidic medium does not comprise perfluorinated carbon atoms.

127. The system of any one of embodiments 114 to 125, wherein substituents of carbon atoms of a compound of the first fluidic medium comprise no more than 90% fluorine substituents.

128. The system of any one of embodiments 115 to 125, wherein the surface modifying ligand comprises at least a first portion comprising perfluorinated carbon atoms at an inward facing terminus of the hydrophobic monolayer.

129. The system of embodiment 128, wherein all carbon atoms of the hydrophobic monolayer are perfluorinated.

130. The system of any one of embodiments 114 to 129, wherein the first fluidic medium comprises more than one organic or organosilicon compound.

131. The system of any one of embodiments 114 to 130, wherein the enclosure further comprises a cover.

132. The system of embodiment 131, wherein the cover is transparent to light.

133. The system of embodiment 131 or 132, wherein the cover comprises glass and/or indium tantalum oxide (ITO).

134. The system of embodiments 131 to 133, wherein the cover comprises an electrode.

135. The system of any one of embodiments 114 to 134, wherein the aqueous droplet comprises a surfactant.

136. The system of embodiment 135, wherein the surfactant comprises a non-ionic surfactant.

137. The system of embodiment 135 or 136, wherein the surfactant comprises a block alkylene oxide copolymer, a fatty ester ethoxylated sorbitan, an ethoxylated fluorosurfactant, sodium dodecyl sulfate, or 2, 4, 7, 9, Tetramethyl-5-decyne-4,7,-diol ethoxylate.

138. The system of any one of embodiments 135 to 137, wherein the surfactant comprises Capstone® FS-30 (DuPont™, Synquest Laboratories).

139. The system of any one of embodiments 114 to 139, wherein the droplet comprises phosphate buffered saline solution.

140. The system of any one of embodiments 114 to 139, wherein the aqueous droplet comprises at least one micro-object.

141. The system of embodiment 140, wherein the micro-object is a biological micro-object.

142. The system of any one of embodiments 114 to 141, wherein the aqueous droplet comprises a biological product comprising nucleic acid and/or protein.

143. The system of any one of embodiments 114 to 142, wherein the aqueous droplet comprises a reagent.

144. A kit for transporting micro-objects, biological products, and/or reagents that are compatible with and/or soluble in aqueous media, the kit comprising:
   a microfluidic device having an enclosure comprising a base and a microfluidic circuit structure,
   wherein the base comprises a hydrophobic monolayer covalently bonded to at least a portion of an upper surface of the base; and a first fluidic medium that is immiscible with aqueous media.

145. The kit of embodiment 144, wherein the hydrophobic monolayer has a surface modifying ligand and a linking group that links the surface modifying ligand to the surface, wherein the hydrophobic surface has a structure of Formula II:

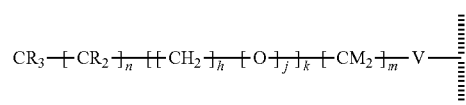

Formula II wherein ▊ is the surface; V is —P(O)(OY)W— or —Si(OZ)2W—; W is —O—, —S—, or —NH— and connects to the surface; Z is a bond to an adjacent silicon atom attached to the surface or is a bond to the surface; Y is a bond to an adjacent phosphorus atom attached to the surface or is a bond to the surface; R is hydrogen or fluorine; M is hydrogen or fluorine; h is independently an integer of 2 or 3; j is 1; k is 0 or 1; m is 0 or an integer of 1 to 20; n is 0 or an integer of 1 to 20; the sum of (n+[(h+j)·k]+m) is an integer of 11 to 25; when k is 1, then m is at least 2 and M is hydrogen; and when k is 0 and R is fluorine, then m is at least 2 and M is hydrogen.

146. The kit of embodiment 144 or 145, wherein the base comprises a conductive substrate.

147. The kit of any one of embodiments 144 to 146, wherein the microfluidic device is a microfluidic device according to any one of embodiments 1 to 59.

148. A process of operating the microfluidic apparatus of any one of embodiments 8 to 59, the process comprising:
   filling the enclosure, or a portion thereof, with a first liquid medium;
   applying an AC voltage potential between the at least one electrode of the substrate and the at least one electrode of the cover;
   introducing a first droplet of liquid into the enclosure, wherein the first droplet is immiscible in the first liquid medium; and
   moving the first droplet to a desired location within the enclosure by applying an electrowetting force to the first droplet.

149. The process of embodiment 148, wherein the first liquid medium is an oil.

150. The process of embodiment 148, wherein the first liquid medium is a silicone oil, a fluorinated oil, or a combination thereof.

151. The process of any one of embodiments 148 to 150, wherein the applied AC voltage potential is at least 20 ppV.

152. The process of embodiment 151, wherein the applied AC voltage potential is between about 25 and 35 ppV.

153. The process of any one of embodiments 148 to 152, wherein the applied AC voltage potential has a frequency of about 1 to 100 kHz.

154. The process of any one of embodiments 148 to 153, wherein the microfluidic apparatus comprises a droplet generator, and wherein the droplet generator introduces the first droplet into the enclosure.

155. The process of any one of embodiments 148 to 154, wherein the first droplet comprises an aqueous solution.

156. The process of embodiment 155, wherein the first droplet comprises at least one micro-object.

157. The process of embodiment 156, wherein the at least one micro-object is a biological micro-object.

158. The process of embodiment 157, wherein the biological micro-object is a cell.

159. The process of any one of embodiments 155 to 158, wherein the aqueous solution is a cell culture medium.

160. The process of embodiment 156, wherein the at least one micro-object is a capture bead having an affinity for a material of interest.

161. The process of embodiment 160, wherein the first droplet comprises two to twenty capture beads.

162. The process of embodiment 160, wherein the material of interest is a biological cell secretion.

163. The process of embodiment 160 or 161, wherein the material of interest is selected from the group consisting of DNA, genomic DNA, mitochondrial DNA, RNA, mRNA, miRNA, or any combination thereof.

164.164. The process of embodiment 155 or 156, wherein the first droplet comprises a reagent.

165. The process of embodiment 164, wherein the reagent is a cell lysis reagent.

166. The process of embodiment 165, wherein the reagent comprises a non-ionic detergent.

167. The process of embodiment 166, wherein the non-ionic detergent is at a concentration of less than 0.2%.

168. The process of embodiment 164, wherein the reagent is a proteolytic enzyme.

169. The process of embodiment 168, wherein the proteolytic enzyme can be inactivated.

170. The process of any one of embodiments 148 to 169, further comprising: introducing a second droplet of liquid into the enclosure, wherein the liquid of the second droplet is immiscible in the first liquid medium but miscible with the liquid of the first droplet; moving the second droplet to a location within the enclosure adjacent to the first droplet by applying an electrowetting force to the second droplet; and
merging the second droplet with the first droplet to form a first combined droplet.

171. The process of embodiment 170, wherein the second droplet is merged with the first droplet by applying an electrowetting force to the second and/or the first droplet.

172. The process of embodiment 170 or 171, wherein the first droplet comprises a biological micro-object, and wherein the second droplet comprises a reagent.

173. The process of embodiment 172, wherein the reagent contained in the second droplet is selected from the group consist of a lysis buffer, a fluorescent label, and a luminescent assay reagent.

174. The process of embodiment 172, wherein the reagent contained in the second droplet is a lysis buffer, and wherein said biological cell is lysed upon merger of the first droplet and the second droplet.

175. The process of any one of embodiments 170 to 174, further comprising:
introducing a third droplet of liquid into the enclosure, wherein the liquid of the third droplet is immiscible in the first liquid medium but miscible with the liquid of the first combined droplet; and moving the third droplet to a location within the enclosure adjacent to the first combined droplet by applying an electrowetting force to the third droplet; and
merging the third droplet with the first combined droplet to form a second combined droplet.

176. The process of embodiment 175, wherein the third droplet is merged with the first combined droplet by applying an electrowetting force to the third droplet and/or the first combined droplet.

177. The process of embodiment 175 or 176, wherein the third droplet comprises a reagent.

178. The process of embodiment 177, wherein the third droplet comprises a protease inhibitor.

179. The process of embodiment 177, wherein the third droplet comprises one to twenty capture beads having an affinity for a material of interest.

180. The process of embodiment 179, wherein the capture beads comprise oligonucleotide capture agents.

181. The process of embodiment 180, wherein the oligonucleotide capture agents are poly-dT oliognucleotides.

182. The process of any one of embodiments 179-181, wherein the material of interest is selected from the group consisting of DNA, genomic DNA, mitochondrial DNA, RNA, mRNA, miRNA, or any combination thereof.

183. The process of any one of embodiments 179-182, further comprising:
exporting the one to twenty capture beads from the microfluidic apparatus.

184. The process of any one of embodiments 175 to 183, further comprising:
introducing a fourth droplet of liquid into the enclosure, wherein the liquid of the fourth droplet is immiscible in the first liquid medium but miscible with the liquid of the second combined droplet; moving the fourth droplet to a location within the enclosure adjacent to the second combined droplet by applying an electrowetting force to the fourth droplet; and
merging the fourth droplet with the second combined droplet to form a third combined droplet.

185. The process of embodiment 184, wherein the fourth droplet is merged with the second combined droplet by applying an electrowetting force to the fourth droplet and/or the second combined droplet.

186. The process of embodiment 184 or 185, wherein the fourth droplet comprises a reagent.

187. The process of embodiment 186, wherein the reagent contained in the fourth droplet comprises a mixture comprising a buffer, dNTPs, and a polymerase suitable for performing a reverse transcription reaction.

188. The process of embodiment 186, wherein the reagent contained in the fourth droplet comprises a mixture comprising a buffer, dNTPs, and a polymerase suitable for performing a whole genome amplification reaction.

189. The process of any one of embodiments 148 to 188, wherein the first droplet, second droplet, third droplet, and fourth droplet each have a volume of about 5 to 50 nanoliters.

190. The process of embodiment 189, wherein the first droplet, the second droplet, and the third droplet each have a volume of about 5 to 20 nanoliters.

191. The process of embodiment 190, wherein the second droplet and/or the third droplet has a volume substantially equal to the volume of the first droplet.

192. The process of embodiment 190 or 191, wherein the fourth droplet has a volume about 1 to 3 times greater than the first droplet.

193. The process of embodiment 192, wherein the fourth droplet has a volume of about 10 to 30 nanoliters.

194. The process of any one of embodiments 148 to 193, wherein the enclosure comprises at least one microchannel.

195. The process of embodiment 194, wherein moving the first droplet to a desired location within the enclosure comprises moving the first droplet through the at least one microchannel.

196. The process of embodiment 194 or 195, wherein the enclosure further comprises a plurality of chambers that open off of the at least one microchannel.

197. The process of embodiment 196, wherein moving the first droplet to a desired location within the enclosure comprises moving the first droplet into one chamber of the plurality of chambers.

198. The process of any one of embodiments 194 to 197, wherein moving the second droplet to a position adjacent to the first droplet comprises moving the second droplet through the at least one microchannel and, optionally, into the chamber containing the first droplet.

199. The process of embodiment 198, wherein moving the third droplet to a position adjacent to the first combined droplet comprises moving the third droplet through the at least one microchannel and, optionally, into the chamber containing the first combined droplet.

200. The process of embodiment 199, wherein moving the fourth droplet to a position adjacent to the second combined droplet comprises moving the fourth droplet through the at least one microchannel and, optionally, into the chamber containing the second combined droplet.

201. The process of any one of embodiments 148 to 200, wherein applying an electrowetting force to move and/or merge droplets comprises changing an effective electrowetting characteristic of a region of the substrate surface proximal to the droplet(s).

202. The process of embodiment 201, wherein changing an effective electrowetting characteristic comprises activating electrowetting electrodes at the region of the substrate surface proximal to the droplet(s).

203. The process of embodiment 202, wherein the substrate comprises a photoresponsive layer, and wherein activating the electrowetting electrodes at the region of the substrate surface proximal to the droplet(s) comprises directing a pattern of light onto the region of the electrowetting surface.

EQUIVALENTS

The foregoing written specification is considered to be sufficient to enable one skilled in the art to practice the embodiments. The foregoing description and Examples detail certain embodiments and describes the best mode contemplated. It will be appreciated, however, that no matter how detailed the foregoing may appear in text, the embodiment may be practiced in many ways and should be construed in accordance with the appended claims and any equivalents thereof.

What is claimed:

1. A method of manufacturing a microfluidic apparatus, the method comprising:
bonding a spacing element to an inner surface of a cover having at least one electrode configured to be connected to a voltage source;
bonding the spacing element and cover to a dielectric surface of a substrate having at least one electrode configured to be connected to a voltage source, whereby the spacing element becomes sandwiched between the inner surface of the cover and the dielectric surface of the substrate, with the cover and the substrate oriented substantially parallel to one another, and the substrate, spacing element, and cover collectively defining an enclosure configured to hold a liquid;
forming, by vapor deposition, a densely packed hydrophobic monolayer on at least a portion of the inner surface of the cover, wherein the hydrophobic monolayer comprises self-associating molecules covalently bonded to the inner surface of the cover; and
forming, by vapor deposition, a densely packed hydrophobic monolayer on at least a portion of the dielectric surface of the substrate, wherein the hydrophobic monolayer comprises self-associating molecules covalently bonded to the dielectric surface of the substrate
wherein the self-associating molecules of the hydrophobic monolayer of the cover and the self-associating molecules of the hydrophobic monolayer of the substrate each comprise a surface modifying ligand and a linking group that links the surface modifying ligand to the inner surface of the cover and the dielectric surface of the substrate, respectively, wherein the resulting surfaces of the cover and the substrate have a structure of Formula II:

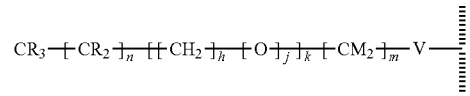

Formula II wherein ▮ is a surface of the dielectric layer;
V is —P(O)(OY)W— or —Si(OZ)$_2$W—;
W is —O—, —S—, or —NH— and connects to the surface;
Z is a bond to an adjacent silicon atom attached to the surface or is a bond to the surface;
Y is a bond to an adjacent phosphorus atom attached to the surface or is a bond to the surface;
R is hydrogen or fluorine;
M is hydrogen or fluorine;
h is independently an integer of 2 or 3;
j is 1;
k is 0 or 1;
m is 0 or an integer of 1 to 20
n is 0 or an integer of 1 to 20;
the sum of (n+[(h+j)·k]+m) is an integer of 11 to 25;
when k is 1, then m is at least 2 and M is hydrogen; and
when k is 0 and R is fluorine, then m is at least 2 and M is hydrogen.

2. The method of claim 1, wherein V is —Si(OZ)$_2$W—.
3. The method of claim 1, wherein V is —P(O)(OY)W—.
4. The method of claim 1, wherein n is an integer of 1 to 20, and wherein R is hydrogen.

5. The method of claim 4, wherein m is an integer of 1 to 20, and wherein M is hydrogen.

6. The method of claim 5, wherein m is 2.

7. The method of claim 1, wherein n is an integer of 1 to 20, and wherein R is fluorine.

8. The method of claim 7, wherein m is an integer of 1 to 20, and wherein M is hydrogen.

9. The method of claim 8, wherein m is 2.

10. The method of claim 1, wherein k is 1.

11. The method of claim 1, wherein k is 0.

12. The method of claim 1, wherein the sum of $(n+[(h+j)\cdot k]+m)$ is an integer of 13 to 19.

13. The method of claim 1, wherein the surface modifying ligand comprises at least a first portion comprising perfluorinated carbon atoms at an inward facing terminus of the hydrophobic monolayer.

14. The method of claim 13, wherein all carbon atoms of the hydrophobic monolayer are perfluorinated.

15. The method of claim 1, wherein the hydrophobic monolayer on at least a portion of the dielectric surface of the substrate has a thickness of less than 5 nanometers.

16. The method of claim 1, wherein the hydrophobic monolayer on at least a portion of the dielectric surface of the substrate is patterned such that select regions are relatively hydrophilic compared to the remainder of the hydrophobic monolayer.

17. The method of claim 1, further comprising:
depositing at least one dielectric layer by ALD on a surface of the substrate.

18. The method of claim 1, further comprising:
depositing at least one dielectric layer by PECVD on a surface of the substrate.

19. The method of claim 1, wherein the substrate further comprises an inner dielectric layer and a photoresponsive layer having a first side that contacts the inner dielectric layer and a second side that contacts the at least one electrode, wherein the dielectric surface of the substrate is a surface of the inner dielectric layer.

20. The method of claim 19, wherein the inner dielectric layer of the substrate comprises a first sublayer of dielectric material and a second sublayer of dielectric material, the first sublayer of dielectric material comprising an oxide.

21. The method of claim 20, wherein the oxide is a metal oxide.

22. The method of claim 21, wherein the metal oxide is aluminum oxide.

23. The method of claim 20, wherein the outer hydrophobic layer is covalently bonded to the first sublayer of dielectric material.

24. The method of claim 20, wherein the second sublayer of dielectric material comprises an oxide or a nitride.

25. The method of claim 24, wherein the second sublayer of dielectric material is selected from the group consisting of silicon dioxide and silicon nitride.

26. The method of claim 20, wherein the first sublayer of dielectric material comprises silicon oxide.

27. The method of claim 19, wherein the inner dielectric layer of the substrate has a thickness of about 40 nanometers to about 120 nanometers.

* * * * *